(12) United States Patent
Lollar

(10) Patent No.: US 7,033,791 B2
(45) Date of Patent: Apr. 25, 2006

(54) NUCLEIC ACID MOLECULES ENCODING MODIFIED FACTOR VIII PROTEINS, EXPRESSION PRODUCTS, AND METHODS OF MAKING THE SAME

(75) Inventor: John S. Lollar, Decatur, GA (US)

(73) Assignee: Emory University, Atlanta, GA (US)

( * ) Notice: Subject to any disclaimer, the term of this patent is extended or adjusted under 35 U.S.C. 154(b) by 687 days.

(21) Appl. No.: 10/131,510

(22) Filed: Apr. 23, 2002

(65) Prior Publication Data

US 2003/0166536 A1 Sep. 4, 2003

Related U.S. Application Data

(60) Division of application No. 09/315,179, filed on May 20, 1999, now Pat. No. 6,376,463, which is a continuation-in-part of application No. 09/037,601, filed on Mar. 10, 1998, now Pat. No. 6,180,371, which is a continuation-in-part of application No. 08/670,707, filed on Jun. 26, 1996, now Pat. No. 5,859,204, which is a continuation-in-part of application No. PCT/US94/13200, filed on Nov. 15, 1994, and a continuation-in-part of application No. 08/212,133, filed on Mar. 11, 1994, now Pat. No. 5,663,060, which is a continuation-in-part of application No. 07/864,004, filed on Apr. 7, 1992, now Pat. No. 5,364,771, said application No. 09/037, 601, is a continuation-in-part of application No. PCT/US97/11155, filed on Jun. 26, 1997, which is a continuation-in-part of application No. 08/670,707.

(51) Int. Cl.
*C12P 21/06* (2006.01)

(52) U.S. Cl. ............... 435/69.1; 435/6; 435/320.1; 435/252.3; 536/23.1; 536/23.4; 530/350; 514/2; 514/12

(58) Field of Classification Search ............... 435/69.1, 435/6, 320.1, 252.3; 530/350; 536/23.1, 23.4; 514/2, 12
See application file for complete search history.

(56) References Cited

U.S. PATENT DOCUMENTS

| 5,422,260 A | 6/1995 | Kaufman et al. ............ 435/212 |
| 5,451,521 A | 9/1995 | Kaufman et al. ......... 435/240.2 |
| 5,563,045 A | 10/1996 | Pittman et al. ............ 435/69.6 |
| 5,744,446 A | 4/1998 | Lollar et al. .................. 514/12 |

FOREIGN PATENT DOCUMENTS

| EP | 0 808 901 A2 | 11/1997 |
| EP | 306968 | 3/1998 |
| WO | 95/13300 | 5/1995 |
| WO | 95/18829 | 7/1995 |

OTHER PUBLICATIONS

Amano et al. (Jan. 1998) "The Molecular Basis for Cross-Reacting Material-Positive Hemophilia A Due to Missense Mutations Within the A–2 Domain of Factor VIII" *Blood* 9(2):538–548.

Cameron, C. et al. (1998) "The Canine Factor VIII cDNA and 5' Flanking Sequence" *Thromb. Haemost.* 79:317–322.

Fulcher et al. (Nov. 1985) "Localization of Human Factor and FVIII Inhibitor Epitopes to Two Polypeptide Fragments" *Proc. Natl. Acad. Sci.* 82:7728–7732.

Lind, P. et al. (1995) "Novel forms of B–domain–deleted recombinant factor VIII molecules, Construction and biochemical characterization" *Eur. J. Biochem.* 232:19–27.

Lollar et al. (1992) "Coagulant Properties of Hybrid Human/Porcine Factor VIII Molecules" *J. Biol. Chem.* 267(33): 23652–23657.

Scandella et al. (August 1988) "Epitope Mapping of Human Factor VIII Inhibitor Antibodies by Deletion Analysis of Factor VIII Fragments Expressed in Escherichia coli" *Proc. Natl. Acad. Sci.* 85:6152–6156.

Healey, JF et al. (Jun. 1995) "Residues 484–508 Contain a Major Determinant of the Inhibitory Epitope in the A2 Domain of Human Factor VIII;" *J. Biol. Chem.* 270(24):14505–14509.

Lubin, IM et al. (Mar. 1994) "Elimination of a Major Inhibitor Epitope in Factor VIII;" *J. Biol. Chem.* 269(12):8639–8641.

Primary Examiner—Jon Weber
Assistant Examiner—Hope Robinson
(74) Attorney, Agent, or Firm—Greenlee Winner and Sullivan, PC

(57) ABSTRACT

Specific amino acid loci of human factor VIII interact with inhibitory antibodies of hemophilia patients who have developed such antibodies after being treated with factor VIII. Modified factor VIII is disclosed in which the amino acid sequence is changed by a substitution at one or more amino acids of positions 484–508 of the A2 domain. The modified factor VIII is useful as a clotting factor supplement for hemophiliacs.

19 Claims, 6 Drawing Sheets

FIG. 1A

```
Signal peptide
Human  -19 MQIELSTCFF LCLLRFCFS
Pig        MQLELSTCVF LCLLPLGFS
Mouse      MQIALFACFF LSLFNFCSS
           **  * **** *     *
```

FIG. 1B

```
A1 domain
Human    1 ATRRYYLGAV ELSWDYMQSD LG-ELPVDAR FPPRVPKSFP FNTSVVYKKT
Pig        AIRRYYLGAV ELSWDYRQSE LLRELHVDTR FPATAPGALP LGPSVLYKKT
Mouse      AIRRYYLGAV ELSWNYIQSD LLSVLHTDSR FLPRMSTSFP FNTSIMYKKT
           ********** ****  * **  *   *  * *        *   *  * ****

50 LFVEFTDHLF NIAKPRPPWM GLLGPTIQAE VYDTVVITLK NMASHPVSLH
           VFVEFTDQLF SVARPRPPWM GLLGPTIQAE VYDTVVVTLK NMASHPVSLH
           VFVEYKDQLF NIAKPRPPWM GLLGPTIWTE VHDTVVITLK NMASHPVSLH
            ***  *  **    * ****** *******  *  * **** *** **********

100 AVGVSYWKAS EGAEYDDQTS QREKEDDKVF PGGSHTYVWQ VLKENGPMAS
           AVGVSFWKSS EGAEYEDHTS QREKEDDKVL PGKSQTYVWQ VLKENGPTAS
           AVGVSYWKAS EGDEYEDQTS QMEKEDDKVF PGESHTYVWQ VLKENGPMAS
           *****  ** * ** **** **  * *******  ** * *****  ******* **

150 DPLCLTYSYL SHVDLVKDLN SGLIGALLVC REGSLAKEKT QTLHKFILLF
           DPPCLTYSYL SHVDLVKDLN SGLIGALLVC REGSLTRERT QNLHEFVLLF
           DPPCLTYSYM SHVDLVKDLN SGLIGALLVC KEGSLSKERT QMLYQFVLLF
           ** ******  ********** ********** ****  *  *  *  *  * ***

200 AVFDEGKSWH SETKNSLMQD RDAASARAWP KMHTVNGYVN RSLPGLIGCH
           AVFDEGKSWH SARNDSWTRA MDPAPARAQP AMHTVNGYVN RSLPGLIGCH
           AVFDEGKSWH SETNDSYTQS MDSASARDWP KMHTVNGYVN RSLPGLIGCH
           **********  *    *     *  **   *  ********* **********

250 RKSVYWHVIG MGTTPEVHSI FLEGHTFLVR NHRQASLEIS PITFLTAQTL
           KKSVYWHVIG MGTSPEVHSI FLEGHTFLVR HHRQASLEIS PLTFLTAQTF
           RKSVYWHVIG MGTTPEIHSI FLEGHTFFVR NHRQASLEIS PITFLTAQTL
            ********* ***  ** *** *******  **  ********* ********
                                                APC/IXa      ♦
       300 LMDLGQFLLF CHISSHQHDG MEAYVKVDSC PEEPQLRMKN NEEAEDYDDD
           LMDLGQFLLF CHISSHHHGG MEAHVRVESC AEEPQLRRKA DE-EEDYDDN
           LIDLGQFLLF CHISSHKHDG MEAYVKVDSC PEESQWQKKN NN-EEMEDYD
           *  ******** ******  *  *** *  **  ** *    *       *  *
                                 IIa/Xa
       350 LTDSEMDVVR FDDDNSPSFI QIR
           LYDSDMDVVR LDGDDVSPFI QIR
           DDLYSEMDMF TLDYDSSPFI QIR
                              **  ***
```

A2 domain

```
Human  373 SVAKKHPKTW VHYIAAEEED WDYAPLVLAP DDRSYKSQYL NNGPQRIGRK      FIG. 1C
Pig        SVAKKHPKTW VHYISAEEED WDYAPAVPSP SDRSYKSLYL NSGPQRIGRK
Mouse      SVAKKYPKTW IHYISAEEED WDYAPSVPTS DNGSYKSQYL SNGPHRIGRK
           ***** **** *** ***** ***** *      **** **  ** *****

423 YKKVRFMAYT DETFKTREAI QHESGILGPL LYGEVGDTLL IIFKNQASRP
           YKKARFVAYT DVTFKTRKAI PYESGILGPL LYGEVGDTLL IIFKNKASRP
           YKKVRFIAYT DETFKTRETI QHESGLLGPL LYGEVGDTLL IIFKNQASRP
           *** ** *** * *****  *  *** **** ********** ***** ****
                                    A2 Inhibitor epitope
       473 YNIYPHGITD VRPLYSRRLP KGVKHLKDFP ILPGEIFKYK WTVTVEDGPT
           YNIYPHGITD VSALHPGRLL KGWKHLKDMP ILPGETFKYK WTVTVEDGPT
           YNIYPHGITD VSPLHARRLP RGIKHVKDLP IHPGEIFKYK WTVTVEDGPT
           **********  *  *   **  ** ** **  *  *** **** **********
                                                    F.IXa binding
                                                       APC
       523 KSDPRCLTRY YSSFVNMERD LASGLIGPLL ICYKE SVDQR  GNQIMSDKRN
           KSDPRCLTRY YSSSINLEKD LASGLIGPLL ICYKESVDQR GNQMMSDKRN
           KSDPRCLTRY YSSFINPERD LASGLIGPLL ICYKESVDQR GNQMMSDKRN
           **********  ***  * *  * ********** ********** *** ******

573 VILFSVFDEN RSWYLTENIQ RFLPNPAGVQ LEDPEFQASN IMHSINGYVF
           VILFSVFDEN QSWYLAENIQ RFLPNPDGLQ PQDPEFQASN IMHSINGYVF
           VILFSIFDEN QSWYITENMQ RFLPNAAKTQ PQDPGFQASN IMHSINGYVF
           ***** ****  ***  **  *   *****      *  ** *****  **********

623 DSLQLSVCLH EVAYWYILSI GAQTDFLSVF FSGYTFKHKM VYEDTLTLFP
           DSLQLSVCLH EVAYWYILSV GAQTDFLSVF FSGYTFKHKM VYEDTLTLFP
           DSLELTVCLH EVAYWHILSV GAQTDFLSIF FSGYTFKHKM VYEDTLTLFP
           *** * **** ***** ***  ********* * ********** **********
                                                         ♦♦
       673 FSGETVFMSM ENPGLWILGC HNSDFRNRGM TALLKVSSCD KNTGDYYEDS
           FSGETVFMSM ENPGLWVLGC HNSDLRNRGM TALLKVYSCD RDIGDYYDNT
           FSGETVFMSM ENPGLWVLGC HNSDFRKRGM TALLKVSSCD KSTSDYYEEI
           **********  ********** ****  *  *** ********** *    ***
           ♦              IIa/Xa/APC
       723 YEDISAYLLS KNNAIEPR
           YEDIPGFLLS GKNVIEPR
           YEDIPTQLVN ENNVIDPR
           ****   *     * *  **
```

```
B domain
Human   741 SFSQNSRHPS TRQKQFNATT IPENDIEKTD PWFAHRTPMP KIQNVSSSDL    FIG. 1D
Pig         SFAQNSRPPS ASQKQFQTIT SPEDDVE-LD PQSGERTQAL EELSVPSGDG
Mouse       SFFQNTNHPN TRKKKFKDST IPKNDMEKIE PQFEEIAEML KVQSVSVSDM
            ** **   *   *  *  * **   *                   *   *

791 LMLLRQS-PT PHGLSLSDLQ EAKYETFSDD PSPGAIDSNN SLSEMTHFRP
            SMLLGQN-PA PHGSSSSDLQ EARNEA--DD YLPGARERNT APSAAARLRP
            LMLLGQSHPT PHGLFLSDGQ EAIYEAIHDD HSPNAIDSNE GPSKVTQLRP
            *** *      ***     *  * **  *   **  *   *          **

840 QLHHSGDMVF TPESGLQLRL NEKLGTTAAT ELKKLDFKVS ST-SNNLIS-
            ELHHSAERVL TPEP------ ------EK   ELKKLDSKMS SSSDLLKTSP
            ESHHSEKIVF TPQPGLQLRS NKSLETTIEV KWKKLGLQVS SLPSNLMTT-
            *** *  **               ***    *

888 TIPSDNLAAGT DNTSSLGPPS MPVHYDSQLD TTLFGKKSSP LTESGGPLSL
            TIPSDTLSAET ERTHSLGPPH PQVNFRSQLG AIVLGKNSSH FIGAGVPLGS
            TILSDNLKATF EKTDSSGFPD MPVHSSSKLS TTAFGKKAYS LVGSHVPLNA
            ** ** * *    *  *  *    * *       **         **

939 SEENNDSKLL ESGLMNSQES SWGKNVSSTE SGRLFKGKRA HGPALLTKDN
            TEED------ ------HES  SLGENVSPVE SDGIFEKERA HGPASLTKDD
            SEENSDSNIL DSTLMYSQES LPRDNILSIE NDRLLREKRF HGIALLTKDN
            **             **     *  *      * ** * ****

989 ALFKVSISLL KTNKTSNNSA TNRKTHIDGP SLLIENSPSV WQNILESDTE
            VLFKVNISLV KTNKARVYLK TNRKIHIDDA ALLTENRAS- ----------
            TLFKDNVSLM KTNKTYNHST TNEKLHTESP TSIENSTTDL QDAILKVNSE
             ***   ** ****       ** *  *

1039 FKKVTPLIHD RMLMDKNATA LRLNHMSNKT TSSKNMEMVQ QKKEGPIPPD
            ---------- ATFMDKNTTA SGLNHVSN-- ---------- ----------
            IQEVTALIHD GTLLGKNSTY LRLNHMLNRT TSTKNKDIFH RKDEDPIPQD
              *  ***     **      *** *

1089 AQNPDMSFFK MLFLPESARW IQRTHGKNSL NSGQGPSPKQ LVSLGPEKSV
            ----------------- -----W IKGPLGKNPL SSERGPSPEL LTSSGSGKSV
            EENTIMPFSK MLFLSESSNW FKKTNGNNSL NSEQEHSPKQ LVYLMFKKYV
                              *       *** *   **  *        *  *

1139 EGQNFLSEKN KVVVGKGEFT KDVGLKEMVF PSSRNLFLTN LDNLHENNTH
            KGQSSGQGRI RVAVEEEELS KG---KEMML PNSELTFLTN SADVQGNDTH
            KNQSFLSEKN KVTVEQDGFT KNIGLKDMAF PHNMSIFLTT LSNVHENGRH
              *          * *        *       *  ***       *       *

1189 NQEKKIQEEI EKKETLIQEN VVLPQIHTVT GTKNFMKNLF LLSTRQNVEG
            SQGKKSREEM ERREKLVQEK VDLPQVYTAT GTKNFLRNIF HQSTEPSVEG
            NQEKNIQEEI EK-EALIEEK VVLPQVHEAT GSKNFLKDIL ILGTRQNI--
             *  *       *    * *  * ***   * *  ***

1239 SYDGAYAPVL QDFRSLNDST NRTKKHTAHF SK--KGEEEN LEGLGNQTKQ
            FDGGSHAPVP QDSRSLNDSA ERAETHIAHF SAIR--EEAP LEAPGNRT--
            SLYEVHVPVL QNITSINNST NTVQIHMEHF FKRRKDKETN SEGLVNKTRE
              *    *** *  *   * *        *  **       *    *     *
```

```
1287  IVEKYACTTR  ISPNTSQQNF  VTQRSKRALK  QFRLPLEETE  LEKRIIVDDT
      ----------  ---GPGPRSA  VPRRVKQSLK  QIRLPLEEIK  PERGVVLNAT
      MVKNYP----  -----SQKNI  TTQRSKRALG  QFRL------  ----------
```
FIG. 1D-1

```
1337  STQWSKNMKH  LTPSTLTQID  YNEKEKGAIT  QSPLSDCLTR  SHSIPQANRS
      STRWS-----  ----------  ----------  ----------  ----------
      STQWLKTINC  STQCIIKQID  HSKEMKKFIT  KSSLSDS-SV  IKSTTQTNSS
      **  *

1387  PLPIAKVSSF  PSIRPIYLTR  VLFQDNSSHL  PAASY----R  KKDSGVQESS
      ----------  ----------  ----------  ----------  -------ESS
      DSHIVKTSAF  P--*PIDLKR  SPFQNKFSHV  QASSYIYDFK  TKSSRIQESN
                                                          **

1433  HFLQGAKKNN  LSLAILTLEM  TGDQREVGSL  GTSATNSVTY  KKVENTVLPK
      PILQGAKRNN  LSLPFLTLEM  AGGQGKISAL  GKSAAGPLAS  GKLEKAVLSS
      NFLKETKINN  PSLAILPWNM  FIDQGKFTSP  GKSNTNSVTY  KKRENIIFLK
       *  * **   **   *   *    *         * *          * *

1483  PDLPKTSGKV  ELLPKVHIYQ  KDLFPTETSN  GSPGHLDLVE  GSLLQGTEGA
      AGLSEASGKA  EFLPKVRVHR  EDLLPQKTSN  VSCAHGDLGQ  EIFLQKTRGP
      PTLPEESGKI  ELLPQVSIQE  EEILPTETSH  GSPGHLNLMK  EVFLQKIQGP
          ***    *  ** *        *   *  *     *       ***   *

1533  IKWNEANRPG  KVPFLRVATE  SSAKTPSKLL  DPLAWDNHYG  TQIPKEEWKS
      VNLNKVNRPG  ----------  ---RTPSKLL  ---------G  PPMPKE-WES
      TKWNKAKRHG  ESIKGKTES-  -SKNTRSKLL  NHHAWDYHYA  AQIPKDMWKS
       *   *        * ****                  *   *

1583  QEKSPEKTAF  KKKDTI-LSLN  ACESNHAIAA  INEGQNKPEI  EVTWAKQGRT
      LEKSPKSTAL  RTKDIISLPLD  RHESNHSIAA  KNEGQAETQR  EAAWTKQGGP
      KEKSPEIISI  KQEDTI-LSLR  PHGNSHSIGA  -NEKQNWPQR  ETTWVKQGQT
      ****         *     *     ** *  ** *                 *  ***

1633  ERLCSONPPY  LKRHQR
      GRLCAPKPPV  LRRHQR
      QRTCSQIPPV  LKRHQR
        *  .**   * ****
```

Light chain activation peptide

```
                          ♦              ♦       IIa/Xa
Human  1649  EITRTTLQSDQEEIDYDDTISVEMKKEDFDIYDEDENQSPR
Pig          DISLPTFQPEEDKMDYDDIFSTETKGEDFDIYGEDENQDPR
Mouse        EL--SAFQSEQEATDYDDAITIET-IEDFDIYSEDIKQGPR
                *       ****   *  ****** **  * **
```
FIG. 1E A3 domain

```
                                     IXa Xa
Human 1690 SFQKKTRHYF IAAVERLWDY GMSSSPHVLR NRAQSGSVPQ FKKVVFQEFT
Pig        SFQKRTRHYF IAAVEQLWDY GMSESPRALR NRAQNGEVPR FKKVVFREFA
Mouse      SVQQKTRHYF IAAVERLWDY GMSTS-HVLR NRYQSDNVPQ FKKVVFQEFT.
           * * ***** ***** **** *** *   ** ** *   **  ****** **

1740 DGSFTQPLYR GELNEHLGLL GPYIRAEVED NIMVTFRNQA SRPYSFYSSL
          DGSFTQPSYR GELNKHLGLL GPYIRAEVED NIMVTFKNQA SRPYSFYSSL
          DGSFSQPLYR GELNEHLGLL GPYIRAEVED NIMVTFKNQA SRPYSFYSSL
          ****  ** ** **** ***** ********** ****** *** **********
                                     Factor IXa binding
     1790 ISYEEDQRQG AEPRKNFVKP NETKTYFWKV QHHMAPTKDE FDCKAWAYFS
          ISYPDDQEQG AEPRHNFVQP NETRTYFWKV QHHMAPTEDE FDCKAWAYFS
          ISYKEDQR-G EEPRRNFVKP NETKIYFWKV QHHMAPTEDE FDCKAWAYFS
          *** ** *  *** *** * ***  ***** ********** **********

1840 DVDLEKDVHS GLIGPLLVCH TNTLNPAHGR QVTVQEFALF FTIFDETKSW
          DVDLEKDVHS GLIGPLLICR ANTLNAAHGR QVTVQEFALF FTIFDETKSW
          DVDLERDMHS GLIGPLLICH ANTLNPAHGR QVSVQEFALL FTIFDETKSW
          ***** * ** ******* *  **** **** ** ****** **********

1890 YFTENMERNC RAPCNIQMED PTFKENYRFH AINGYIMDTL PGLVMAQDQR
          YFTENVERNC RAPCHLQMED PTLKENYRFH AINGYVMDTL PGLVMAQNQR
          YFTENVKRNC KTPCNFQMED PTLKENYRFH AINGYVMDTL PGLVMAQDQR
          *****  ***   **  ****  ** ** ******* ********** ******* **

1940 IRWYLLSMGS NENIHSIHFS GHVFTVRKKE EYKMALYNLY PGVFETVEML
          IRWYLLSMGS NENIHSIHFS GHVFSVRKKE EYKMAVYNLY PGVFETVEML
          IRWYLLSMGN NENIQSIHFS GHVFTVRKKE EYKMAVYNLY PGVFETLEMI
          ********* ****  ***** **** ***** ***** **** ****** **
                                     Protein C binding
     1990 PSKAGIWRVE CLIGEHLHAG MSTLFLVYSN
          PSKVGIWRIE CLIGEHLQAG MSTTFLVYSK
          PSRAGIWRVE CLIGEHLQAG MSTLFLVYSK
          ** **** * ******* ** *** ******
```

FIG. 1F

```
C1 domain
Human 2020  KCQTPLGMAS GHIRDFQITA SGQYGQWAPK LARLHYSGSI NAWSTKEPFS
Pig         ECQAPLGMAS GRIRDFQITA SGQYGQWAPK LARLHYSGSI NAWSTKDPHS
Mouse       QCQIPLGMAS GSIRDFQITA SGHYGQWAPN LARLHYSGSI NAWSTKEPFS
            ** ****** * ******** ** ****** ********** ****** * *

2070   WIKVDLLAPM IIHGIKTQGA RQKFSSLYIS QFIIMYSLDG KKWQTYRGNS
            WIKVDLLAPM IIHGIMTQGA RQKFSSLYIS QFIIMYSLDG RNWQSYRGNS
            WIKVDLLAPM IVHGIKTQGA RQKFSSLYIS QFIIMYSLDG KKWLSYQGNS
            ********** * *** **** ********** **********  *  * ***

2120   TGTLMVFFGN VDSSGIKHNI FNPPIIARYI RLHPTHYSIR STLRMELMGCDLN
            TGTLMVFFGN VDASGIKHNI FNPPIVARYI RLHPTHYSIR STLRMELMGCDLN
            TGTLMVFFGN VDSSGIKHNS FNPPIIARYI RLHPTHSSIR STLRMELMGCDLN
            ********** ** ****** ***** **** ****** *** *************
```

FIG. 1G

```
C2 domain            inhibitor epitope
Human 2173  SCSMPLGMES KAISDAQITA SSYFTNMFAT WSPSKARLHL QGRSNAWRPQ
Pig         SCSMPLGMQN KAISDSQITA SSHLSNIFAT WSPSQARLHL QGRTNAWRPR
Mouse       SCSIPLGMES KVISDTQITA SSYFTNMFAT WSPSQARLHL QGRTNAWRPQ
            *** ****   * *** ****  **   * *** **** ***** *** *****
                                              C2
     2223   VNNPKEWLQV DFQKTMKVTG VTTQGVKSLL TSMYVKEFLI SSSQDGHQWT
            VSSAEEWLQV DLQKTVKVTG ITTQGVKSLL SSMYVKEFLV SSSQDGRRWT
            VNDPKQWLQV DLQKTMKVTG IITQGVKSLF TSMFVKEFLI SSSQDGHHWT
            *    **** * *** **** ******** ** ***** ****** **
                                               Phospholipid
     2273   LFFQNGKVKV FQGNQDSFTP VVNSLDPPLL TRYLRIHPQS WVHQIALRME
            LFLQDGHTKV FQGNQDSSTP VVNALDPPLF TRYLRIHPTS WAQHIALRLE
            QILYNGKVKV FQGNQDSSTP MMNSLDPPLL TRYLRIHPQI WEHQIALRLE
            *  **  ********** *****  *********  *  ****.*
           binding
     2323  VLGCEAQDLY
           VLGCEAQDLY
           ILGCEAQQQY
           ******  *
```

FIG. 1H

SEQUENCE LISTING

<160> NUMBER OF SEQ ID NOS: 40

<210> SEQ ID NO 1
<211> LENGTH: 9009
<212> TYPE: DNA
<213> ORGANISM: Homo sapiens

<400> SEQUENCE: 1

```
cagtgggtaa gttccttaaa tgctctgcaa agaaattggg acttttcatt aaatcagaaa      60
ttttactttt ttccctcct gggagctaaa gatattttag agaagaatta accttttgct     120
tctccagttg aacatttgta gcaataagtc atgcaaatag agctctccac ctgcttcttt     180
ctgtgccttt tgcgattctg ctttagtgcc accagaagat actacctggg tgcagtggaa     240
ctgtcatggg actatatgca aagtgatctc ggtgagctgc ctgtggacgc aagatttcct     300
cctagagtgc caaaatcttt tccattcaac acctcagtcg tgtacaaaaa gactctgttt     360
gtagaattca cggttcacct tttcaacatc gctaagccaa ggccaccctg gatgggtctg     420
ctaggtccta ccatccaggc tgaggtttat gatacagtgg tcattacact taagaacatg     480
gcttcccatc ctgtcagtct tcatgctgtt ggtgtatcct actggaaagc ttctgaggga     540
gctgaatatg atgatcagac cagtcaaagg gagaaagaag atgataaagt cttccctggt     600
ggaagccata catatgtctg gcaggtcctg aaagagaatg gtccaatggc ctctgaccca     660
ctgtgcctta cctactcata tctttctcat gtggacctgg taaaagactt gaattcaggc     720
ctcattggag ccctactagt atgtagagaa gggagtctgg ccaaggaaaa gacacagacc     780
ttgcacaaat ttatactact ttttgctgta tttgatgaag ggaaaagttg gcactcagaa     840
acaaagaact ccttgatgca ggatagggat gctgcatctg ctcgggcctg gcctaaaatg     900
cacacagtca atggttatgt aaacaggtct ctgccaggtc tgattggatg ccacaggaaa     960
tcagtctatt ggcatgtgat tggaatgggc accactcctg aagtgcactc aatattcctc    1020
gaaggtcaca catttcttgt gaggaaccat cgccaggcgt ccttggaaat ctcgccaata    1080
actttcctta ctgctcaaac actcttgatg gaccttggac agtttctact gttttgtcat    1140
atctcttccc accaacatga tggcatggaa gcttatgtca aagtagacag ctgtccagag    1200
gaaccccaac tacgaatgaa aaataatgaa gaagcggaag actatgatga tgatcttact    1260
gattctgaaa tggatgtggt caggtttgat gatgacaact ctccttcctt tatccaaatt    1320
cgctcagttg ccaagaagca tcctaaaact tgggtacatt acattgctgc tgaagaggag    1380
gactgggact atgctcccct agtcctcgcc ccgatgaca gaagttataa aagtcaatat    1440
ttgaacaatg gccctcagcg gattggtagg aagtacaaaa aagtccgatt tatggcatac    1500
acagatgaaa cctttaagac tcgtgaagct attcagcatg aatcaggaat cttgggacct    1560
```

```
ttactttatg gggaagttgg agacacactg ttgattatat ttaagaatca agcaagcaga    1620
ccatataaca tctaccctca cggaatcact gatgtccgtc ctttgtattc aaggagatta    1680
ccaaaaggtg taaaacattt gaaggatttt ccaattctgc caggagaaat attcaaatat    1740
aaatggacag tgactgtaga agatgggcca actaaatcag atcctcggtg cctgacccgc    1800
tattactcta gtttcgttaa tatggagaga gatctagctt caggactcat tggccctctc    1860
ctcatctgct acaaagaatc tgtagatcaa agaggaaacc agataatgtc agacaagagg    1920
aatgtcatcc tgttttctgt atttgatgag aaccgaagct ggtacctcac agagaatata    1980
caacgctttc tccccaatcc agctggagtg cagcttgagg atccgagtt ccaagcctcc     2040 aacatcatgc acagcatcaa tggctatgtt tttgatagtt tgcagttgtc agtttgtttg    2100
catgaggtgg catactggta cattctaagc attggagcac agactgactt cctttctgtc    2160
ttcttctctg gatataccct caaacacaaa atggtctatg aagacacact caccctattc    2220 ccattcagg agaaactgt cttcatgtcg atggaaaacc caggtctatg gattctgggg      2280
tgccacaact cagactttcg gaacagagcc atgaccgcct tactgaaggt ttctagttgt    2340
gacaagaaca ctggtgatta ttacgaggac agttatgaag atatttcagc atacttgctg    2400
agtaaaaaca atgccattga accaagaagc ttctcccaga attcaagaca ccctagcact    2460
aggcaaaagc aatttaatgc caccacaatt ccagaaaatg acatagagaa gactgacccct  2520 tggtttgcac acagaacacc tatgcctaaa atacaaaatg tctcctctag tgatttgttg    2580
atgctcttgc gacagagtcc tactccacat gggctatcct tatctgatct ccaagaagcc   2640
aaatatgaga cttttttctga tgatccatca cctggagcaa tagacagtaa taacagcctg   2700
tctgaaatga cacacttcag gccacagctc catcacagtg gggacatggt atttacccct   2760
gagtcaggcc tccaattaag attaaatgag aaactgggga caactgcagc aacagagttg   2820
aagaaacttg atttcaaagt ttctagtaca tcaaataatc tgatttcaac aattccatca   2880
gacaatttgg cagcaggtac tgataataca agttccttag gacccccaag tatgccagtt   2940
cattatgata gtcaattaga taccactcta tttggcaaaa agtcatctcc ccttactgag    3000
tctggtggac ctctgagctt gagtgaagaa aataatgatt caaagttgtt agaatcaggt    3060
ttaatgaata gccaagaaag ttcatgggga aaaaatgtat cgtcaacaga gagtggtagg   3120
ttatttaaag ggaaaagagc tcatggacct gctttgttga ctaaagataa tgccttattc    3180
aaagttagca tctctttgtt aaagacaaac aaaaacttcca ataattcagc aactaataga   3240
aagactcaca ttgatggccc atcattatta attgagaata gtccatcagt ctggcaaaat    3300
atattagaaa gtgacactga gtttaaaaaa gtgacaccctt tgattcatga cagaatgctt   3360
atggacaaaa atgctacagc tttgaggcta aatcatatgt caaataaaac tacttcatca   3420
aaaaacatgg aaatggtcca acagaaaaaa gagggcccca ttccaccaga tgcacaaaat   3480
ccagatatgt cgttctttaa gatgctattc ttgccagaat cagcaaggtg gatacaaagg    3540
actcatggaa agaactctct gaactctggg caaggcccca gtccaaagca attagtatcc    3600
ttaggaccag aaaaatctgt ggaaggtcag aatttcttgt ctgagaaaaa caagtggta    3660 gtaggaaagg gtgaatttac aaaggacgta ggactcaaag agatggtttt tccaagcagc   3720
agaaacctat ttcttactaa cttggataat ttacatgaaa ataatacaca caatcaagaa    3780
aaaaaaattc aggaagaaat agaaagaag gaaacattaa tccaagagaa tgtagttttg    3840
cctcagatac atacagtgac tggcactaag aatttcatga agaaccttt cttactgagc    3900 actaggcaaa atgtagaagg ttcatatgag ggggcatatg ctccagtact tcaagatttt    3960
```

```
aggtcattaa atgattcaac aaatagaaca aagaaacaca cagctcattt ctcaaaaaaa      4020
ggggaggaag aaaacttgga aggcttggga aatcaaacca agcaaattgt agagaaatat      4080
gcatgcacca caaggatatc tcctaataca agccagcaga atttttgtcac gcaacgtagt    4140 aagagagctt tgaaacaatt cagactccca ctagaagaaa cagaacttga aaaaggata      4200 attgtggatg acacctcaac ccagtggtcc aaaaacatga aacatttgac cccgagcacc     4260
ctcacacaga tagactacaa tgagaaggag aaagggccca ttactcagtc tcccttatca     4320
gattgcctta cgaggagtca tagcatccct caagcaaata gatctccatt acccattgca     4380
aaggtatcat catttccatc tattagacct atatatctga ccagggtcct attccaagac     4440
aactcttctc atcttccagc agcatcttat agaaagaaag attctggggt ccaagaaagc     4500
agtcatttct tacaaggagc caaaaaaaat aacctttctt tagccattct aaccttggag     4560
atgactggtg atcaaagaga ggttggctcc ctggggacaa gtgccacaaa ttcagtcaca     4620
tacaagaaag ttgagaacac tgttctcccg aaaccagact tgcccaaaac atctggcaaa     4680
gttgaattgc ttccaaaagt tcacatttat cagaaggacc tattccctac ggaaactagc     4740
aatgggtctc ctggccatct ggatctcgtg aagggagcc ttcttcaggg aacagaggga      4800
gcgattaagt ggaatgaagc aaacagacct ggaaaagttc cctttctgag agtagcaaca     4860
gaaagctctg caaagactcc ctccaagcta ttggatcctc ttgcttggga taaccactat     4920
ggtactcaga taccaaaaga agagtggaaa tcccaagaga agtcaccaga aaaaacagct     4980
tttaagaaaa aggataccat tttgtccctg aacgcttgtg aaagcaatca tgcaatagca     5040
gcaataaatg agggacaaaa taagcccgaa atagaagtca cctgggcaaa gcaaggtagg     5100
actgaaaggc tgtgctctca aaacccacca gtcttgaaac gccatcaacg ggaaataact     5160
cgtactactc ttcagtcaga tcaagaggaa attgactatg atgataccat atcagttgaa     5220
atgaagaagg aagattttga catttatgat gaggatgaaa atcagagccc cgcagctttt    5280
caaaagaaaa cacgacacta ttttattgct gcagtggaga ggctctggga ttatgggatg     5340
agtagctccc cacatgttct aagaaacagg gctcagagtg gcagtgtccc tcagttcaag     5400
aaagttgttt tccaggaatt tactgatggc tcctttactc agcccttata ccgtggagaa     5460
ctaaatgaac atttgggact cctgggccaa tatataagag cagaagttga agataatatc     5520
atggtaactt tcagaaatca ggcctctcgt ccctattcct tctattctag ccttatttct     5580
tatgaggaag atcagaggca aggagcagaa cctagaaaaa actttgtcaa gcctaatgaa     5640
accaaaactt acttttggaa agtgcaacat catatggcac ccactaaaga tgagtttgac    5700
tgcaaagcct gggcttattt ctctgatgtt gacctgaaaa aagatgtgca ctcaggcctg     5760
attggacccc ttctggtctg ccacactaac acactgaacc ctgctcatgg gagacaagtg     5820
acagtacagg aatttgctct gttttttcacc atctttgatg agaccaaaag ctggtacttc    5880
actgaaaata tggaaagaaa ctgcagggct ccctgcaata tccagatgga agatcccact     5940
tttaaagaga attatcgctt ccatgcaatc aatggctaca taatggatac actacctggc    6000
ttagtaatgg ctcaggatca aaggattcga tggtatctgc tcagcatggg cagcaatgaa     6060
aacatccatt ctattcattt cagtggacat gtgttcactg tacgaaaaaa agaggagtat     6120
aaaatggcac tgtacaatct ctatccaggt gttttttgaga cagtggaaat gttaccatcc    6180
aaagctggaa tttggcgggt ggaatgcctt attggcgagc atctacatgc tgggatgagc     6240
acactttttc tggtgtacag caataagtgt cagactcccc tgggaatggc ttctggacac     6300
```

```
attagagatt ttcagattac agcttcagga caatatggac agtgggcccc aaagctggcc    6360
agacttcatt attccggatc aatcaatgcc tggagcacca aggagccctt ttcttggatc    6420
aaggtggatc tgttggcacc aatgattatt cacggcatca agacccaggg tgcccgtcag    6480
aagttctcca gcctctacat ctctcagttt atcatcatgt atagtcttga tgggaagaag    6540
tggcagactt atcgaggaaa ttccactgga accttaatgg tcttctttgg caatgtggat    6600
tcatctggga taaaacacaa tatttttaac cctccaatta ttgctcgata catccgtttg    6660
cacccaactc attatagcat tcgcagcact cttcgcatgg agttgatggg ctgtgattta    6720
aatagttgca gcatgccatt gggaatggag agtaaagcaa tatcagatgc acagattact    6780
gcttcatcct actttaccaa tatgtttgcc acctggtctc cttcaaaagc tcgacttcac    6840
ctccaaggga ggagtaatgc ctggagacct caggtgaata atccaaaaga gtggctgcaa    6900
gtggacttcc agaagacaat gaaagtcaca ggagtaacta ctcagggagt aaaatctctg    6960
cttaccagca tgtatgtgaa ggagttcctc atctccagca gtcaagatgg ccatcagtgg    7020
actctctttt ttcagaatgg caaagtaaag gttttcagg gaaatcaaga ctccttcaca    7080
cctgtggtga actctctaga cccaccgtta ctgactcgct accttcgaat tcaccccag    7140 agttgggtgc accagattgc cctgaggatg gaggttctgg gctgcgaggc acaggacctc    7200
tactgagggt ggccactgca gcacctgcca ctgccgtcac ctctccctcc tcagctccag    7260
ggcagtgtcc ctccctggct tgccttctac ctttgtgcta aatcctagca gacactgcct    7320
tgaagcctcc tgaattaact atcatcagtc ctgcatttct ttggtggggg gccaggaggg    7380
tgcatccaat ttaacttaac tcttacctat tttctgcagc tgctcccaga ttactccttc    7440
cttccaatat aactaggcaa aaagaagtga ggagaaacct gcatgaaagc attcttccct    7500
gaaaagttag gcctctcaga gtcaccactt cctctgttgt agaaaaacta tgtgatgaaa    7560 cttgaaaaa gatatttatg atgttaacat ttcaggttaa gcctcatacg tttaaaataa    7620
aactctcagt tgtttattat cctgatcaag catggaacaa agcatgtttc aggatcagat    7680
caatacaatc ttggagtcaa aaggcaaatc atttggacaa tctgcaaaat ggagagaata    7740
caataactac tacagtaaag tctgtttctg cttccttaca catagatata attatgttat    7800
ttagtcatta tgaggggcac attcttatct ccaaaactag cattcttaaa ctgagaatta    7860
tagatggggt tcaagaatcc ctaagtcccc tgaaattata taaggcattc tgtataaatg    7920
caaatgtgca ttttctgac gagtgtccat agatataaag ccattggtct taattctgac    7980
caataaaaaa ataagtcagg aggatgcaat tgttgaaagc tttgaaataa aataacatgt    8040
cttcttgaaa tttgtgatgg ccaagaaaga aaatgatgat gacattaggc ttctaaagga    8100
catacattta atatttctgt ggaaatatga ggaaaatcca tggttatctg agataggaga    8160
tacaaacttt gtaattctaa taatgcactc agtttactct ctccctctac taatttcctg    8220
ctgaaaataa cacaacaaaa atgtaacagg ggaaattata taccgtgact gaaaactaga    8280
gtcctactta catagttgaa atatcaagga ggtcagaaga aaattggact ggtgaaaaca    8340
gaaaaaacac tccagtctgc catatcacca cacaatagga tccccccttct tgccctccac    8400 ccccataaga ttgtgaaggg tttactgctc cttccatctg cctgcacccc ttcactatga    8460
ctacacagaa ctctccctgat agtaaagggg gctggaggca aggataagtt atagagcagt    8520
tggaggaagc atccaaagac tgcaacccag ggcaaatgga aaacaggaga tcctaatatg    8580
aaagaaaaat ggatcccaat ctgagaaaag gcaaagaat ggctactttt ttctatgctg    8640
gagtattttc taataatcct gcttgaccct tatctgacct cttttggaaac tataacatag    8700
```

```
ctgtcacagt atagtcacaa tccacaaatg atgcaggtgc aaatggttta tagccctgtg    8760
aagttcttaa agtttagagg ctaacttaca gaaatgaata agttgttttg ttttatagcc    8820
cggtagagga gttaacccca aaggtgatat ggttttattt cctgttatgt ttaacttgat    8880
aatcttattt tggcattctt ttcccattga ctatatacat ctctatttct caaatgttca    8940
tggaactagc tcttttattt tcctgctggt ttcttcagta atgagttaaa taaacattg     9000 acacataca                                                            9009
```

<210> SEQ ID NO 2
<211> LENGTH: 2332
<212> TYPE: PRT
<213> ORGANISM: Homo sapiens

<400> SEQUENCE: 2

```
Ala Thr Arg Arg Tyr Tyr Leu Gly Ala Val Glu Leu Ser Trp Asp Tyr
  1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Val His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
```

```
            305                 310                 315                 320
Glu Ala Tyr Val Lys Val Asp Ser Cys Pro Glu Pro Gln Leu Arg
                    325                 330                 335
Met Lys Asn Asn Glu Glu Ala Glu Asp Tyr Asp Asp Leu Thr Asp
                    340                 345                 350
Ser Glu Met Asp Val Val Arg Phe Asp Asp Asn Ser Pro Ser Phe
                    355                 360                 365
Ile Gln Ile Arg Ser Val Ala Lys Lys His Pro Lys Thr Trp Val His
        370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                    405                 410                 415
Gln Arg Ile Gly Arg Lys Tyr Lys Lys Val Arg Phe Met Ala Tyr Thr
                    420                 425                 430
Asp Glu Thr Phe Lys Thr Arg Glu Ala Ile Gln His Glu Ser Gly Ile
                    435                 440                 445
Leu Gly Pro Leu Leu Tyr Gly Glu Val Gly Asp Thr Leu Leu Ile Ile
        450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                    485                 490                 495
His Leu Lys Asp Phe Pro Ile Leu Pro Gly Glu Ile Phe Lys Tyr Lys
                    500                 505                 510
Trp Thr Val Thr Val Glu Asp Gly Pro Thr Lys Ser Asp Pro Arg Cys
                    515                 520                 525
Leu Thr Arg Tyr Tyr Ser Ser Phe Val Asn Met Glu Arg Asp Leu Ala
        530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                    565                 570                 575
Ser Val Phe Asp Glu Asn Arg Ser Trp Tyr Leu Thr Glu Asn Ile Gln
                    580                 585                 590
Arg Phe Leu Pro Asn Pro Ala Gly Val Gln Leu Glu Asp Pro Glu Phe
                    595                 600                 605
Gln Ala Ser Asn Ile Met His Ser Ile Asn Gly Tyr Val Phe Asp Ser
        610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                    645                 650                 655
Thr Phe Lys His Lys Met Val Tyr Glu Asp Thr Leu Thr Leu Phe Pro
                    660                 665                 670
Phe Ser Gly Glu Thr Val Phe Met Ser Met Glu Asn Pro Gly Leu Trp
                    675                 680                 685
Ile Leu Gly Cys His Asn Ser Asp Phe Arg Asn Arg Gly Met Thr Ala
        690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                    725                 730                 735
```

```
Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
            850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
                915                 920                 925

Leu Thr Glu Ser Gly Gly Pro Leu Ser Leu Ser Glu Glu Asn Asn Asp
            930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu Asn
    1010                1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
            1045                1050                1055

Thr Ala Leu Arg Leu Asn His Met Ser Asn Lys Thr Thr Ser Ser Lys
            1060                1065                1070

Asn Met Glu Met Val Gln Gln Lys Lys Glu Gly Pro Ile Pro Pro Asp
            1075                1080                1085

Ala Gln Asn Pro Asp Met Ser Phe Phe Lys Met Leu Phe Leu Pro Glu
            1090                1095                1100

Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
                1125                1130                1135

Ser Val Glu Gly Gln Asn Phe Leu Ser Glu Lys Asn Lys Val Val Val
            1140                1145                1150
```

-continued

Gly Lys Gly Glu Phe Thr Lys Asp Val Gly Leu Lys Glu Met Val Phe
        1155                1160                1165

Pro Ser Ser Arg Asn Leu Phe Leu Thr Asn Leu Asp Asn Leu His Glu
        1170                1175                1180

Asn Asn Thr His Asn Gln Glu Lys Lys Ile Gln Glu Glu Ile Glu Lys
1185                1190                1195                1200

Lys Glu Thr Leu Ile Gln Glu Asn Val Val Leu Pro Gln Ile His Thr
            1205                1210                1215

Val Thr Gly Thr Lys Asn Phe Met Lys Asn Leu Phe Leu Leu Ser Thr
        1220                1225                1230

Arg Gln Asn Val Glu Gly Ser Tyr Glu Gly Ala Tyr Ala Pro Val Leu
        1235                1240                1245

Gln Asp Phe Arg Ser Leu Asn Asp Ser Thr Asn Arg Thr Lys Lys His
        1250                1255                1260

Thr Ala His Phe Ser Lys Lys Gly Glu Glu Asn Leu Glu Gly Leu
1265                1270                1275                1280

Gly Asn Gln Thr Lys Gln Ile Val Glu Lys Tyr Ala Cys Thr Thr Arg
            1285                1290                1295

Ile Ser Pro Asn Thr Ser Gln Gln Asn Phe Val Thr Gln Arg Ser Lys
        1300                1305                1310

Arg Ala Leu Lys Gln Phe Arg Leu Pro Leu Glu Glu Thr Glu Leu Glu
        1315                1320                1325

Lys Arg Ile Ile Val Asp Asp Thr Ser Thr Gln Trp Ser Lys Asn Met
    1330                1335                1340

Lys His Leu Thr Pro Ser Thr Leu Thr Gln Ile Asp Tyr Asn Glu Lys
1345                1350                1355                1360

Glu Lys Gly Ala Ile Thr Gln Ser Pro Leu Ser Asp Cys Leu Thr Arg
            1365                1370                1375

Ser His Ser Ile Pro Gln Ala Asn Arg Ser Pro Leu Pro Ile Ala Lys
        1380                1385                1390

Val Ser Ser Phe Pro Ser Ile Arg Pro Ile Tyr Leu Thr Arg Val Leu
        1395                1400                1405

Phe Gln Asp Asn Ser Ser His Leu Pro Ala Ala Ser Tyr Arg Lys Lys
        1410                1415                1420

Asp Ser Gly Val Gln Glu Ser Ser His Phe Leu Gln Gly Ala Lys Lys
1425                1430                1435                1440

Asn Asn Leu Ser Leu Ala Ile Leu Thr Leu Glu Met Thr Gly Asp Gln
            1445                1450                1455

Arg Glu Val Gly Ser Leu Gly Thr Ser Ala Thr Asn Ser Val Thr Tyr
            1460                1465                1470

Lys Lys Val Glu Asn Thr Val Leu Pro Lys Pro Asp Leu Pro Lys Thr
        1475                1480                1485

Ser Gly Lys Val Glu Leu Leu Pro Lys Val His Ile Tyr Gln Lys Asp
        1490                1495                1500

Leu Phe Pro Thr Glu Thr Ser Asn Gly Ser Pro Gly His Leu Asp Leu
1505                1510                1515                1520

Val Glu Gly Ser Leu Leu Gln Gly Thr Glu Gly Ala Ile Lys Trp Asn
            1525                1530                1535

Glu Ala Asn Arg Pro Gly Lys Val Pro Phe Leu Arg Val Ala Thr Glu
            1540                1545                1550

Ser Ser Ala Lys Thr Pro Ser Lys Leu Leu Asp Pro Leu Ala Trp Asp
        1555                1560                1565

Asn His Tyr Gly Thr Gln Ile Pro Lys Glu Glu Trp Lys Ser Gln Glu

-continued

```
            1570                1575                1580
Lys Ser Pro Glu Lys Thr Ala Phe Lys Lys Asp Thr Ile Leu Ser
1585                1590                1595                1600

Leu Asn Ala Cys Glu Ser Asn His Ala Ile Ala Ala Ile Asn Glu Gly
                1605                1610                1615

Gln Asn Lys Pro Glu Ile Glu Val Thr Trp Ala Lys Gln Gly Arg Thr
                1620                1625                1630

Glu Arg Leu Cys Ser Gln Asn Pro Pro Val Leu Lys Arg His Gln Arg
                1635                1640                1645

Glu Ile Thr Arg Thr Thr Leu Gln Ser Asp Gln Glu Glu Ile Asp Tyr
                1650                1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
                1685                1690                1695

His Tyr Phe Ile Ala Ala Val Glu Arg Leu Trp Asp Tyr Gly Met Ser
                1700                1705                1710

Ser Ser Pro His Val Leu Arg Asn Arg Ala Gln Ser Gly Ser Val Pro
                1715                1720                1725

Gln Phe Lys Lys Val Val Phe Gln Glu Phe Thr Asp Gly Ser Phe Thr
                1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
                1765                1770                1775

Asn Gln Ala Ser Arg Pro Tyr Ser Phe Tyr Ser Ser Leu Ile Ser Tyr
                1780                1785                1790

Glu Glu Asp Gln Arg Gln Gly Ala Glu Pro Arg Lys Asn Phe Val Lys
                1795                1800                1805

Pro Asn Glu Thr Lys Thr Tyr Phe Trp Lys Val Gln His His Met Ala
                1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
                1845                1850                1855

Val Cys His Thr Asn Thr Leu Asn Pro Ala His Gly Arg Gln Val Thr
                1860                1865                1870

Val Gln Glu Phe Ala Leu Phe Phe Thr Ile Phe Asp Glu Thr Lys Ser
                1875                1880                1885

Trp Tyr Phe Thr Glu Asn Met Glu Arg Asn Cys Arg Ala Pro Cys Asn
                1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
                1925                1930                1935

Asp Gln Arg Ile Arg Trp Tyr Leu Leu Ser Met Gly Ser Asn Glu Asn
                1940                1945                1950

Ile His Ser Ile His Phe Ser Gly His Val Phe Thr Val Arg Lys Lys
                1955                1960                1965

Glu Glu Tyr Lys Met Ala Leu Tyr Asn Leu Tyr Pro Gly Val Phe Glu
                1970                1975                1980

Thr Val Glu Met Leu Pro Ser Lys Ala Gly Ile Trp Arg Val Glu Cys
1985                1990                1995                2000
```

Leu Ile Gly Glu His Leu His Ala Gly Met Ser Thr Leu Phe Leu Val
             2005                2010                2015

Tyr Ser Asn Lys Cys Gln Thr Pro Leu Gly Met Ala Ser Gly His Ile
         2020                2025                2030

Arg Asp Phe Gln Ile Thr Ala Ser Gly Gln Tyr Gly Gln Trp Ala Pro
         2035                2040                2045

Lys Leu Ala Arg Leu His Tyr Ser Gly Ser Ile Asn Ala Trp Ser Thr
         2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
             2085                2090                2095

Tyr Ile Ser Gln Phe Ile Ile Met Tyr Ser Leu Asp Gly Lys Lys Trp
             2100                2105                2110

Gln Thr Tyr Arg Gly Asn Ser Thr Gly Thr Leu Met Val Phe Phe Gly
             2115                2120                2125

Asn Val Asp Ser Ser Gly Ile Lys His Asn Ile Phe Asn Pro Pro Ile
             2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
             2165                2170                2175

Pro Leu Gly Met Glu Ser Lys Ala Ile Ser Asp Ala Gln Ile Thr Ala
             2180                2185                2190

Ser Ser Tyr Phe Thr Asn Met Phe Ala Thr Trp Ser Pro Ser Lys Ala
             2195                2200                2205

Arg Leu His Leu Gln Gly Arg Ser Asn Ala Trp Arg Pro Gln Val Asn
         2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
             2245                2250                2255

Val Lys Glu Phe Leu Ile Ser Ser Ser Gln Asp Gly His Gln Trp Thr
             2260                2265                2270

Leu Phe Phe Gln Asn Gly Lys Val Lys Val Phe Gln Gly Asn Gln Asp
             2275                2280                2285

Ser Phe Thr Pro Val Val Asn Ser Leu Asp Pro Pro Leu Leu Thr Arg
         2290                2295                2300

Tyr Leu Arg Ile His Pro Gln Ser Trp Val His Gln Ile Ala Leu Arg
2305                2310                2315                2320

Met Glu Val Leu Gly Cys Glu Ala Gln Asp Leu Tyr
             2325                2330

<210> SEQ ID NO 3
<211> LENGTH: 1130
<212> TYPE: DNA
<213> ORGANISM: Sus scrofa

<400> SEQUENCE: 3
taagcaccct aagacgtggg tgcactacat ctctgcagag gaggaggact gggactacgc    60
ccccgcggtc cccagcccca gtgacagaag ttataaaagt ctctacttga acagtggtcc   120
tcagcgaatt ggtaggaaat acaaaaaagc tcgattcgtc gcttacacgg atgtaacatt   180
taagactcgt aaagctattc cgtatgaatc aggaatcctg ggaccttttac tttatggaga   240

-continued

```
agttggagac acactttga ttatatttaa gaataaagcg agccgaccat ataacatcta    300
ccctcatgga atcactgatg tcagcgcttt gcacccaggg agacttctaa aaggttggaa    360
acatttgaaa gacatgccaa ttctgccagg agagactttc aagtataaat ggacagtgac    420
tgtggaagat gggccaacca agtccgatcc tcggtgcctg acccgctact actcgagctc    480
cattaatcta gagaaagatc tggcttcggg actcattggc cctctcctca tctgctacaa    540
agaatctgta gaccaaagag gaaaccagat gatgtcagac aagagaaacg tcatcctgtt    600
ttctgtattc gatgagaatc aaagctggta cctcgcagag aatattcagc gcttcctccc    660
caatccggat ggattacagc cccaggatcc agagttccaa gcttctaaca tcatgcacag    720
catcaatggc tatgtttttg atagcttgca gctgtcggtt tgtttgcacg aggtggcata    780
ctggtacatt ctaagtgttg gagcacagac ggacttcctc tccgtcttct tctctggcta    840
caccttcaaa cacaaaatgg tctatgaaga cacactcacc ctgttcccct tctcaggaga    900
aacggtcttc atgtcaatgg aaaacccagg tctctgggtc ctagggtgcc acaactcaga    960
cttgcggaac agagggatga cagccttact gaaggtgtat agttgtgaca gggacattgg   1020
tgattattat gacaacactt atgaagatat tccaggcttc ttgctgagtg gaaagaatgt   1080
cattgaaccc agaagctttg cccagaattc aagaccccct agtgcgagca                1130
```

<210> SEQ ID NO 4
<211> LENGTH: 368
<212> TYPE: PRT
<213> ORGANISM: Sus scrofa

<400> SEQUENCE: 4

```
Ser Val Ala Lys Lys His Pro Lys Thr Trp Val His Tyr Ile Ser Ala
 1               5                  10                  15

Glu Glu Glu Asp Trp Asp Tyr Ala Pro Ala Val Pro Ser Pro Ser Asp
            20                  25                  30

Arg Ser Tyr Lys Ser Leu Tyr Leu Asn Ser Gly Pro Gln Arg Ile Gly
        35                  40                  45

Arg Lys Tyr Lys Lys Ala Arg Phe Val Ala Tyr Thr Asp Val Thr Phe
    50                  55                  60

Lys Thr Arg Lys Ala Ile Pro Tyr Glu Ser Gly Ile Leu Gly Pro Leu
65                  70                  75                  80

Leu Tyr Gly Glu Val Gly Asp Thr Leu Leu Ile Ile Phe Lys Asn Lys
                85                  90                  95

Ala Ser Arg Pro Tyr Asn Ile Tyr Pro His Gly Ile Thr Asp Val Ser
            100                 105                 110

Ala Leu His Pro Gly Arg Leu Leu Lys Gly Trp Lys His Leu Lys Asp
        115                 120                 125

Met Pro Ile Leu Pro Gly Glu Thr Phe Lys Tyr Lys Trp Thr Val Thr
    130                 135                 140

Val Glu Asp Gly Pro Thr Lys Ser Asp Pro Arg Cys Leu Thr Arg Tyr
145                 150                 155                 160

Tyr Ser Ser Ser Ile Asn Leu Glu Lys Asp Leu Ala Ser Gly Leu Ile
                165                 170                 175

Gly Pro Leu Leu Ile Cys Tyr Lys Glu Ser Val Asp Gln Arg Gly Asn
            180                 185                 190

Gln Met Met Ser Asp Lys Arg Asn Val Ile Leu Phe Ser Val Phe Asp
        195                 200                 205

Glu Asn Gln Ser Trp Tyr Leu Ala Glu Asn Ile Gln Arg Phe Leu Pro
```

-continued

```
        210                 215                 220
Asn Pro Asp Gly Leu Gln Pro Gln Asp Pro Glu Phe Gln Ala Ser Asn
225                 230                 235                 240

Ile Met His Ser Ile Asn Gly Tyr Val Phe Asp Ser Leu Gln Leu Ser
                245                 250                 255

Val Cys Leu His Glu Val Ala Tyr Trp Tyr Ile Leu Ser Val Gly Ala
            260                 265                 270

Gln Thr Asp Phe Leu Ser Val Phe Ser Gly Tyr Thr Phe Lys His
        275                 280                 285

Lys Met Val Tyr Glu Asp Thr Leu Thr Leu Phe Pro Phe Ser Gly Glu
290                 295                 300

Thr Val Phe Met Ser Met Glu Asn Pro Gly Leu Trp Val Leu Gly Cys
305                 310                 315                 320

His Asn Ser Asp Leu Arg Asn Arg Gly Met Thr Ala Leu Leu Lys Val
                325                 330                 335

Tyr Ser Cys Asp Arg Asp Ile Gly Asp Tyr Tyr Asp Asn Thr Tyr Glu
            340                 345                 350

Asp Ile Pro Gly Phe Leu Leu Ser Gly Lys Asn Val Ile Glu Pro Arg
        355                 360                 365
```

<210> SEQ ID NO 5
<211> LENGTH: 7493
<212> TYPE: DNA
<213> ORGANISM: Mus musculus

<400> SEQUENCE: 5

```
tctagagttt ctttgctaca ggtaccaagg aacagtcttt tagaataggc taggaattta      60
aatacacctg aacgcccctc ctcagtattc tgttcctttt cttaaggatt caaacttgtt     120
aggatgcacc cagcaggaaa tgggttaagc cttagctcag ccactcttcc tattccagtt     180
ttcctgtgcc tgcttcctac tacccaaaag gaagtaatcc ttcagatctg ttttgtgcta     240
atgctacttt cactcacagt agataaactt ccagaaaatc ctctgcaaaa tatttaggac     300
ttttactaa atcattacat ttcttttgt tcttaaaagc taaagttatt ttagagaaga      360
gttaaatttt catttcttta gttgaacatt ttctagtaat aaaagccatg caaatagcac     420
tcttcgcttg cttctttctg agcctttca atttctgctc tagtgccatc agaagatact      480
accttggtgc agtggaattg tcctggaact atattcagag tgatctgctc agtgtgctgc     540
atacagactc aagatttctt cctagaatgt caacatcttt tccattcaac acctccatca     600
tgtataaaaa gactgtgttt gtagagtaca aggaccagct tttcaacatt gccaagccca     660
ggccaccctg gatgggtttg ctaggtccta ccatttggac tgaggttcat gacacagtgg     720
tcattacact taaaaacatg gcttctcatc ctgtcagtct tcatgctgtt ggtgtgtcct     780
actggaaagc ttctgaggga gatgaatatg aagatcagac aagccaaatg gagaaggaag     840
atgataaagt tttccctggt gaaagtcata cttatgtttg gcaagtcctg aaagagaatg     900
gtccaatggc ctctgaccct ccatgtctca cttactcata tatgtctcat gtggatctgg     960
tgaaagattt gaattcaggc ctcattggag ctctgctagt atgtaaagaa ggcagtctct    1020
ccaaagaaag aacacagatg ttgtaccaat ttgtactgct ttttgctgta tttgatgaag    1080
ggaagagctg gcactcagaa acaaacgact cttatacaca gtctatggat ctgcatctg     1140
ctagagactg gcctaaaatg cacacagtca atggctatgt aaacaggtct cttccaggtc    1200
tgattggatg ccataggaaa tcagtctact ggcacgtgat tggaatgggc accactcctg    1260
```

-continued

```
aaatacactc aatattcctc gaaggtcaca catttttttgt gaggaaccac cgtcaagctt    1320
cattggagat atcaccaata actttcctta ctgctcaaac actcttgata gatcttgggc    1380
agttcctact attttgtcat atctcttccc ataaacatga tggcatggaa gcttatgtca    1440
aagtagatag ctgccctgag gaatcccaat ggcaaaagaa aaataataat gaggaaatgg    1500
aagattatga tgatgatctt tattcagaaa tggatatgtt cacattggat tatgacagct    1560
ctccttttat ccaaattcgc tcggttgcta aaaagtaccc taaaacttgg atacattata    1620
tttctgctga ggaggaagac tgggactatg caccttcagt tcctacctcg gataatggaa    1680
gttataaaag ccagtatctg agcaatggtc ctcatcggat tggtaggaaa tataaaaaag    1740
tcagatttat agcatacaca gatgaaacct ttaagactcg tgaaactatt cagcatgaat    1800
caggactctt gggaccttta ctttatggag aagttggaga cacactgttg attatttta    1860 agaatcaagc aagccgacca tataacattt accctcatgg aatcactgat gtcagtcctc    1920
tacatgcaag gagattgcca agaggtataa agcacgtgaa ggatttgcca attcatccag    1980
gagagatatt caagtacaag tggacagtta cagtagaaga tggaccaact aaatcagatc    2040
cacggtgcct gacccgctat tattcaagtt tcattaaccc tgagagagat ctagcttcag    2100
gactgattgg ccctcttctc atctgctaca agaatctgt agatcaaagg ggaaaccaga    2160
tgatgtcaga caaagaaat gtcatcctgt tttctatatt tgatgagaac caaagctggt    2220
acatcacaga gaacatgcaa cgcttcctcc ccaatgcagc taaaacacag ccccaggacc    2280
ctgggttcca ggcctccaac atcatgcaca gcatcaatgg ctatgttttt gatagcttgg    2340
agttgacagt ttgtttgcat gaggtggcat actggcacat tctcagtgtt ggagcacaga    2400
cagacttctt atctatcttc ttctctggat atactttcaa acacaaaatg gtctatgaag    2460
atacacttac cctgttccca ttctcaggag aaactgtctt tatgtcgatg gaaaacccag    2520
gtctatgggt cttggggtgt cataattcag actttcggaa gagaggtatg acagcattgc    2580
tgaaagtttc tagttgtgac aagagcacta gtgattatta tgaagaaata tatgaagata    2640
ttccaacaca gttggtgaat gagaacaatg tcattgatcc cagaagcttc ttccagaata    2700
caaatcatcc taatactagg aaaaagaaat tcaaagattc cacaattcca aaaaatgata    2760
tggagaagat tgagcctcag tttgaagaga tagcagagat gcttaaagta cagagtgtct    2820
cagttagtga catgttgatg ctcttgggac agagtcatcc tactccacat ggcttatttt    2880
tatcagatgg ccaagaagcc atctatgagg ctattcatga tgatcattca ccaaatgcaa    2940
tagacagcaa tgaaggccca tctaaagtga cccaactcag gccagaatcc catcacagtg    3000
agaaaatagt atttactcct cagcccggcc tccagttaag atccaataaa agtttggaga    3060
caactataga agtaaagtgg aagaaacttg gtttgcaagt ttctagtttg ccaagtaatc    3120
taatgactac aacaattctg tcagacaatt gaaagcaac ttttgaaaag acagattctt    3180
caggatttcc agatatgcca gttcactcta gtagtaaatt aagtactact gcatttggta    3240
agaaagcata ttcccttgtt gggtctcatg tacctttaaa cgcgagtgaa gaaaatagtg    3300
attccaacat attggattca actttaatgt atagtcaaga aagttaccca agagataata    3360
tattatcaat agagaatgat agattactca gagagaagag gtttcatgga attgctttat    3420
tgaccaaaga taatactta ttcaaagaca atgtctcctt aatgaaaaca acaaaaacat    3480
ataatcattc aacaactaat gaaaaactac acactgagag cccaacatca attgagaata    3540
gtacaacaga cttgcaagat gccatattaa aggtcaatag tgagattcaa gaagtaacag    3600 cttttgattca tgatggaaca cttttaggca aaaattctac atatttgaga ctaaaccata    3660
```

```
tgctaaatag aactacctca acaaaaaata aagacatatt tcatagaaaa gatgaagatc    3720
ctattccaca agatgaagag aatacaatca tgccattttc caagatgttg ttcttgtcag    3780
aatcttcaaa ttggtttaaa aagaccaatg gaaataattc cttgaactct gagcaagaac    3840
atagtccaaa gcaattagta tatttaatgt ttaaaaaata tgtaaaaaat caaagtttct    3900
tgtcagagaa aaataaagtc acagtagaac aggatggatt tacaaagaac ataggactta    3960
aagacatggc ttttccacat aatatgagca tatttcttac cactttgtct aacgtacatg    4020
aaaatggtag gcacaatcaa gaaaaaaata ttcaggaaga gatagagaag gaagcactaa    4080
ttgaagagaa agtagttttg ccccaggtgc acgaagcaac tggctctaag aatttcttga    4140
aagacatatt gatactaggc actaggcaaa atataagttt atatgaagta catgtaccag    4200
tacttcaaaa catcacatca ataaacaatt caacaaatac agtacagatt cacatggagc    4260
atttctttaa aagaaggaag gacaaggaaa caaattcaga aggcttggta aataaaacca    4320
gagaaatggt aaaaaactat ccaagccaga agaatattac tactcaacgt agtaaacggg    4380 cttttgggaca attcagactg tcaactcaat ggcttaaaac cataaactgt tcaacacagt    4440
gtatcattaa acagatagac cacagcaagg aaatgaaaaa gttcattact aaatcttcct    4500
tatcagattc ttctgtgatt aaaagcacca ctcagacaaa tagttctgac tcacacattg    4560
taaaaacatc agcatttcca ccaatagatc tcaaaggag tccattccaa aacaaatttt    4620
ctcatgttca agcatcatcc tacatttatg actttaagac aaaaagttca agaattcaag    4680
aaagcaataa tttcttaaaa gaaaccaaaa taaataaccc ttctttagcc attctaccat    4740
ggaatatgtt catagatcaa ggaaaattta cctccccagg gaaaagtaac acaaactcag    4800
tcacatataa gaaacgtgag aacattattt tcttgaaacc aactttgcct gaagaatctg    4860
gcaaaattga attgcttcct caagtttcca ttcaagagga agaaatttta cctacagaaa    4920
ctagccatga atctcctgga cacttgaatc tcatgaaaga ggtctttctt cagaaaatac    4980
aggggcctac taaatggaat aaagcaaaga ggcatggaga agtataaaa ggtaaaacag    5040 agagctctaa aaatactcgc tcaaaactgc taaatcatca tgcttgggat tatcattatg    5100
ctgcacagat accaaaagat atgtggaaat ccaagagaa gtcaccagaa attatatcca    5160
ttaagcaaga ggacaccatt tgtctctga ggcctcatgg aaacagtcat tcaatagggg    5220
caaatgagaa acaaaattgg cctcaaagag aaaccacttg ggtaaagcaa ggccaaactc    5280
aaaggacatg ctctcaaatc ccaccagtgt tgaaacgaca tcaaagggaa cttagtgctt    5340
ttcaatcaga acaagaagca actgactatg atgatgccat caccattgaa acaatcgagg    5400
attttgacat ttacagtgag gacataaagc aaggtccccg cagctttcaa cagaaaacaa    5460
ggcactattt tattgcagct gtggaacgac tctgggacta tgggatgagt acatctcatg    5520
ttctacgaaa taggtatcaa agtgacaatg tacctcagtt caagaaagta gttttccagg    5580
aatttactga tggctccttt agtcagccct tatatcgtgg agaattaaat gaacacctgg    5640
ggttgttggg cccatatata agagcagaag ttgaagacaa cattatggta actttcaaaa    5700
accaggcctc ccgtccctac tccttctatt ctagcctcat ttcttataaa gaagatcaga    5760
gaggagaaga acctagaaga aactttgtca agcctaatga aaccaaaatt tatttttgga    5820
aagtacaaca tcatatggca cccacagaag atgagtttga ctgcaaggcc tgggcttatt    5880
tctctgatgt tgatcttgaa agagatatgc actcggggatt aattggaccc cttctgattt    5940
gccacgcgaa cacactgaat cctgctcatg ggagacaagt gtcagtacag gaatttgctc    6000
```

```
tgcttttcac tatctttgat gagaccaaga gctggtactt cactgaaaac gtgaaaagga    6060
actgcaagac accctgcaat tccagatgg aagaccccac tttgaaagag aattatcgct     6120
tccatgcaat caatggttat gtaatggata ccctaccagg cttagtaatg gctcaagatc    6180
aaaggattcg atggtatctt ctcagcatgg gcaacaatga gaacatccaa tctattcatt   6240
tcagtggaca tgttttcact gtacggaaaa aagaggagta taaatggca gtgtacaacc    6300 tctacccagg tgtttttgag actctggaaa tgataccatc cagagctgga atatggcgag    6360
tagaatgcct tattggcgag cacttacagg ctgggatgag cactcttttt ctggtgtaca    6420
gcaagcagtg tcagattcct cttggaatgg cttctggaag catccgtgat ttccagatta    6480
cagcttcagg acattatgga cagtgggccc caaacctggc aagacttcat tattccggat    6540
caatcaatgc ctggagtacc aaggagccct tttcttggat caaggtagat ctgttggcac    6600
caatgattgt tcatggcatc aagactcagg gtgctcgtca gaaatttttcc agcctttata   6660 tctctcaatt tatcatcatg tatagcctgg atgggaagaa gtggctgagt tatcaaggaa    6720
attccactgg aaccttaatg gttttctttg gcaatgtgga ctcatctggg attaagcata    6780
atagttttaa tcctccaatt attgctcgat atatccgttt gcaccccact cattctagca    6840
tccgtagtac tcttcgcatg gagttgatgg gctgtgatt aaacagttgc agcataccat     6900
tgggaatgga aagtaaagta atatcagata cacaaatcac tgcctcatcc tacttcacca    6960
acatgtttgc tacttggtct ccttcacaag ctcgacttca cctccaggga aggactaatg    7020
cctggcgacc tcaggtgaat gatccaaaac aatggttgca agtggactta caaaagacaa    7080
tgaaagtcac tggaataata acccagggag tgaaatctct ctttaccagc atgtttgtga    7140
aagagttcct tatttccagc agtcaagatg gccatcactg gactcaaatt ttatacaatg    7200
gcaaggtaaa ggttttttcag gggaatcagg actcatccac acctatgatg aattctctag    7260
acccaccatt actcactcgc tatcttcgaa ttcaccccca gatctgggag caccaaaattg   7320 ctctgaggct tgagattcta ggatgtgagg cccagcagca atactgaggt agcctctgca    7380
tcacctgctt attcccccttc ctcagctcaa agattgtctt aatgttttat tgctgtgaag    7440
agacactatg accatggcaa ctctttataa aataaagcat ttaatcaggg ctt           7493
```

<210> SEQ ID NO 6
<211> LENGTH: 2319
<212> TYPE: PRT
<213> ORGANISM: Mus musculus

<400> SEQUENCE: 6

```
Met Gln Ile Ala Leu Phe Ala Cys Phe Phe Leu Ser Leu Phe Asn Phe
 1               5                  10                  15

Cys Ser Ser Ala Ile Arg Arg Tyr Tyr Leu Gly Ala Val Glu Leu Ser
             20                  25                  30

Trp Asn Tyr Ile Gln Ser Asp Leu Leu Ser Val Leu His Thr Asp Ser
         35                  40                  45

Arg Phe Leu Pro Arg Met Ser Thr Ser Phe Pro Phe Asn Thr Ser Ile
     50                  55                  60

Met Tyr Lys Lys Thr Val Phe Val Glu Tyr Lys Asp Gln Leu Phe Asn
 65                  70                  75                  80

Ile Ala Lys Pro Arg Pro Pro Trp Met Gly Leu Leu Gly Pro Thr Ile
                 85                  90                  95

Trp Thr Glu Val His Asp Thr Val Val Ile Thr Leu Lys Asn Met Ala
            100                 105                 110
```

-continued

```
Ser His Pro Val Ser Leu His Ala Val Gly Val Ser Tyr Trp Lys Ala
        115                 120                 125

Ser Glu Gly Asp Glu Tyr Glu Asp Gln Thr Ser Gln Met Glu Lys Glu
        130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Met Ser His Val Asp Leu Val Lys Asp Leu Asn Ser Gly Leu
                180                 185                 190

Ile Gly Ala Leu Leu Val Cys Lys Glu Gly Ser Leu Ser Lys Glu Arg
                195                 200                 205

Thr Gln Met Leu Tyr Gln Phe Val Leu Leu Phe Ala Val Phe Asp Glu
        210                 215                 220

Gly Lys Ser Trp His Ser Glu Thr Asn Asp Ser Tyr Thr Gln Ser Met
225                 230                 235                 240

Asp Ser Ala Ser Ala Arg Asp Trp Pro Lys Met His Thr Val Asn Gly
                245                 250                 255

Tyr Val Asn Arg Ser Leu Pro Gly Leu Ile Gly Cys His Arg Lys Ser
                260                 265                 270

Val Tyr Trp His Val Ile Gly Met Gly Thr Thr Pro Glu Ile His Ser
        275                 280                 285

Ile Phe Leu Glu Gly His Thr Phe Phe Val Arg Asn His Arg Gln Ala
        290                 295                 300

Ser Leu Glu Ile Ser Pro Ile Thr Phe Leu Thr Ala Gln Thr Leu Leu
305                 310                 315                 320

Ile Asp Leu Gly Gln Phe Leu Leu Phe Cys His Ile Ser Ser His Lys
                325                 330                 335

His Asp Gly Met Glu Ala Tyr Val Lys Val Asp Ser Cys Pro Glu Glu
                340                 345                 350

Ser Gln Trp Gln Lys Lys Asn Asn Asn Glu Glu Met Glu Asp Tyr Asp
        355                 360                 365

Asp Asp Leu Tyr Ser Glu Met Asp Met Phe Thr Leu Asp Tyr Asp Ser
        370                 375                 380

Ser Pro Phe Ile Gln Ile Arg Ser Val Ala Lys Lys Tyr Pro Lys Thr
385                 390                 395                 400

Trp Ile His Tyr Ile Ser Ala Glu Glu Glu Asp Trp Asp Tyr Ala Pro
                405                 410                 415

Ser Val Pro Thr Ser Asp Asn Gly Ser Tyr Lys Ser Gln Tyr Leu Ser
                420                 425                 430

Asn Gly Pro His Arg Ile Gly Arg Lys Tyr Lys Lys Val Arg Phe Ile
        435                 440                 445

Ala Tyr Thr Asp Glu Thr Phe Lys Thr Arg Glu Thr Ile Gln His Glu
        450                 455                 460

Ser Gly Leu Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Ser Pro Leu His Ala Arg Arg Leu Pro Arg
                500                 505                 510

Gly Ile Lys His Val Lys Asp Leu Pro Ile His Pro Gly Glu Ile Phe
        515                 520                 525

Lys Tyr Lys Trp Thr Val Thr Val Glu Asp Gly Pro Thr Lys Ser Asp
```

-continued

```
            530                 535                 540
Pro Arg Cys Leu Thr Arg Tyr Tyr Ser Ser Phe Ile Asn Pro Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Met Met Ser Asp Lys Arg Asn Val
                580                 585                 590

Ile Leu Phe Ser Ile Phe Asp Glu Asn Gln Ser Trp Tyr Ile Thr Glu
                595                 600                 605

Asn Met Gln Arg Phe Leu Pro Asn Ala Ala Lys Thr Gln Pro Gln Asp
        610                 615                 620

Pro Gly Phe Gln Ala Ser Asn Ile Met His Ser Ile Asn Gly Tyr Val
625                 630                 635                 640

Phe Asp Ser Leu Glu Leu Thr Val Cys Leu His Glu Val Ala Tyr Trp
                645                 650                 655

His Ile Leu Ser Val Gly Ala Gln Thr Asp Phe Leu Ser Ile Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
        690                 695                 700

Gly Leu Trp Val Leu Gly Cys His Asn Ser Asp Phe Arg Lys Arg Gly
705                 710                 715                 720

Met Thr Ala Leu Leu Lys Val Ser Ser Cys Asp Lys Ser Thr Ser Asp
                725                 730                 735

Tyr Tyr Glu Glu Ile Tyr Glu Asp Ile Pro Thr Gln Leu Val Asn Glu
            740                 745                 750

Asn Asn Val Ile Asp Pro Arg Ser Phe Phe Gln Asn Thr Asn His Pro
            755                 760                 765

Asn Thr Arg Lys Lys Lys Phe Lys Asp Ser Thr Ile Pro Lys Asn Asp
        770                 775                 780

Met Glu Lys Ile Glu Pro Gln Phe Glu Glu Ile Ala Glu Met Leu Lys
785                 790                 795                 800

Val Gln Ser Val Ser Val Ser Asp Met Leu Met Leu Leu Gly Gln Ser
                805                 810                 815

His Pro Thr Pro His Gly Leu Phe Leu Ser Asp Gly Gln Glu Ala Ile
                820                 825                 830

Tyr Glu Ala Ile His Asp Asp His Ser Pro Asn Ala Ile Asp Ser Asn
            835                 840                 845

Glu Gly Pro Ser Lys Val Thr Gln Leu Arg Pro Glu Ser His His Ser
    850                 855                 860

Glu Lys Ile Val Phe Thr Pro Gln Pro Gly Leu Gln Leu Arg Ser Asn
865                 870                 875                 880

Lys Ser Leu Glu Thr Thr Ile Glu Val Lys Trp Lys Lys Leu Gly Leu
                885                 890                 895

Gln Val Ser Ser Leu Pro Ser Asn Leu Met Thr Thr Thr Ile Leu Ser
                900                 905                 910

Asp Asn Leu Lys Ala Thr Phe Glu Lys Thr Asp Ser Ser Gly Phe Pro
            915                 920                 925

Asp Met Pro Val His Ser Ser Ser Lys Leu Ser Thr Thr Ala Phe Gly
        930                 935                 940

Lys Lys Ala Tyr Ser Leu Val Gly Ser His Val Pro Leu Asn Ala Ser
945                 950                 955                 960
```

-continued

Glu Glu Asn Ser Asp Ser Asn Ile Leu Asp Ser Thr Leu Met Tyr Ser
            965                 970                 975

Gln Glu Ser Leu Pro Arg Asp Asn Ile Leu Ser Ile Glu Asn Asp Arg
            980                 985                 990

Leu Leu Arg Glu Lys Arg Phe His Gly Ile Ala Leu Leu Thr Lys Asp
            995                 1000                1005

Asn Thr Leu Phe Lys Asp Asn Val Ser Leu Met Lys Thr Asn Lys Thr
    1010                1015                1020

Tyr Asn His Ser Thr Thr Asn Glu Lys Leu His Thr Glu Ser Pro Thr
1025                1030                1035                1040

Ser Ile Glu Asn Ser Thr Thr Asp Leu Gln Asp Ala Ile Leu Lys Val
            1045                1050                1055

Asn Ser Glu Ile Gln Glu Val Thr Ala Leu Ile His Asp Gly Thr Leu
            1060                1065                1070

Leu Gly Lys Asn Ser Thr Tyr Leu Arg Leu Asn His Met Leu Asn Arg
            1075                1080                1085

Thr Thr Ser Thr Lys Asn Lys Asp Ile Phe His Arg Lys Asp Glu Asp
    1090                1095                1100

Pro Ile Pro Gln Asp Glu Glu Asn Thr Ile Met Pro Phe Ser Lys Met
1105                1110                1115                1120

Leu Phe Leu Ser Glu Ser Ser Asn Trp Phe Lys Lys Thr Asn Gly Asn
            1125                1130                1135

Asn Ser Leu Asn Ser Glu Gln Glu His Ser Pro Lys Gln Leu Val Tyr
            1140                1145                1150

Leu Met Phe Lys Lys Tyr Val Lys Asn Gln Ser Phe Leu Ser Glu Lys
            1155                1160                1165

Asn Lys Val Thr Val Glu Gln Asp Gly Phe Thr Lys Asn Ile Gly Leu
    1170                1175                1180

Lys Asp Met Ala Phe Pro His Asn Met Ser Ile Phe Leu Thr Thr Leu
1185                1190                1195                1200

Ser Asn Val His Glu Asn Gly Arg His Asn Gln Glu Lys Asn Ile Gln
            1205                1210                1215

Glu Glu Ile Glu Lys Glu Ala Leu Ile Glu Glu Lys Val Val Leu Pro
            1220                1225                1230

Gln Val His Glu Ala Thr Gly Ser Lys Asn Phe Leu Lys Asp Ile Leu
            1235                1240                1245

Ile Leu Gly Thr Arg Gln Asn Ile Ser Leu Tyr Glu Val His Val Pro
    1250                1255                1260

Val Leu Gln Asn Ile Thr Ser Ile Asn Asn Ser Thr Asn Thr Val Gln
1265                1270                1275                1280

Ile His Met Glu His Phe Phe Lys Arg Arg Lys Asp Lys Glu Thr Asn
            1285                1290                1295

Ser Glu Gly Leu Val Asn Lys Thr Arg Glu Met Val Lys Asn Tyr Pro
            1300                1305                1310

Ser Gln Lys Asn Ile Thr Thr Gln Arg Ser Lys Arg Ala Leu Gly Gln
    1315                1320                1325

Phe Arg Leu Ser Thr Gln Trp Leu Lys Thr Ile Asn Cys Ser Thr Gln
    1330                1335                1340

Cys Ile Ile Lys Gln Ile Asp His Ser Lys Glu Met Lys Lys Phe Ile
1345                1350                1355                1360

Thr Lys Ser Ser Leu Ser Asp Ser Ser Val Ile Lys Ser Thr Thr Gln
            1365                1370                1375

```
Thr Asn Ser Ser Asp Ser His Ile Val Lys Thr Ser Ala Phe Pro Pro
            1380                1385                1390

Ile Asp Leu Lys Arg Ser Pro Phe Gln Asn Lys Phe Ser His Val Gln
        1395                1400                1405

Ala Ser Ser Tyr Ile Tyr Asp Phe Lys Thr Lys Ser Ser Arg Ile Gln
    1410                1415                1420

Glu Ser Asn Asn Phe Leu Lys Glu Thr Lys Ile Asn Asn Pro Ser Leu
1425                1430                1435                1440

Ala Ile Leu Pro Trp Asn Met Phe Ile Asp Gln Gly Lys Phe Thr Ser
            1445                1450                1455

Pro Gly Lys Ser Asn Thr Asn Ser Val Thr Tyr Lys Lys Arg Glu Asn
        1460                1465                1470

Ile Ile Phe Leu Lys Pro Thr Leu Pro Glu Glu Ser Gly Lys Ile Glu
    1475                1480                1485

Leu Leu Pro Gln Val Ser Ile Gln Glu Glu Ile Leu Pro Thr Glu
1490                1495                1500

Thr Ser His Gly Ser Pro Gly His Leu Asn Leu Met Lys Glu Val Phe
1505                1510                1515                1520

Leu Gln Lys Ile Gln Gly Pro Thr Lys Trp Asn Lys Ala Lys Arg His
            1525                1530                1535

Gly Glu Ser Ile Lys Gly Lys Thr Glu Ser Ser Lys Asn Thr Arg Ser
        1540                1545                1550

Lys Leu Leu Asn His His Ala Trp Asp Tyr His Tyr Ala Ala Gln Ile
    1555                1560                1565

Pro Lys Asp Met Trp Lys Ser Lys Glu Lys Ser Pro Glu Ile Ile Ser
        1570                1575                1580

Ile Lys Gln Glu Asp Thr Ile Leu Ser Leu Arg Pro His Gly Asn Ser
1585                1590                1595                1600

His Ser Ile Gly Ala Asn Glu Lys Gln Asn Trp Pro Gln Arg Glu Thr
            1605                1610                1615

Thr Trp Val Lys Gln Gly Gln Thr Gln Arg Thr Cys Ser Gln Ile Pro
        1620                1625                1630

Pro Val Leu Lys Arg His Gln Arg Glu Leu Ser Ala Phe Gln Ser Glu
    1635                1640                1645

Gln Glu Ala Thr Asp Tyr Asp Asp Ala Ile Thr Ile Glu Thr Ile Glu
1650                1655                1660

Asp Phe Asp Ile Tyr Ser Glu Asp Ile Lys Gln Gly Pro Arg Ser Phe
1665                1670                1675                1680

Gln Gln Lys Thr Arg His Tyr Phe Ile Ala Ala Val Glu Arg Leu Trp
            1685                1690                1695

Asp Tyr Gly Met Ser Thr Ser His Val Leu Arg Asn Arg Tyr Gln Ser
        1700                1705                1710

Asp Asn Val Pro Gln Phe Lys Lys Val Val Phe Gln Glu Phe Thr Asp
    1715                1720                1725

Gly Ser Phe Ser Gln Pro Leu Tyr Arg Gly Glu Leu Asn Glu His Leu
        1730                1735                1740

Gly Leu Leu Gly Pro Tyr Ile Arg Ala Glu Val Glu Asp Asn Ile Met
1745                1750                1755                1760

Val Thr Phe Lys Asn Gln Ala Ser Arg Pro Tyr Ser Phe Tyr Ser Ser
            1765                1770                1775

Leu Ile Ser Tyr Lys Glu Asp Gln Arg Gly Glu Glu Pro Arg Arg Asn
        1780                1785                1790

Phe Val Lys Pro Asn Glu Thr Lys Ile Tyr Phe Trp Lys Val Gln His
```

-continued

His Met Ala Pro Thr Glu Asp Glu Phe Asp Cys Lys Ala Trp Ala Tyr
1795                1800                1805            1810

Phe Ser Asp Val Asp Leu Glu Arg Asp Met His Ser Gly Leu Ile Gly
1825                1830                1835            1840

Pro Leu Ile Cys His Ala Asn Thr Leu Asn Pro Ala His Gly Arg
            1845                1850                1855

Gln Val Ser Val Gln Glu Phe Ala Leu Leu Phe Thr Ile Phe Asp Glu
            1860                1865                1870

Thr Lys Ser Trp Tyr Phe Thr Glu Asn Val Lys Arg Asn Cys Lys Thr
    1875                1880                1885

Pro Cys Asn Phe Gln Met Glu Asp Pro Thr Leu Lys Glu Asn Tyr Arg
    1890                1895                1900

Phe His Ala Ile Asn Gly Tyr Val Met Asp Thr Leu Pro Gly Leu Val
1905                1910                1915                1920

Met Ala Gln Asp Gln Arg Ile Arg Trp Tyr Leu Leu Ser Met Gly Asn
                1925                1930                1935

Asn Glu Asn Ile Gln Ser Ile His Phe Ser Gly His Val Phe Thr Val
            1940                1945                1950

Arg Lys Lys Glu Glu Tyr Lys Met Ala Val Tyr Asn Leu Tyr Pro Gly
            1955                1960                1965

Val Phe Glu Thr Leu Glu Met Ile Pro Ser Arg Ala Gly Ile Trp Arg
1970                1975                1980

Val Glu Cys Leu Ile Gly Glu His Leu Gln Ala Gly Met Ser Thr Leu
1985                1990                1995                2000

Phe Leu Val Tyr Ser Lys Gln Cys Gln Ile Pro Leu Gly Met Ala Ser
                2005                2010                2015

Gly Ser Ile Arg Asp Phe Gln Ile Thr Ala Ser Gly His Tyr Gly Gln
            2020                2025                2030

Trp Ala Pro Asn Leu Ala Arg Leu His Tyr Ser Gly Ser Ile Asn Ala
            2035                2040                2045

Trp Ser Thr Lys Glu Pro Phe Ser Trp Ile Lys Val Asp Leu Leu Ala
    2050                2055                2060

Pro Met Ile Val His Gly Ile Lys Thr Gln Gly Ala Arg Gln Lys Phe
2065                2070                2075                2080

Ser Ser Leu Tyr Ile Ser Gln Phe Ile Ile Met Tyr Ser Leu Asp Gly
                2085                2090                2095

Lys Lys Trp Leu Ser Tyr Gln Gly Asn Ser Thr Gly Thr Leu Met Val
            2100                2105                2110

Phe Phe Gly Asn Val Asp Ser Ser Gly Ile Lys His Asn Ser Phe Asn
            2115                2120                2125

Pro Pro Ile Ile Ala Arg Tyr Ile Arg Leu His Pro Thr His Ser Ser
2130                2135                2140

Ile Arg Ser Thr Leu Arg Met Glu Leu Met Gly Cys Asp Leu Asn Ser
2145                2150                2155                2160

Cys Ser Ile Pro Leu Gly Met Glu Ser Lys Val Ile Ser Asp Thr Gln
            2165                2170                2175

Ile Thr Ala Ser Ser Tyr Phe Thr Asn Met Phe Ala Thr Trp Ser Pro
            2180                2185                2190

Ser Gln Ala Arg Leu His Leu Gln Gly Arg Thr Asn Ala Trp Arg Pro
        2195                2200                2205

Gln Val Asn Asp Pro Lys Gln Trp Leu Gln Val Asp Leu Gln Lys Thr
    2210                2215                2220

Met Lys Val Thr Gly Ile Ile Thr Gln Gly Val Lys Ser Leu Phe Thr
2225                2230                2235                2240

Ser Met Phe Val Lys Glu Phe Leu Ile Ser Ser Gln Asp Gly His
            2245                2250                2255

His Trp Thr Gln Ile Leu Tyr Asn Gly Lys Val Lys Val Phe Gln Gly
            2260                2265                2270

Asn Gln Asp Ser Ser Thr Pro Met Met Asn Ser Leu Asp Pro Pro Leu
            2275                2280                2285

Leu Thr Arg Tyr Leu Arg Ile His Pro Gln Ile Trp Glu His Gln Ile
        2290                2295                2300

Ala Leu Arg Leu Glu Ile Leu Gly Cys Glu Ala Gln Gln Gln Tyr
2305                2310                2315

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
ccttccttta tccaaatacg tagatcaaga ggaaattgac                        40

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
gtagcgttgc caagaagcac cctaagacg                                   29

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
gaagagtagt acgagttatt tctctgggtt caatgac                          37

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
cctttatcca aatacgtagc gtttgccaag aag                              33

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:degenerate
      oligonucleotide

```
<220> FEATURE:
<221> NAME/KEY: misc_feature
<222> LOCATION: (1)..(19)
<223> OTHER INFORMATION: r is a or g, y is c or t, and n is a, t, g or c
      at each occurrence

<400> SEQUENCE: 11
aarcayccna aracntggg                                                      19

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
gctcgcacta ggggtcttg aattc                                                25

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence:
      oligonucleotide primer, double-stranded from nucleotide 37-44, 3'
      end of short strand blocked with amino group

<400> SEQUENCE: 13
ctaatacgac tcactatagg gctcgagcgg ccgcccgggc aggt                          44

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
ccatcctaat acgactcact atagggc                                             27

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
ccattgacat gaagaccgtt tctc                                                24

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
actcactata gggctcgagc ggc                                                 23

<210> SEQ ID NO 17
<211> LENGTH: 24
```

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
gggtgcaaag cgctgacatc agtg                                           24

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
cctctcgagc caccatgtcg agccaccatg cagctagagc tctccacctg               50

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
cgcgcggccg cgcatctggc aaagctgagt t                                   31

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
gaaataagcc caggctttgc agtcraa                                        27

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(22)
<223> OTHER INFORMATION: at position 22 n is a or t or g or c

<400> SEQUENCE: 21
aggaaattcc actggaacct tn                                             22

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(25)
<223> OTHER INFORMATION: at position 25 n is a or t or g or c
```

```
<400> SEQUENCE: 22
ctgggggtga attcgaaggt agcgn                                           25

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
gagttcatcg ggaagacctg ttg                                             23

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
acagcccatc aactccatgc gaag                                            24

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
tcagggcaat caggactcc                                                  19

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
ccgtggtgaa cgctctggac c                                               21

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
gtagaggtcc tgtgcctcgc agcc                                            24

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
```

```
gtagagstsc tgkgcctcrc akccyag                                    27

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
cttcgcatgg agttgatggg ctgt                                       24

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
aatcaggact cctccacccc cg                                         22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
ggatccaccc cacgagctgg                                            20

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
cgccctgagg ctcgaggttc tagg                                       24

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
aatcaggact cctccacccc cg                                         22

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
```

```
                                                  -continued ccttgcagga attcgattca                                                    20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
ccgtggtgaa cgctctggac c                                                  21

<210> SEQ ID NO 36
<211> LENGTH: 6402
<212> TYPE: DNA
<213> ORGANISM: Sus scrofa
<220> FEATURE:
<221> NAME/KEY: CDS
<222> LOCATION: (1)..(6399)

<400> SEQUENCE: 36 atg cag cta gag ctc tcc acc tgt gtc ttt ctg tgt ctc ttg cca ctc          48
Met Gln Leu Glu Leu Ser Thr Cys Val Phe Leu Cys Leu Leu Pro Leu
 1               5                  10                  15 ggc ttt agt gcc atc agg aga tac tac ctg ggc gca gtg gaa ctg tcc          96
Gly Phe Ser Ala Ile Arg Arg Tyr Tyr Leu Gly Ala Val Glu Leu Ser
             20                  25                  30 tgg gac tac cgg caa agt gaa ctc ctc cgt gag ctg cac gtg gac acc         144
Trp Asp Tyr Arg Gln Ser Glu Leu Leu Arg Glu Leu His Val Asp Thr
         35                  40                  45 aga ttt cct gct aca gcg cca gga gct ctt ccg ttg ggc ccg tca gtc         192
Arg Phe Pro Ala Thr Ala Pro Gly Ala Leu Pro Leu Gly Pro Ser Val
     50                  55                  60 ctg tac aaa aag act gtg ttc gta gag ttc acg gat caa ctt ttc agc         240
Leu Tyr Lys Lys Thr Val Phe Val Glu Phe Thr Asp Gln Leu Phe Ser
 65                  70                  75                  80 gtt gcc agg ccc agg cca cca tgg atg ggt ctg ctg ggt cct acc atc         288
Val Ala Arg Pro Arg Pro Pro Trp Met Gly Leu Leu Gly Pro Thr Ile
                 85                  90                  95 cag gct gag gtt tac gac acg gtg gtc gtt acc ctg aag aac atg gct         336
Gln Ala Glu Val Tyr Asp Thr Val Val Val Thr Leu Lys Asn Met Ala
            100                 105                 110 tct cat ccc gtt agt ctt cac gct gtc ggc gtc tcc ttc tgg aaa tct         384
Ser His Pro Val Ser Leu His Ala Val Gly Val Ser Phe Trp Lys Ser
        115                 120                 125 tcc gaa ggc gct gaa tat gag gat cac acc agc caa agg gag aag gaa         432
Ser Glu Gly Ala Glu Tyr Glu Asp His Thr Ser Gln Arg Glu Lys Glu
    130                 135                 140 gac gat aaa gtc ctt ccc ggt aaa agc caa acc tac gtc tgg cag gtc         480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctc acc tac         528
Leu Lys Glu Asn Gly Pro Thr Ala Ser Asp Pro Pro Cys Leu Thr Tyr
                165                 170                 175 tca tac ctg tct cac gtg gac ctg gtg aaa gac ctg aat tcg ggc ctc         576
Ser Tyr Leu Ser His Val Asp Leu Val Lys Asp Leu Asn Ser Gly Leu
            180                 185                 190 att gga gcc ctg ctg gtt tgt aga gaa ggg agt ctg acc aga gaa agg         624
Ile Gly Ala Leu Leu Val Cys Arg Glu Gly Ser Leu Thr Arg Glu Arg
        195                 200                 205 acc cag aac ctg cac gaa ttt gta cta ctt ttt gct gtc ttt gat gaa         672
```

```
                Thr Gln Asn Leu His Glu Phe Val Leu Leu Phe Ala Val Phe Asp Glu
                                210                 215                 220 ggg aaa agt tgg cac tca gca aga aat gac tcc tgg aca cgg gcc atg              720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc              768
Asp Pro Ala Pro Ala Arg Ala Gln Pro Ala Met His Thr Val Asn Gly
                245                 250                 255 tat gtc aac agg tct ctg cca ggt ctg atc gga tgt cat aag aaa tca              816
Tyr Val Asn Arg Ser Leu Pro Gly Leu Ile Gly Cys His Lys Lys Ser
            260                 265                 270 gtc tac tgg cac gtg att gga atg ggc acc agc ccg gaa gtg cac tcc              864
Val Tyr Trp His Val Ile Gly Met Gly Thr Ser Pro Glu Val His Ser
        275                 280                 285 att ttt ctt gaa ggc cac acg ttt ctc gtg agg cac cat cgc cag gct              912
Ile Phe Leu Glu Gly His Thr Phe Leu Val Arg His His Arg Gln Ala
    290                 295                 300 tcc ttg gag atc tcg cca cta act ttc ctc act gct cag aca ttc ctg              960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac             1008
Met Asp Leu Gly Gln Phe Leu Leu Phe Cys His Ile Ser Ser His His
                325                 330                 335 cat ggt ggc atg gag gct cac gtc aga gta gaa agc tgc gcc gag gag             1056
His Gly Gly Met Glu Ala His Val Arg Val Glu Ser Cys Ala Glu Glu
            340                 345                 350 ccc cag ctg cgg agg aaa gct gat gaa gag gaa gat tat gat gac aat             1104
Pro Gln Leu Arg Arg Lys Ala Asp Glu Glu Glu Asp Tyr Asp Asp Asn
        355                 360                 365 ttg tac gac tcg gac atg gac gtg gtc cgg ctc gat ggt gac gac gtg             1152
Leu Tyr Asp Ser Asp Met Asp Val Val Arg Leu Asp Gly Asp Asp Val
    370                 375                 380 tct ccc ttt atc caa atc cgc tcg gtt gcc aag aag cat ccc aaa acc             1200
Ser Pro Phe Ile Gln Ile Arg Ser Val Ala Lys Lys His Pro Lys Thr
385                 390                 395                 400 tgg gtg cac tac atc tct gca gag gag gag gac tgg gac tac gcc ccc             1248
Trp Val His Tyr Ile Ser Ala Glu Glu Glu Asp Trp Asp Tyr Ala Pro
                405                 410                 415 gcg gtc ccc agc ccc agt gac aga agt tat aaa agt ctc tac ttg aac             1296
Ala Val Pro Ser Pro Ser Asp Arg Ser Tyr Lys Ser Leu Tyr Leu Asn
            420                 425                 430 agt ggt cct cag cga att ggt agg aaa tac aaa aaa gct cga ttc gtc             1344
Ser Gly Pro Gln Arg Ile Gly Arg Lys Tyr Lys Lys Ala Arg Phe Val
        435                 440                 445 gct tac acg gat gta aca ttt aag act cgt aaa gct att ccg tat gaa             1392
Ala Tyr Thr Asp Val Thr Phe Lys Thr Arg Lys Ala Ile Pro Tyr Glu
    450                 455                 460 tca gga atc ctg gga cct tta ctt tat gga gaa gtt gga gac aca ctt             1440
Ser Gly Ile Leu Gly Pro Leu Leu Tyr Gly Glu Val Gly Asp Thr Leu
465                 470                 475                 480 ttg att ata ttt aag aat aaa gcg agc cga cca tat aac atc tac cct             1488
Leu Ile Ile Phe Lys Asn Lys Ala Ser Arg Pro Tyr Asn Ile Tyr Pro
                485                 490                 495 cat gga atc act gat gtc agc gct ttg cac cca ggg aga ctt cta aaa             1536
His Gly Ile Thr Asp Val Ser Ala Leu His Pro Gly Arg Leu Leu Lys
            500                 505                 510 ggt tgg aaa cat ttg aaa gac atg cca att ctg cca gga gag act ttc             1584
Gly Trp Lys His Leu Lys Asp Met Pro Ile Leu Pro Gly Glu Thr Phe
        515                 520                 525
```

```
aag tat aaa tgg aca gtg act gtg gaa gat ggg cca acc aag tcc gat    1632
Lys Tyr Lys Trp Thr Val Thr Val Glu Asp Gly Pro Thr Lys Ser Asp
530             535                 540 cct cgg tgc ctg acc cgc tac tac tcg agc tcc att aat cta gag aaa    1680
Pro Arg Cys Leu Thr Arg Tyr Tyr Ser Ser Ser Ile Asn Leu Glu Lys
545             550                 555                 560 gat ctg gct tcg gga ctc att ggc cct ctc ctc atc tgc tac aaa gaa    1728
Asp Leu Ala Ser Gly Leu Ile Gly Pro Leu Leu Ile Cys Tyr Lys Glu
                565                 570                 575 tct gta gac caa aga gga aac cag atg atg tca gac aag aga aac gtc    1776
Ser Val Asp Gln Arg Gly Asn Gln Met Met Ser Asp Lys Arg Asn Val
580                 585                 590 atc ctg ttt tct gta ttc gat gag aat caa agc tgg tac ctc gca gag    1824
Ile Leu Phe Ser Val Phe Asp Glu Asn Gln Ser Trp Tyr Leu Ala Glu
            595                 600                 605 aat att cag cgc ttc ctc ccc aat ccg gat gga tta cag ccc cag gat    1872
Asn Ile Gln Arg Phe Leu Pro Asn Pro Asp Gly Leu Gln Pro Gln Asp
610                 615                 620 cca gag ttc caa gct tct aac atc atg cac agc atc aat ggc tat gtt    1920
Pro Glu Phe Gln Ala Ser Asn Ile Met His Ser Ile Asn Gly Tyr Val
625             630                 635                 640 ttt gat agc ttg cag ctg tcg gtt tgt ttg cac gag gtg gca tac tgg    1968
Phe Asp Ser Leu Gln Leu Ser Val Cys Leu His Glu Val Ala Tyr Trp
                645                 650                 655 tac att cta agt gtt gga gca cag acg gac ttc ctc tcc gtc ttc ttc    2016
Tyr Ile Leu Ser Val Gly Ala Gln Thr Asp Phe Leu Ser Val Phe Phe
            660                 665                 670 tct ggc tac acc ttc aaa cac aaa atg gtc tat gaa gac aca ctc acc    2064
Ser Gly Tyr Thr Phe Lys His Lys Met Val Tyr Glu Asp Thr Leu Thr
            675                 680                 685 ctg ttc ccc ttc tca gga gaa acg gtc ttc atg tca atg gaa aac cca    2112
Leu Phe Pro Phe Ser Gly Glu Thr Val Phe Met Ser Met Glu Asn Pro
690                 695                 700 ggt ctc tgg gtc cta ggg tgc cac aac tca gac ttg cgg aac aga ggg    2160
Gly Leu Trp Val Leu Gly Cys His Asn Ser Asp Leu Arg Asn Arg Gly
705                 710                 715                 720 atg aca gcc tta ctg aag gtg tat agt tgt gac agg gac att ggt gat    2208
Met Thr Ala Leu Leu Lys Val Tyr Ser Cys Asp Arg Asp Ile Gly Asp
            725                 730                 735 tat tat gac aac act tat gaa gat att cca ggc ttc ttg ctg agt gga    2256
Tyr Tyr Asp Asn Thr Tyr Glu Asp Ile Pro Gly Phe Leu Leu Ser Gly
            740                 745                 750 aag aat gtc att gaa ccc aga agc ttt gcc cag aat tca aga ccc cct    2304
Lys Asn Val Ile Glu Pro Arg Ser Phe Ala Gln Asn Ser Arg Pro Pro
            755                 760                 765 agt gcg agc caa aag caa ttc caa acc atc aca agt cca gaa gat gac    2352
Ser Ala Ser Gln Lys Gln Phe Gln Thr Ile Thr Ser Pro Glu Asp Asp
770                 775                 780 gtg gag ctt gac ccg cag tct gga gag aga acc caa gca ctg gaa gaa    2400
Val Glu Leu Asp Pro Gln Ser Gly Glu Arg Thr Gln Ala Leu Glu Glu
785                 790                 795                 800 cta agt gtc ccc tct ggt gat ggg tcg atg ctc ttg gga cag aat cct    2448
Leu Ser Val Pro Ser Gly Asp Gly Ser Met Leu Leu Gly Gln Asn Pro
            805                 810                 815 gct cca cat ggc tca tcc tca tct gat ctt caa gaa gcc agg aat gag    2496
Ala Pro His Gly Ser Ser Ser Ser Asp Leu Gln Glu Ala Arg Asn Glu
                820                 825                 830 gct gat gat tat tta cct gga gca aga gaa aga acg gcc cca tcc        2544
Ala Asp Asp Tyr Leu Pro Gly Ala Arg Glu Arg Asn Thr Ala Pro Ser
                835                 840                 845
```

-continued

| | | |
|---|---|---|
| gca gcg gca cgt ctc aga cca gag ctg cat cac agt gcc gaa aga gta<br>Ala Ala Ala Arg Leu Arg Pro Glu Leu His His Ser Ala Glu Arg Val<br>850                               855                     860 | | 2592 |
| ctt act cct gag cca gag aaa gag ttg aag aaa ctt gat tca aaa atg<br>Leu Thr Pro Glu Pro Glu Lys Glu Leu Lys Lys Leu Asp Ser Lys Met<br>865                               870                    875                    880 | | 2640 |
| tct agt tca tca gac ctt cta aag act tcg cca aca att cca tca gac<br>Ser Ser Ser Ser Asp Leu Leu Lys Thr Ser Pro Thr Ile Pro Ser Asp<br>                          885                    890                        895 | | 2688 |
| acg ttg tca gcg gag act gaa agg aca cat tcc tta ggc ccc cca cac<br>Thr Leu Ser Ala Glu Thr Glu Arg Thr His Ser Leu Gly Pro Pro His<br>      900                           905                         910 | | 2736 |
| ccg cag gtt aat ttc agg agt caa tta ggt gcc att gta ctt ggc aaa<br>Pro Gln Val Asn Phe Arg Ser Gln Leu Gly Ala Ile Val Leu Gly Lys<br>              915                        920                    925 | | 2784 |
| aat tca tct cac ttt att ggg gct ggt gtc cct ttg ggc tcg act gag<br>Asn Ser Ser His Phe Ile Gly Ala Gly Val Pro Leu Gly Ser Thr Glu<br>930                               935                    940 | | 2832 |
| gag gat cat gaa agc tcc ctg gga gaa aat gta tca cca gtg gag agt<br>Glu Asp His Glu Ser Ser Leu Gly Glu Asn Val Ser Pro Val Glu Ser<br>945                               950                    955                    960 | | 2880 |
| gac ggg ata ttt gaa aag gaa aga gct cat gga cct gct tca ctg acc<br>Asp Gly Ile Phe Glu Lys Glu Arg Ala His Gly Pro Ala Ser Leu Thr<br>                          965                    970                        975 | | 2928 |
| aaa gac gat gtt tta ttt aaa gtt aat atc tct ttg gta aag aca aac<br>Lys Asp Asp Val Leu Phe Lys Val Asn Ile Ser Leu Val Lys Thr Asn<br>              980                        985                    990 | | 2976 |
| aag gca cga gtt tac tta aaa act aat aga aag att cac att gat gac<br>Lys Ala Arg Val Tyr Leu Lys Thr Asn Arg Lys Ile His Ile Asp Asp<br>           995                      1000                  1005 | | 3024 |
| gca gct tta tta act gag aat agg gca tct gca acg ttt atg gac aaa<br>Ala Ala Leu Leu Thr Glu Asn Arg Ala Ser Ala Thr Phe Met Asp Lys<br>1010                            1015                  1020 | | 3072 |
| aat act aca gct tcg gga tta aat cat gtg tca aat tgg ata aaa ggg<br>Asn Thr Thr Ala Ser Gly Leu Asn His Val Ser Asn Trp Ile Lys Gly<br>1025                            1030                    1035                  1040 | | 3120 |
| ccc ctt ggc aag aac ccc cta agc tcg gag cga ggc ccc agt cca gag<br>Pro Leu Gly Lys Asn Pro Leu Ser Ser Glu Arg Gly Pro Ser Pro Glu<br>                        1045                    1050                    1055 | | 3168 |
| ctt ctg aca tct tca gga tca gga aaa tct gtg aaa ggt cag agt tct<br>Leu Leu Thr Ser Ser Gly Ser Gly Lys Ser Val Lys Gly Gln Ser Ser<br>                    1060                    1065                  1070 | | 3216 |
| ggg cag ggg aga ata cgg gtg gca gtg gaa gag gaa gaa ctg agc aaa<br>Gly Gln Gly Arg Ile Arg Val Ala Val Glu Glu Glu Glu Leu Ser Lys<br>              1075                    1080                    1085 | | 3264 |
| ggc aaa gag atg atg ctt ccc aac agc gag ctc acc ttt ctc act aac<br>Gly Lys Glu Met Met Leu Pro Asn Ser Glu Leu Thr Phe Leu Thr Asn<br>1090                            1095                    1100 | | 3312 |
| tcg gct gat gtc caa gga aac gat aca cac agt caa gga aaa aag tct<br>Ser Ala Asp Val Gln Gly Asn Asp Thr His Ser Gln Gly Lys Lys Ser<br>1105                            1110                    1115                  1120 | | 3360 |
| cgg gaa gag atg gaa agg aga gaa aaa tta gtc caa gaa aaa gtc gac<br>Arg Glu Glu Met Glu Arg Arg Glu Lys Leu Val Gln Glu Lys Val Asp<br>                    1125                    1130                  1135 | | 3408 |
| ttg cct cag gtg tat aca gcg act gga act aag aat ttc ctg aga aac<br>Leu Pro Gln Val Tyr Thr Ala Thr Gly Thr Lys Asn Phe Leu Arg Asn<br>              1140                    1145                  1150 | | 3456 |
| att ttt cac caa agc act gag ccc agt gta gaa ggg ttt gat ggg ggg<br>Ile Phe His Gln Ser Thr Glu Pro Ser Val Glu Gly Phe Asp Gly Gly | | 3504 |

-continued

| | |
|---|---|
| tca cat gcg ccg gtg cct caa gac agc agg tca tta aat gat tcg gca<br>Ser His Ala Pro Val Pro Gln Asp Ser Arg Ser Leu Asn Asp Ser Ala<br>　　　1170　　　　　　　　　1175　　　　　　　　1180 | 3552 |
| gag aga gca gag act cac ata gcc cat ttc tca gca att agg gaa gag<br>Glu Arg Ala Glu Thr His Ile Ala His Phe Ser Ala Ile Arg Glu Glu<br>1185　　　　　　　　1190　　　　　　　　1195　　　　　　　　1200 | 3600 |
| gca ccc ttg gaa gcc ccg gga aat cga aca ggt cca ggt ccg agg agt<br>Ala Pro Leu Glu Ala Pro Gly Asn Arg Thr Gly Pro Gly Pro Arg Ser<br>　　　　　　　　1205　　　　　　　　1210　　　　　　　　1215 | 3648 |
| gcg gtt ccc cgc cgc gtt aag cag agc ttg aaa cag atc aga ctc ccg<br>Ala Val Pro Arg Arg Val Lys Gln Ser Leu Lys Gln Ile Arg Leu Pro<br>　　　1220　　　　　　　　1225　　　　　　　　1230 | 3696 |
| cta gaa gaa ata aag cct gaa agg ggg gtg gtt ctg aat gcc acc tca<br>Leu Glu Glu Ile Lys Pro Glu Arg Gly Val Val Leu Asn Ala Thr Ser<br>1235　　　　　　　　1240　　　　　　　　1245 | 3744 |
| acc cgg tgg tct gaa agc agt cct atc tta caa gga gcc aaa aga aat<br>Thr Arg Trp Ser Glu Ser Ser Pro Ile Leu Gln Gly Ala Lys Arg Asn<br>　　　1250　　　　　　　　1255　　　　　　　　1260 | 3792 |
| aac ctt tct tta cct ttc ctg acc ttg gaa atg gcc gga ggt caa gga<br>Asn Leu Ser Leu Pro Phe Leu Thr Leu Glu Met Ala Gly Gly Gln Gly<br>1265　　　　　　　　1270　　　　　　　　1275　　　　　　　　1280 | 3840 |
| aag atc agc gcc ctg ggg aaa agt gcc gca ggc ccg ctg gcg tcc ggg<br>Lys Ile Ser Ala Leu Gly Lys Ser Ala Ala Gly Pro Leu Ala Ser Gly<br>　　　　　　　　1285　　　　　　　　1290　　　　　　　　1295 | 3888 |
| aag ctg gag aag gct gtt ctc tct tca gca ggc ttg tct gaa gca tct<br>Lys Leu Glu Lys Ala Val Leu Ser Ser Ala Gly Leu Ser Glu Ala Ser<br>　　　1300　　　　　　　　1305　　　　　　　　1310 | 3936 |
| ggc aaa gct gag ttt ctt cct aaa gtt cga gtt cat cgg gaa gac ctg<br>Gly Lys Ala Glu Phe Leu Pro Lys Val Arg Val His Arg Glu Asp Leu<br>1315　　　　　　　　1320　　　　　　　　1325 | 3984 |
| ttg cct caa aaa acc agc aat gtt tct tgc gca cac ggg gat ctc ggc<br>Leu Pro Gln Lys Thr Ser Asn Val Ser Cys Ala His Gly Asp Leu Gly<br>　　　1330　　　　　　　　1335　　　　　　　　1340 | 4032 |
| cag gag atc ttc ctg cag aaa aca cgg gga cct gtt aac ctg aac aaa<br>Gln Glu Ile Phe Leu Gln Lys Thr Arg Gly Pro Val Asn Leu Asn Lys<br>1345　　　　　　　　1350　　　　　　　　1355　　　　　　　　1360 | 4080 |
| gta aat aga cct gga agg act ccc tcc aag ctt ctg ggt ccc ccg atg<br>Val Asn Arg Pro Gly Arg Thr Pro Ser Lys Leu Leu Gly Pro Pro Met<br>　　　　　　　　1365　　　　　　　　1370　　　　　　　　1375 | 4128 |
| ccc aaa gag tgg gaa tcc cta gag aag tca cca aaa agc aca gct ctc<br>Pro Lys Glu Trp Glu Ser Leu Glu Lys Ser Pro Lys Ser Thr Ala Leu<br>　　　1380　　　　　　　　1385　　　　　　　　1390 | 4176 |
| agg acg aaa gac atc atc agt tta ccc ctg gac cgt cac gaa agc aat<br>Arg Thr Lys Asp Ile Ile Ser Leu Pro Leu Asp Arg His Glu Ser Asn<br>1395　　　　　　　　1400　　　　　　　　1405 | 4224 |
| cat tca ata gca gca aaa aat gaa gga caa gcc gag acc caa aga gaa<br>His Ser Ile Ala Ala Lys Asn Glu Gly Gln Ala Glu Thr Gln Arg Glu<br>　　　1410　　　　　　　　1415　　　　　　　　1420 | 4272 |
| gcc gcc tgg acg aag cag gga ggg cct gga agg ctg tgc gct cca aag<br>Ala Ala Trp Thr Lys Gln Gly Gly Pro Gly Arg Leu Cys Ala Pro Lys<br>1425　　　　　　　　1430　　　　　　　　1435　　　　　　　　1440 | 4320 |
| cct ccg gtc ctg cga cgg cat cag agg gac ata agc ctt cct act ttt<br>Pro Pro Val Leu Arg Arg His Gln Arg Asp Ile Ser Leu Pro Thr Phe<br>　　　　　　　　1445　　　　　　　　1450　　　　　　　　1455 | 4368 |
| cag ccg gag gaa gac aaa atg gac tat gat gat atc ttc tca act gaa<br>Gln Pro Glu Glu Asp Lys Met Asp Tyr Asp Asp Ile Phe Ser Thr Glu<br>　　　1460　　　　　　　　1465　　　　　　　　1470 | 4416 |
| acg aag gga gaa gat ttt gac att tac ggt gag gat gaa aat cag gac<br> | 4464 |

-continued

```
Thr Lys Gly Glu Asp Phe Asp Ile Tyr Gly Glu Asp Glu Asn Gln Asp
        1475                1480                1485 cct cgc agc ttt cag aag aga acc cga cac tat ttc att gct gcg gtg    4512
Pro Arg Ser Phe Gln Lys Arg Thr Arg His Tyr Phe Ile Ala Ala Val
        1490                1495                1500 gag cag ctc tgg gat tac ggg atg agc gaa tcc ccc cgg gcg cta aga    4560
Glu Gln Leu Trp Asp Tyr Gly Met Ser Glu Ser Pro Arg Ala Leu Arg
1505                1510                1515                1520 aac agg gct cag aac gga gag gtg cct cgg ttc aag aag gtg gtc ttc    4608
Asn Arg Ala Gln Asn Gly Glu Val Pro Arg Phe Lys Lys Val Val Phe
                1525                1530                1535 cgg gaa ttt gct gac ggc tcc ttc acg cag ccg tcg tac cgc ggg gaa    4656
Arg Glu Phe Ala Asp Gly Ser Phe Thr Gln Pro Ser Tyr Arg Gly Glu
        1540                1545                1550 ctc aac aaa cac ttg ggg ctc ttg gga ccc tac atc aga gcg gaa gtt    4704
Leu Asn Lys His Leu Gly Leu Leu Gly Pro Tyr Ile Arg Ala Glu Val
        1555                1560                1565 gaa gac aac atc atg gta act ttc aaa aac cag gcg tct cgt ccc tat    4752
Glu Asp Asn Ile Met Val Thr Phe Lys Asn Gln Ala Ser Arg Pro Tyr
1570                1575                1580 tcc ttc tac tcg agc ctt att tct tat ccg gat gat cag gag caa ggg    4800
Ser Phe Tyr Ser Ser Leu Ile Ser Tyr Pro Asp Asp Gln Glu Gln Gly
1585                1590                1595                1600 gca gaa cct cga cac aac ttc gtc cag cca aat gaa acc aga act tac    4848
Ala Glu Pro Arg His Asn Phe Val Gln Pro Asn Glu Thr Arg Thr Tyr
        1605                1610                1615 ttt tgg aaa gtg cag cat cac atg gca ccc aca gaa gac gag ttt gac    4896
Phe Trp Lys Val Gln His His Met Ala Pro Thr Glu Asp Glu Phe Asp
        1620                1625                1630 tgc aaa gcc tgg gcc tac ttt tct gat gtt gac ctg gaa aaa gat gtg    4944
Cys Lys Ala Trp Ala Tyr Phe Ser Asp Val Asp Leu Glu Lys Asp Val
        1635                1640                1645 cac tca ggc ttg atc ggc ccc ctt ctg atc tgc cgc gcc aac acc ctg    4992
His Ser Gly Leu Ile Gly Pro Leu Leu Ile Cys Arg Ala Asn Thr Leu
        1650                1655                1660 aac gct gct cac ggt aga caa gtg acc gtg caa gaa ttt gct ctg ttt    5040
Asn Ala Ala His Gly Arg Gln Val Thr Val Gln Glu Phe Ala Leu Phe
1665                1670                1675                1680 ttc act att ttt gat gag aca aag agc tgg tac ttc act gaa aat gtg    5088
Phe Thr Ile Phe Asp Glu Thr Lys Ser Trp Tyr Phe Thr Glu Asn Val
                1685                1690                1695 gaa agg aac tgc cgg gcc ccc tgc cac ctg cag atg gag gac ccc act    5136
Glu Arg Asn Cys Arg Ala Pro Cys His Leu Gln Met Glu Asp Pro Thr
                1700                1705                1710 ctg aaa gaa aac tat cgc ttc cat gca atc aat ggc tat gtg atg gat    5184
Leu Lys Glu Asn Tyr Arg Phe His Ala Ile Asn Gly Tyr Val Met Asp
        1715                1720                1725 aca ctc cct ggc tta gta atg gct cag aat caa agg atc cga tgg tat    5232
Thr Leu Pro Gly Leu Val Met Ala Gln Asn Gln Arg Ile Arg Trp Tyr
1730                1735                1740 ctg ctc agc atg ggc agc aat gaa aat atc cat tcg att cat ttt agc    5280
Leu Leu Ser Met Gly Ser Asn Glu Asn Ile His Ser Ile His Phe Ser
1745                1750                1755                1760 gga cac gtg ttc agt gta cgg aaa aag gag gag tat aaa atg gcc gtg    5328
Gly His Val Phe Ser Val Arg Lys Lys Glu Glu Tyr Lys Met Ala Val
                1765                1770                1775 tac aat ctc tat ccg ggt gtc ttt gag aca gtg gaa atg cta ccg tcc    5376
Tyr Asn Leu Tyr Pro Gly Val Phe Glu Thr Val Glu Met Leu Pro Ser
        1780                1785                1790
```

```
                                                    -continued
aaa gtt gga att tgg cga ata gaa tgc ctg att ggc gag cac ctg caa    5424
Lys Val Gly Ile Trp Arg Ile Glu Cys Leu Ile Gly Glu His Leu Gln
        1795                1800                1805 gct ggg atg agc acg act ttc ctg gtg tac agc aag gag tgt cag gct    5472
Ala Gly Met Ser Thr Thr Phe Leu Val Tyr Ser Lys Glu Cys Gln Ala
    1810                1815                1820 cca ctg gga atg gct tct gga cgc att aga gat ttt cag atc aca gct    5520
Pro Leu Gly Met Ala Ser Gly Arg Ile Arg Asp Phe Gln Ile Thr Ala
1825                1830                1835                1840 tca gga cag tat gga cag tgg gcc cca aag ctg gcc aga ctt cat tat    5568
Ser Gly Gln Tyr Gly Gln Trp Ala Pro Lys Leu Ala Arg Leu His Tyr
            1845                1850                1855 tcc gga tca atc aat gcc tgg agc acc aag gat ccc cac tcc tgg atc    5616
Ser Gly Ser Ile Asn Ala Trp Ser Thr Lys Asp Pro His Ser Trp Ile
        1860                1865                1870 aag gtg gat ctg ttg gca cca atg atc att cac ggc atc atg acc cag    5664
Lys Val Asp Leu Leu Ala Pro Met Ile Ile His Gly Ile Met Thr Gln
    1875                1880                1885 ggt gcc cgt cag aag ttt tcc agc ctc tac atc tcc cag ttt atc atc    5712
Gly Ala Arg Gln Lys Phe Ser Ser Leu Tyr Ile Ser Gln Phe Ile Ile
1890                1895                1900 atg tac agt ctt gac ggg agg aac tgg cag agt tac cga ggg aat tcc    5760
Met Tyr Ser Leu Asp Gly Arg Asn Trp Gln Ser Tyr Arg Gly Asn Ser
1905                1910                1915                1920 acg ggc acc tta atg gtc ttc ttt ggc aat gtg gac gca tct ggg att    5808
Thr Gly Thr Leu Met Val Phe Phe Gly Asn Val Asp Ala Ser Gly Ile
            1925                1930                1935 aaa cac aat att ttt aac cct ccg att gtg gct cgg tac atc cgt ttg    5856
Lys His Asn Ile Phe Asn Pro Pro Ile Val Ala Arg Tyr Ile Arg Leu
        1940                1945                1950 cac cca aca cat tac agc atc cgc agc act ctt cgc atg gag ttg atg    5904
His Pro Thr His Tyr Ser Ile Arg Ser Thr Leu Arg Met Glu Leu Met
    1955                1960                1965 ggc tgt gat tta aac agt tgc agc atg ccc ctg gga atg cag aat aaa    5952
Gly Cys Asp Leu Asn Ser Cys Ser Met Pro Leu Gly Met Gln Asn Lys
1970                1975                1980 gcg ata tca gac tca cag atc acg gcc tcc tcc cac cta agc aat ata    6000
Ala Ile Ser Asp Ser Gln Ile Thr Ala Ser Ser His Leu Ser Asn Ile
1985                1990                1995                2000 ttt gcc acc tgg tct cct tca caa gcc cga ctt cac ctc cag ggg cgg    6048
Phe Ala Thr Trp Ser Pro Ser Gln Ala Arg Leu His Leu Gln Gly Arg
            2005                2010                2015 acg aat gcc tgg cga ccc cgg gtg agc agc gca gag gag tgg ctg cag    6096
Thr Asn Ala Trp Arg Pro Arg Val Ser Ser Ala Glu Glu Trp Leu Gln
        2020                2025                2030 gtg gac ctg cag aag acg gtg aag gtc aca ggc atc acc acc cag ggc    6144
Val Asp Leu Gln Lys Thr Val Lys Val Thr Gly Ile Thr Thr Gln Gly
    2035                2040                2045 gtg aag tcc ctg ctc agc agc atg tat gtg aag gag ttc ctc gtg tcc    6192
Val Lys Ser Leu Leu Ser Ser Met Tyr Val Lys Glu Phe Leu Val Ser
2050                2055                2060 agt agt cag gac ggc cgc cgc tgg acc ctg ttt ctt cag gac ggc cac    6240
Ser Ser Gln Asp Gly Arg Arg Trp Thr Leu Phe Leu Gln Asp Gly His
2065                2070                2075                2080 acg aag gtt ttt cag ggc aat cag gac tcc tcc acc ccc gtg gtg aac    6288
Thr Lys Val Phe Gln Gly Asn Gln Asp Ser Ser Thr Pro Val Val Asn
            2085                2090                2095 gct ctg gac ccc ccg ctg ttc acg cgc tac ctg agg atc cac ccc acg    6336
Ala Leu Asp Pro Pro Leu Phe Thr Arg Tyr Leu Arg Ile His Pro Thr
        2100                2105                2110
```

-continued

```
agc tgg gcg cag cac atc gcc ctg agg ctc gag gtt cta gga tgt gag        6384
Ser Trp Ala Gln His Ile Ala Leu Arg Leu Glu Val Leu Gly Cys Glu
    2115                2120                2125 gca cag gat ctc tac tga                                                 6402
Ala Gln Asp Leu Tyr
    2130
```

<210> SEQ ID NO 37
<211> LENGTH: 2133
<212> TYPE: PRT
<213> ORGANISM: Sus scrofa

<400> SEQUENCE: 37

```
Met Gln Leu Glu Leu Ser Thr Cys Val Phe Leu Cys Leu Leu Pro Leu
  1               5                  10                  15

Gly Phe Ser Ala Ile Arg Arg Tyr Tyr Leu Gly Ala Val Glu Leu Ser
              20                  25                  30

Trp Asp Tyr Arg Gln Ser Glu Leu Leu Arg Glu Leu His Val Asp Thr
          35                  40                  45

Arg Phe Pro Ala Thr Ala Pro Gly Ala Leu Pro Leu Gly Pro Ser Val
      50                  55                  60

Leu Tyr Lys Lys Thr Val Phe Val Glu Phe Thr Asp Gln Leu Phe Ser
 65                  70                  75                  80

Val Ala Arg Pro Arg Pro Pro Trp Met Gly Leu Leu Gly Pro Thr Ile
                  85                  90                  95

Gln Ala Glu Val Tyr Asp Thr Val Val Thr Leu Lys Asn Met Ala
             100                 105                 110

Ser His Pro Val Ser Leu His Ala Val Gly Val Ser Phe Trp Lys Ser
         115                 120                 125

Ser Glu Gly Ala Glu Tyr Glu Asp His Thr Ser Gln Arg Glu Lys Glu
     130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335
```

```
His Gly Gly Met Glu Ala His Val Arg Val Glu Ser Cys Ala Glu Glu
            340                 345                 350

Pro Gln Leu Arg Arg Lys Ala Asp Glu Glu Asp Tyr Asp Asp Asn
            355                 360             365

Leu Tyr Asp Ser Asp Met Asp Val Val Arg Leu Asp Gly Asp Val
            370             375                 380

Ser Pro Phe Ile Gln Ile Arg Ser Val Ala Lys Lys His Pro Lys Thr
385                 390                 395                 400

Trp Val His Tyr Ile Ser Ala Glu Glu Asp Trp Asp Tyr Ala Pro
            405                 410                 415

Ala Val Pro Ser Pro Ser Asp Arg Ser Tyr Lys Ser Leu Tyr Leu Asn
            420                 425                 430

Ser Gly Pro Gln Arg Ile Gly Arg Lys Tyr Lys Lys Ala Arg Phe Val
            435                 440                 445

Ala Tyr Thr Asp Val Thr Phe Lys Thr Arg Lys Ala Ile Pro Tyr Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Lys Ala Ser Arg Pro Tyr Asn Ile Tyr Pro
            485                 490                 495

His Gly Ile Thr Asp Val Ser Ala Leu His Pro Gly Arg Leu Leu Lys
            500                 505                 510

Gly Trp Lys His Leu Lys Asp Met Pro Ile Leu Pro Gly Glu Thr Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Ser Ile Asn Leu Glu Lys
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Met Met Ser Asp Lys Arg Asn Val
            580                 585                 590

Ile Leu Phe Ser Val Phe Asp Glu Asn Gln Ser Trp Tyr Leu Ala Glu
            595                 600                 605

Asn Ile Gln Arg Phe Leu Pro Asn Pro Asp Gly Leu Gln Pro Gln Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Val Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
            725                 730                 735

Tyr Tyr Asp Asn Thr Tyr Glu Asp Ile Pro Gly Phe Leu Leu Ser Gly
            740                 745                 750
```

-continued

```
Lys Asn Val Ile Glu Pro Arg Ser Phe Ala Gln Asn Ser Arg Pro Pro
            755                 760                 765
Ser Ala Ser Gln Lys Gln Phe Gln Thr Ile Thr Ser Pro Glu Asp Asp
        770                 775                 780
Val Glu Leu Asp Pro Gln Ser Gly Glu Arg Thr Gln Ala Leu Glu Glu
785                 790                 795                 800
Leu Ser Val Pro Ser Gly Asp Gly Ser Met Leu Leu Gly Gln Asn Pro
                805                 810                 815
Ala Pro His Gly Ser Ser Ser Asp Leu Gln Glu Ala Arg Asn Glu
            820                 825                 830
Ala Asp Asp Tyr Leu Pro Gly Ala Arg Glu Arg Asn Thr Ala Pro Ser
            835                 840                 845
Ala Ala Ala Arg Leu Arg Pro Glu Leu His His Ser Ala Glu Arg Val
        850                 855                 860
Leu Thr Pro Glu Pro Glu Lys Glu Leu Lys Lys Leu Asp Ser Lys Met
865                 870                 875                 880
Ser Ser Ser Ser Asp Leu Leu Lys Thr Ser Pro Thr Ile Pro Ser Asp
                885                 890                 895
Thr Leu Ser Ala Glu Thr Glu Arg Thr His Ser Leu Gly Pro Pro His
            900                 905                 910
Pro Gln Val Asn Phe Arg Ser Gln Leu Gly Ala Ile Val Leu Gly Lys
            915                 920                 925
Asn Ser Ser His Phe Ile Gly Ala Gly Val Pro Leu Gly Ser Thr Glu
        930                 935                 940
Glu Asp His Glu Ser Ser Leu Gly Glu Asn Val Ser Pro Val Glu Ser
945                 950                 955                 960
Asp Gly Ile Phe Glu Lys Glu Arg Ala His Gly Pro Ala Ser Leu Thr
                965                 970                 975
Lys Asp Asp Val Leu Phe Lys Val Asn Ile Ser Leu Val Lys Thr Asn
            980                 985                 990
Lys Ala Arg Val Tyr Leu Lys Thr Asn Arg Lys Ile His Ile Asp Asp
            995                1000                1005
Ala Ala Leu Leu Thr Glu Asn Arg Ala Ser Ala Thr Phe Met Asp Lys
        1010                1015                1020
Asn Thr Thr Ala Ser Gly Leu Asn His Val Ser Asn Trp Ile Lys Gly
1025                1030                1035                1040
Pro Leu Gly Lys Asn Pro Leu Ser Ser Glu Arg Gly Pro Ser Pro Glu
                1045                1050                1055
Leu Leu Thr Ser Ser Gly Ser Gly Lys Ser Val Lys Gly Gln Ser Ser
            1060                1065                1070
Gly Gln Gly Arg Ile Arg Val Ala Val Glu Glu Glu Leu Ser Lys
            1075                1080                1085
Gly Lys Glu Met Met Leu Pro Asn Ser Glu Leu Thr Phe Leu Thr Asn
        1090                1095                1100
Ser Ala Asp Val Gln Gly Asn Asp Thr His Ser Gln Gly Lys Lys Ser
1105                1110                1115                1120
Arg Glu Glu Met Glu Arg Arg Glu Lys Leu Val Gln Glu Lys Val Asp
                1125                1130                1135
Leu Pro Gln Val Tyr Thr Ala Thr Gly Thr Lys Asn Phe Leu Arg Asn
            1140                1145                1150
Ile Phe His Gln Ser Thr Glu Pro Ser Val Glu Gly Phe Asp Gly Gly
            1155                1160                1165
Ser His Ala Pro Val Pro Gln Asp Ser Arg Ser Leu Asn Asp Ser Ala
```

-continued

```
            1170                1175                1180
Glu Arg Ala Glu Thr His Ile Ala His Phe Ser Ala Ile Arg Glu Glu
1185                1190                1195                1200
Ala Pro Leu Glu Ala Pro Gly Asn Arg Thr Gly Pro Gly Pro Arg Ser
                1205                1210                1215
Ala Val Pro Arg Arg Val Lys Gln Ser Leu Lys Gln Ile Arg Leu Pro
                1220                1225                1230
Leu Glu Glu Ile Lys Pro Glu Arg Gly Val Val Leu Asn Ala Thr Ser
            1235                1240                1245
Thr Arg Trp Ser Glu Ser Ser Pro Ile Leu Gln Gly Ala Lys Arg Asn
    1250                1255                1260
Asn Leu Ser Leu Pro Phe Leu Thr Leu Glu Met Ala Gly Gly Gln Gly
1265                1270                1275                1280
Lys Ile Ser Ala Leu Gly Lys Ser Ala Ala Gly Pro Leu Ala Ser Gly
                1285                1290                1295
Lys Leu Glu Lys Ala Val Leu Ser Ser Ala Gly Leu Ser Glu Ala Ser
                1300                1305                1310
Gly Lys Ala Glu Phe Leu Pro Lys Val Arg Val His Arg Glu Asp Leu
        1315                1320                1325
Leu Pro Gln Lys Thr Ser Asn Val Ser Cys Ala His Gly Asp Leu Gly
        1330                1335                1340
Gln Glu Ile Phe Leu Gln Lys Thr Arg Gly Pro Val Asn Leu Asn Lys
1345                1350                1355                1360
Val Asn Arg Pro Gly Arg Thr Pro Ser Lys Leu Leu Gly Pro Pro Met
                1365                1370                1375
Pro Lys Glu Trp Glu Ser Leu Glu Lys Ser Pro Lys Ser Thr Ala Leu
                1380                1385                1390
Arg Thr Lys Asp Ile Ile Ser Leu Pro Leu Asp Arg His Glu Ser Asn
        1395                1400                1405
His Ser Ile Ala Ala Lys Asn Glu Gly Gln Ala Glu Thr Gln Arg Glu
        1410                1415                1420
Ala Ala Trp Thr Lys Gln Gly Gly Pro Gly Arg Leu Cys Ala Pro Lys
1425                1430                1435                1440
Pro Pro Val Leu Arg Arg His Gln Arg Asp Ile Ser Leu Pro Thr Phe
                1445                1450                1455
Gln Pro Glu Glu Asp Lys Met Asp Tyr Asp Asp Ile Phe Ser Thr Glu
                1460                1465                1470
Thr Lys Gly Glu Asp Phe Asp Ile Tyr Gly Glu Asp Glu Asn Gln Asp
        1475                1480                1485
Pro Arg Ser Phe Gln Lys Arg Thr Arg His Tyr Phe Ile Ala Ala Val
        1490                1495                1500
Glu Gln Leu Trp Asp Tyr Gly Met Ser Glu Ser Pro Arg Ala Leu Arg
1505                1510                1515                1520
Asn Arg Ala Gln Asn Gly Glu Val Pro Arg Phe Lys Lys Val Val Phe
                1525                1530                1535
Arg Glu Phe Ala Asp Gly Ser Phe Thr Gln Pro Ser Tyr Arg Gly Glu
                1540                1545                1550
Leu Asn Lys His Leu Gly Leu Leu Gly Pro Tyr Ile Arg Ala Glu Val
        1555                1560                1565
Glu Asp Asn Ile Met Val Thr Phe Lys Asn Gln Ala Ser Arg Pro Tyr
        1570                1575                1580
Ser Phe Tyr Ser Ser Leu Ile Ser Tyr Pro Asp Asp Gln Glu Gln Gly
1585                1590                1595                1600
```

```
Ala Glu Pro Arg His Asn Phe Val Gln Pro Asn Glu Thr Arg Thr Tyr
            1605                1610                1615

Phe Trp Lys Val Gln His His Met Ala Pro Thr Glu Asp Glu Phe Asp
        1620                1625                1630

Cys Lys Ala Trp Ala Tyr Phe Ser Asp Val Asp Leu Glu Lys Asp Val
            1635                1640                1645

His Ser Gly Leu Ile Gly Pro Leu Leu Ile Cys Arg Ala Asn Thr Leu
        1650                1655                1660

Asn Ala Ala His Gly Arg Gln Val Thr Val Gln Glu Phe Ala Leu Phe
1665                1670                1675                1680

Phe Thr Ile Phe Asp Glu Thr Lys Ser Trp Tyr Phe Thr Glu Asn Val
            1685                1690                1695

Glu Arg Asn Cys Arg Ala Pro Cys His Leu Gln Met Glu Asp Pro Thr
        1700                1705                1710

Leu Lys Glu Asn Tyr Arg Phe His Ala Ile Asn Gly Tyr Val Met Asp
            1715                1720                1725

Thr Leu Pro Gly Leu Val Met Ala Gln Asn Gln Arg Ile Arg Trp Tyr
        1730                1735                1740

Leu Leu Ser Met Gly Ser Asn Glu Asn Ile His Ser Ile His Phe Ser
1745                1750                1755                1760

Gly His Val Phe Ser Val Arg Lys Lys Glu Glu Tyr Lys Met Ala Val
            1765                1770                1775

Tyr Asn Leu Tyr Pro Gly Val Phe Glu Thr Val Glu Met Leu Pro Ser
        1780                1785                1790

Lys Val Gly Ile Trp Arg Ile Glu Cys Leu Ile Gly Glu His Leu Gln
            1795                1800                1805

Ala Gly Met Ser Thr Thr Phe Leu Val Tyr Ser Lys Glu Cys Gln Ala
        1810                1815                1820

Pro Leu Gly Met Ala Ser Gly Arg Ile Arg Asp Phe Gln Ile Thr Ala
1825                1830                1835                1840

Ser Gly Gln Tyr Gly Gln Trp Ala Pro Lys Leu Ala Arg Leu His Tyr
            1845                1850                1855

Ser Gly Ser Ile Asn Ala Trp Ser Thr Lys Asp Pro His Ser Trp Ile
        1860                1865                1870

Lys Val Asp Leu Leu Ala Pro Met Ile Ile His Gly Ile Met Thr Gln
            1875                1880                1885

Gly Ala Arg Gln Lys Phe Ser Ser Leu Tyr Ile Ser Gln Phe Ile Ile
        1890                1895                1900

Met Tyr Ser Leu Asp Gly Arg Asn Trp Gln Ser Tyr Arg Gly Asn Ser
1905                1910                1915                1920

Thr Gly Thr Leu Met Val Phe Phe Gly Asn Val Asp Ala Ser Gly Ile
            1925                1930                1935

Lys His Asn Ile Phe Asn Pro Pro Ile Val Ala Arg Tyr Ile Arg Leu
        1940                1945                1950

His Pro Thr His Tyr Ser Ile Arg Ser Thr Leu Arg Met Glu Leu Met
        1955                1960                1965

Gly Cys Asp Leu Asn Ser Cys Ser Met Pro Leu Gly Met Gln Asn Lys
    1970                1975                1980

Ala Ile Ser Asp Ser Gln Ile Thr Ala Ser Ser His Leu Ser Asn Ile
1985                1990                1995                2000

Phe Ala Thr Trp Ser Pro Ser Gln Ala Arg Leu His Leu Gln Gly Arg
            2005                2010                2015
```

-continued

```
Thr Asn Ala Trp Arg Pro Arg Val Ser Ser Ala Glu Glu Trp Leu Gln
        2020                2025                2030

Val Asp Leu Gln Lys Thr Val Lys Val Thr Gly Ile Thr Thr Gln Gly
        2035                2040            2045

Val Lys Ser Leu Leu Ser Ser Met Tyr Val Lys Glu Phe Leu Val Ser
        2050                2055                2060

Ser Ser Gln Asp Gly Arg Arg Trp Thr Leu Phe Leu Gln Asp Gly His
2065            2070                2075                2080

Thr Lys Val Phe Gln Gly Asn Gln Asp Ser Ser Thr Pro Val Val Asn
                2085                2090                2095

Ala Leu Asp Pro Pro Leu Phe Thr Arg Tyr Leu Arg Ile His Pro Thr
            2100                2105                2110

Ser Trp Ala Gln His Ile Ala Leu Arg Leu Glu Val Leu Gly Cys Glu
        2115                2120                2125

Ala Gln Asp Leu Tyr
    2130

<210> SEQ ID NO 38
<211> LENGTH: 4334
<212> TYPE: DNA
<213> ORGANISM: Artificial Sequence
<220> FEATURE:
<223> OTHER INFORMATION: Description of Artificial Sequence:factor VIII
      lacking the B domain
<220> FEATURE:
<221> NAME/KEY: CDS
<222> LOCATION: (3)..(4331)

<400> SEQUENCE: 38 ga atg cag cta gag ctc tcc acc tgt gtc ttt ctg tgt ctc ttg cca       47
   Met Gln Leu Glu Leu Ser Thr Cys Val Phe Leu Cys Leu Leu Pro
   1               5                   10                  15 ctc ggc ttt agt gcc atc agg aga tac tac ctg ggc gca gtg gaa ctg      95
Leu Gly Phe Ser Ala Ile Arg Arg Tyr Tyr Leu Gly Ala Val Glu Leu
            20                  25                  30 tcc tgg gac tac cgg caa agt gaa ctc ctc cgt gag ctg cac gtg gac     143
Ser Trp Asp Tyr Arg Gln Ser Glu Leu Leu Arg Glu Leu His Val Asp
        35                  40                  45 acc aga ttt cct gct aca gcg cca gga gct ctt ccg ttg ggc ccg tca     191
Thr Arg Phe Pro Ala Thr Ala Pro Gly Ala Leu Pro Leu Gly Pro Ser
    50                  55                  60 gtc ctg tac aaa aag act gtg ttc gta gag ttc acg gat caa ctt ttc     239
Val Leu Tyr Lys Lys Thr Val Phe Val Glu Phe Thr Asp Gln Leu Phe
65                  70                  75 agc gtt gcc agg ccc agg cca cca tgg atg ggt ctg ctg ggt cct acc     287
Ser Val Ala Arg Pro Arg Pro Pro Trp Met Gly Leu Leu Gly Pro Thr
80                  85                  90                  95 atc cag gct gag gtt tac gac acg gtg gtc gtt acc ctg aag aac atg     335
Ile Gln Ala Glu Val Tyr Asp Thr Val Val Val Thr Leu Lys Asn Met
                100                 105                 110 gct tct cat ccc gtt agt ctt cac gct gtc ggc gtc tcc ttc tgg aaa     383
Ala Ser His Pro Val Ser Leu His Ala Val Gly Val Ser Phe Trp Lys
            115                 120                 125 tct tcc gaa ggc gct gaa tat gag gat cac acc agc caa agg gag aag     431
Ser Ser Glu Gly Ala Glu Tyr Glu Asp His Thr Ser Gln Arg Glu Lys
        130                 135                 140 gaa gac gat aaa gtc ctt ccc ggt aaa agc caa acc tac gtc tgg cag     479
Glu Asp Asp Lys Val Leu Pro Gly Lys Ser Gln Thr Tyr Val Trp Gln
    145                 150                 155 gtc ctg aaa gaa aat ggt cca aca gcc tct gac cca cca tgt ctc acc     527
```

```
                                                  -continued

Val Leu Lys Glu Asn Gly Pro Thr Ala Ser Asp Pro Pro Cys Leu Thr
160             165                 170                 175 tac tca tac ctg tct cac gtg gac ctg gtg aaa gac ctg aat tcg ggc          575
Tyr Ser Tyr Leu Ser His Val Asp Leu Val Lys Asp Leu Asn Ser Gly
                180                 185                 190 ctc att gga gcc ctg ctg gtt tgt aga gaa ggg agt ctg acc aga gaa          623
Leu Ile Gly Ala Leu Leu Val Cys Arg Glu Gly Ser Leu Thr Arg Glu
            195                 200                 205 agg acc cag aac ctg cac gaa ttt gta cta ctt ttt gct gtc ttt gat          671
Arg Thr Gln Asn Leu His Glu Phe Val Leu Leu Phe Ala Val Phe Asp
        210                 215                 220 gaa ggg aaa agt tgg cac tca gca aga aat gac tcc tgg aca cgg gcc          719
Glu Gly Lys Ser Trp His Ser Ala Arg Asn Asp Ser Trp Thr Arg Ala
    225                 230                 235 atg gat ccc gca cct gcc agg gcc cag cct gca atg cac aca gtc aat          767
Met Asp Pro Ala Pro Ala Arg Ala Gln Pro Ala Met His Thr Val Asn
240                 245                 250                 255 ggc tat gtc aac agg tct ctg cca ggt ctg atc gga tgt cat aag aaa          815
Gly Tyr Val Asn Arg Ser Leu Pro Gly Leu Ile Gly Cys His Lys Lys
                260                 265                 270 tca gtc tac tgg cac gtg att gga atg ggc acc agc ccg gaa gtg cac          863
Ser Val Tyr Trp His Val Ile Gly Met Gly Thr Ser Pro Glu Val His
            275                 280                 285 tcc att ttt ctt gaa ggc cac acg ttt ctc gtg agg cac cat cgc cag          911
Ser Ile Phe Leu Glu Gly His Thr Phe Leu Val Arg His His Arg Gln
        290                 295                 300 gct tcc ttg gag atc tcg cca cta act ttc ctc act gct cag aca ttc          959
Ala Ser Leu Glu Ile Ser Pro Leu Thr Phe Leu Thr Ala Gln Thr Phe
    305                 310                 315 ctg atg gac ctt ggc cag ttc cta ctg ttt tgt cat atc tct tcc cac         1007
Leu Met Asp Leu Gly Gln Phe Leu Leu Phe Cys His Ile Ser Ser His
320                 325                 330                 335 cac cat ggt ggc atg gag gct cac gtc aga gta gaa agc tgc gcc gag         1055
His His Gly Gly Met Glu Ala His Val Arg Val Glu Ser Cys Ala Glu
                340                 345                 350 gag ccc cag ctg cgg agg aaa gct gat gaa gag gaa gat tat gat gac         1103
Glu Pro Gln Leu Arg Arg Lys Ala Asp Glu Glu Glu Asp Tyr Asp Asp
            355                 360                 365 aat ttg tac gac tcg gac atg gac gtg gtc cgg ctc gat ggt gac gac         1151
Asn Leu Tyr Asp Ser Asp Met Asp Val Val Arg Leu Asp Gly Asp Asp
        370                 375                 380 gtg tct ccc ttt atc caa atc cgc tcg gtt gcc aag aag cat ccc aaa         1199
Val Ser Pro Phe Ile Gln Ile Arg Ser Val Ala Lys Lys His Pro Lys
    385                 390                 395 acc tgg gtg cac tac atc tct gca gag gag gag gac tgg gac tac gcc         1247
Thr Trp Val His Tyr Ile Ser Ala Glu Glu Glu Asp Trp Asp Tyr Ala
400                 405                 410                 415 ccc gcg gtc ccc agc ccc agt gac aga agt tat aaa agt ctc tac ttg         1295
Pro Ala Val Pro Ser Pro Ser Asp Arg Ser Tyr Lys Ser Leu Tyr Leu
                420                 425                 430 aac agt ggt cct cag cga att ggt agg aaa tac aaa aaa gct cga ttc         1343
Asn Ser Gly Pro Gln Arg Ile Gly Arg Lys Tyr Lys Lys Ala Arg Phe
            435                 440                 445 gtc gct tac acg gat gta aca ttt aag act cgt aaa gct att ccg tat         1391
Val Ala Tyr Thr Asp Val Thr Phe Lys Thr Arg Lys Ala Ile Pro Tyr
        450                 455                 460 gaa tca gga atc ctg gga cct tta ctt tat gga gaa gtt gga gac aca         1439
Glu Ser Gly Ile Leu Gly Pro Leu Leu Tyr Gly Glu Val Gly Asp Thr
    465                 470                 475
```

```
ctt ttg att ata ttt aag aat aaa gcg agc cga cca tat aac atc tac      1487
Leu Leu Ile Ile Phe Lys Asn Lys Ala Ser Arg Pro Tyr Asn Ile Tyr
480                 485                 490                 495 cct cat gga atc act gat gtc agc gct ttg cac cca ggg aga ctt cta      1535
Pro His Gly Ile Thr Asp Val Ser Ala Leu His Pro Gly Arg Leu Leu
                500                 505                 510 aaa ggt tgg aaa cat ttg aaa gac atg cca att ctg cca gga gag act      1583
Lys Gly Trp Lys His Leu Lys Asp Met Pro Ile Leu Pro Gly Glu Thr
            515                 520                 525 ttc aag tat aaa tgg aca gtg act gtg gaa gat ggg cca acc aag tcc      1631
Phe Lys Tyr Lys Trp Thr Val Thr Val Glu Asp Gly Pro Thr Lys Ser
        530                 535                 540 gat cct cgg tgc ctg acc cgc tac tac tcg agc tcc att aat cta gag      1679
Asp Pro Arg Cys Leu Thr Arg Tyr Tyr Ser Ser Ser Ile Asn Leu Glu
545                 550                 555 aaa gat ctg gct tcg gga ctc att ggc cct ctc ctc atc tgc tac aaa      1727
Lys Asp Leu Ala Ser Gly Leu Ile Gly Pro Leu Leu Ile Cys Tyr Lys
560                 565                 570                 575 gaa tct gta gac caa aga gga aac cag atg atg tca gac aag aga aac      1775
Glu Ser Val Asp Gln Arg Gly Asn Gln Met Met Ser Asp Lys Arg Asn
                580                 585                 590 gtc atc ctg ttt tct gta ttc gat gag aat caa agc tgg tac ctc gca      1823
Val Ile Leu Phe Ser Val Phe Asp Glu Asn Gln Ser Trp Tyr Leu Ala
            595                 600                 605 gag aat att cag cgc ttc ctc ccc aat ccg gat gga tta cag ccc cag      1871
Glu Asn Ile Gln Arg Phe Leu Pro Asn Pro Asp Gly Leu Gln Pro Gln
        610                 615                 620 gat cca gag ttc caa gct tct aac atc atg cac agc atc aat ggc tat      1919
Asp Pro Glu Phe Gln Ala Ser Asn Ile Met His Ser Ile Asn Gly Tyr
625                 630                 635 gtt ttt gat agc ttg cag ctg tcg gtt tgt ttg cac gag gtg gca tac      1967
Val Phe Asp Ser Leu Gln Leu Ser Val Cys Leu His Glu Val Ala Tyr
640                 645                 650                 655 tgg tac att cta agt gtt gga gca cag acg gac ttc ctc tcc gtc ttc      2015
Trp Tyr Ile Leu Ser Val Gly Ala Gln Thr Asp Phe Leu Ser Val Phe
                660                 665                 670 ttc tct ggc tac acc ttc aaa cac aaa atg gtc tat gaa gac aca ctc      2063
Phe Ser Gly Tyr Thr Phe Lys His Lys Met Val Tyr Glu Asp Thr Leu
            675                 680                 685 acc ctg ttc ccc ttc tca gga gaa acg gtc ttc atg tca atg gaa aac      2111
Thr Leu Phe Pro Phe Ser Gly Glu Thr Val Phe Met Ser Met Glu Asn
        690                 695                 700 cca ggt ctc tgg gtc cta ggg tgc cac aac tca gac ttg cgg aac aga      2159
Pro Gly Leu Trp Val Leu Gly Cys His Asn Ser Asp Leu Arg Asn Arg
705                 710                 715 ggg atg aca gcc tta ctg aag gtg tat agt tgt gac agg gac att ggt      2207
Gly Met Thr Ala Leu Leu Lys Val Tyr Ser Cys Asp Arg Asp Ile Gly
720                 725                 730                 735 gat tat tat gac aac act tat gaa gat att cca ggc ttc ttg ctg agt      2255
Asp Tyr Tyr Asp Asn Thr Tyr Glu Asp Ile Pro Gly Phe Leu Leu Ser
                740                 745                 750 gga aag aat gtc att gaa ccc aga gac ata agc ctt cct act ttt cag      2303
Gly Lys Asn Val Ile Glu Pro Arg Asp Ile Ser Leu Pro Thr Phe Gln
            755                 760                 765 ccg gag gaa gac aaa atg gac tat gat gat atc ttc tca act gaa acg      2351
Pro Glu Glu Asp Lys Met Asp Tyr Asp Asp Ile Phe Ser Thr Glu Thr
        770                 775                 780 aag gga gaa gat ttt gac att tac ggt gag gat gaa aat cag gac cct      2399
Lys Gly Glu Asp Phe Asp Ile Tyr Gly Glu Asp Glu Asn Gln Asp Pro
785                 790                 795
```

```
cgc agc ttt cag aag aga acc cga cac tat ttc att gct gcg gtg gag      2447
Arg Ser Phe Gln Lys Arg Thr Arg His Tyr Phe Ile Ala Ala Val Glu
800                 805                 810                 815 cag ctc tgg gat tac ggg atg agc gaa tcc ccc cgg gcg cta aga aac      2495
Gln Leu Trp Asp Tyr Gly Met Ser Glu Ser Pro Arg Ala Leu Arg Asn
                820                 825                 830 agg gct cag aac gga gag gtg cct cgg ttc aag aag gtg gtc ttc cgg      2543
Arg Ala Gln Asn Gly Glu Val Pro Arg Phe Lys Lys Val Val Phe Arg
835                 840                 845 gaa ttt gct gac ggc tcc ttc acg cag ccg tcg tac cgc ggg gaa ctc      2591
Glu Phe Ala Asp Gly Ser Phe Thr Gln Pro Ser Tyr Arg Gly Glu Leu
    850                 855                 860 aac aaa cac ttg ggg ctc ttg gga ccc tac atc aga gcg gaa gtt gaa      2639
Asn Lys His Leu Gly Leu Leu Gly Pro Tyr Ile Arg Ala Glu Val Glu
865                 870                 875 gac aac atc atg gta act ttc aaa aac cag gcg tct cgt ccc tat tcc      2687
Asp Asn Ile Met Val Thr Phe Lys Asn Gln Ala Ser Arg Pro Tyr Ser
880                 885                 890                 895 ttc tac tcg agc ctt att tct tat ccg gat gat cag gag caa ggg gca      2735
Phe Tyr Ser Ser Leu Ile Ser Tyr Pro Asp Asp Gln Glu Gln Gly Ala
                900                 905                 910 gaa cct cga cac aac ttc gtc cag cca aat gaa acc aga act tac ttt      2783
Glu Pro Arg His Asn Phe Val Gln Pro Asn Glu Thr Arg Thr Tyr Phe
            915                 920                 925 tgg aaa gtg cag cat cac atg gca ccc aca gaa gac gag ttt gac tgc      2831
Trp Lys Val Gln His His Met Ala Pro Thr Glu Asp Glu Phe Asp Cys
            930                 935                 940 aaa gcc tgg gcc tac ttt tct gat gtt gac ctg gaa aaa gat gtg cac      2879
Lys Ala Trp Ala Tyr Phe Ser Asp Val Asp Leu Glu Lys Asp Val His
945                 950                 955 tca ggc ttg atc ggc ccc ctt ctg atc tgc cgc gcc aac acc ctg aac      2927
Ser Gly Leu Ile Gly Pro Leu Leu Ile Cys Arg Ala Asn Thr Leu Asn
960                 965                 970                 975 gct gct cac ggt aga caa gtg acc gtg caa gaa ttt gct ctg ttt ttc      2975
Ala Ala His Gly Arg Gln Val Thr Val Gln Glu Phe Ala Leu Phe Phe
                980                 985                 990 act att ttt gat gag aca aag agc tgg tac ttc act gaa aat gtg gaa      3023
Thr Ile Phe Asp Glu Thr Lys Ser Trp Tyr Phe Thr Glu Asn Val Glu
            995                 1000                1005 agg aac tgc cgg gcc ccc tgc cac ctg cag atg gag gac ccc act ctg      3071
Arg Asn Cys Arg Ala Pro Cys His Leu Gln Met Glu Asp Pro Thr Leu
        1010                1015                1020 aaa gaa aac tat cgc ttc cat gca atc aat ggc tat gtg atg gat aca      3119
Lys Glu Asn Tyr Arg Phe His Ala Ile Asn Gly Tyr Val Met Asp Thr
    1025                1030                1035 ctc cct ggc tta gta atg gct cag aat caa agg atc cga tgg tat ctg      3167
Leu Pro Gly Leu Val Met Ala Gln Asn Gln Arg Ile Arg Trp Tyr Leu
1040                1045                1050                1055 ctc agc atg ggc agc aat gaa aat atc cat tcg att cat ttt agc gga      3215
Leu Ser Met Gly Ser Asn Glu Asn Ile His Ser Ile His Phe Ser Gly
                1060                1065                1070 cac gtg ttc agt gta cgg aaa aag gag gag tat aaa atg gcc gtg tac      3263
His Val Phe Ser Val Arg Lys Lys Glu Glu Tyr Lys Met Ala Val Tyr
            1075                1080                1085 aat ctc tat ccg ggt gtc ttt gag aca gtg gaa atg cta ccg tcc aaa      3311
Asn Leu Tyr Pro Gly Val Phe Glu Thr Val Glu Met Leu Pro Ser Lys
        1090                1095                1100 gtt gga att tgg cga ata gaa tgc ctg att ggc gag cac ctg caa gct      3359
Val Gly Ile Trp Arg Ile Glu Cys Leu Ile Gly Glu His Leu Gln Ala
```

-continued

```
                1105                1110                1115
ggg atg agc acg act ttc ctg gtg tac agc aag gag tgt cag gct cca         3407
Gly Met Ser Thr Thr Phe Leu Val Tyr Ser Lys Glu Cys Gln Ala Pro
1120                1125                1130                1135 ctg gga atg gct tct gga cgc att aga gat ttt cag atc aca gct tca         3455
Leu Gly Met Ala Ser Gly Arg Ile Arg Asp Phe Gln Ile Thr Ala Ser
                1140                1145                1150 gga cag tat gga cag tgg gcc cca aag ctg gcc aga ctt cat tat tcc         3503
Gly Gln Tyr Gly Gln Trp Ala Pro Lys Leu Ala Arg Leu His Tyr Ser
            1155                1160                1165 gga tca atc aat gcc tgg agc acc aag gat ccc cac tcc tgg atc aag         3551
Gly Ser Ile Asn Ala Trp Ser Thr Lys Asp Pro His Ser Trp Ile Lys
        1170                1175                1180 gtg gat ctg ttg gca cca atg atc att cac ggc atc atg acc cag ggt         3599
Val Asp Leu Leu Ala Pro Met Ile Ile His Gly Ile Met Thr Gln Gly
        1185                1190                1195 gcc cgt cag aag ttt tcc agc ctc tac atc tcc cag ttt atc atc atg         3647
Ala Arg Gln Lys Phe Ser Ser Leu Tyr Ile Ser Gln Phe Ile Ile Met
1200                1205                1210                1215 tac agt ctt gac ggg agg aac tgg cag agt tac cga ggg aat tcc acg         3695
Tyr Ser Leu Asp Gly Arg Asn Trp Gln Ser Tyr Arg Gly Asn Ser Thr
                1220                1225                1230 ggc acc tta atg gtc ttc ttt ggc aat gtg gac gca tct ggg att aaa         3743
Gly Thr Leu Met Val Phe Phe Gly Asn Val Asp Ala Ser Gly Ile Lys
            1235                1240                1245 cac aat att ttt aac cct ccg att gtg gct cgg tac atc cgt ttg cac         3791
His Asn Ile Phe Asn Pro Pro Ile Val Ala Arg Tyr Ile Arg Leu His
        1250                1255                1260 cca aca cat tac agc atc cgc agc act ctt cgc atg gag ttg atg ggc         3839
Pro Thr His Tyr Ser Ile Arg Ser Thr Leu Arg Met Glu Leu Met Gly
        1265                1270                1275 tgt gat tta aac agt tgc agc atg ccc ctg gga atg cag aat aaa gcg         3887
Cys Asp Leu Asn Ser Cys Ser Met Pro Leu Gly Met Gln Asn Lys Ala
1280                1285                1290                1295 ata tca gac tca cag atc acg gcc tcc tcc cac cta agc aat ata ttt         3935
Ile Ser Asp Ser Gln Ile Thr Ala Ser Ser His Leu Ser Asn Ile Phe
                1300                1305                1310 gcc acc tgg tct cct tca caa gcc cga ctt cac ctc cag ggg cgg acg         3983
Ala Thr Trp Ser Pro Ser Gln Ala Arg Leu His Leu Gln Gly Arg Thr
            1315                1320                1325 aat gcc tgg cga ccc cgg gtg agc agc gca gag gag tgg ctg cag gtg         4031
Asn Ala Trp Arg Pro Arg Val Ser Ser Ala Glu Glu Trp Leu Gln Val
        1330                1335                1340 gac ctg cag aag acg gtg aag gtc aca ggc atc acc acc cag ggc gtg         4079
Asp Leu Gln Lys Thr Val Lys Val Thr Gly Ile Thr Thr Gln Gly Val
        1345                1350                1355 aag tcc ctg ctc agc agc atg tat gtg aag gag ttc ctc gtg tcc agt         4127
Lys Ser Leu Leu Ser Ser Met Tyr Val Lys Glu Phe Leu Val Ser Ser
1360                1365                1370                1375 agt cag gac ggc cgc cgc tgg acc ctg ttt ctt cag gac ggc cac acg         4175
Ser Gln Asp Gly Arg Arg Trp Thr Leu Phe Leu Gln Asp Gly His Thr
                1380                1385                1390 aag gtt ttt cag ggc aat cag gac tcc tcc acc ccc gtg gtg aac gct         4223
Lys Val Phe Gln Gly Asn Gln Asp Ser Ser Thr Pro Val Val Asn Ala
            1395                1400                1405 ctg gac ccc ccg ctg ttc acg cgc tac ctg agg atc cac ccc acg agc         4271
Leu Asp Pro Pro Leu Phe Thr Arg Tyr Leu Arg Ile His Pro Thr Ser
        1410                1415                1420 tgg gcg cag cac atc gcc ctg agg ctc gag gtt cta gga tgt gag gca         4319
```

```
Trp Ala Gln His Ile Ala Leu Arg Leu Glu Val Leu Gly Cys Glu Ala
    1425                1430                1435 cag gat ctc tac tga                                              4334
Gln Asp Leu Tyr
1440

<210> SEQ ID NO 39
<211> LENGTH: 1443
<212> TYPE: PRT
<213> ORGANISM: Artificial Sequence
<220> FEATURE:
<223> OTHER INFORMATION: Description of Artificial Sequence: factor VIII
      lacking the B domain

<400> SEQUENCE: 39

Met Gln Leu Glu Leu Ser Thr Cys Val Phe Leu Cys Leu Leu Pro Leu
  1               5                  10                  15

Gly Phe Ser Ala Ile Arg Arg Tyr Tyr Leu Gly Ala Val Glu Leu Ser
             20                  25                  30

Trp Asp Tyr Arg Gln Ser Glu Leu Leu Arg Glu Leu His Val Asp Thr
         35                  40                  45

Arg Phe Pro Ala Thr Ala Pro Gly Ala Leu Pro Leu Gly Pro Ser Val
 50                  55                  60

Leu Tyr Lys Lys Thr Val Phe Val Glu Phe Thr Asp Gln Leu Phe Ser
 65                  70                  75                  80

Val Ala Arg Pro Arg Pro Pro Trp Met Gly Leu Leu Gly Pro Thr Ile
                 85                  90                  95

Gln Ala Glu Val Tyr Asp Thr Val Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
```

```
                    325                 330                 335
His Gly Gly Met Glu Ala His Val Arg Val Glu Ser Cys Ala Glu Glu
                340                 345                 350

Pro Gln Leu Arg Arg Lys Ala Asp Glu Glu Asp Tyr Asp Asp Asn
                355                 360                 365

Leu Tyr Asp Ser Asp Met Asp Val Val Arg Leu Asp Gly Asp Val
    370                 375                 380

Ser Pro Phe Ile Gln Ile Arg Ser Val Ala Lys Lys His Pro Lys Thr
385                 390                 395                 400

Trp Val His Tyr Ile Ser Ala Glu Glu Asp Trp Asp Tyr Ala Pro
                405                 410                 415

Ala Val Pro Ser Pro Ser Asp Arg Ser Tyr Lys Ser Leu Tyr Leu Asn
                420                 425                 430

Ser Gly Pro Gln Arg Ile Gly Arg Lys Tyr Lys Lys Ala Arg Phe Val
            435                 440                 445

Ala Tyr Thr Asp Val Thr Phe Lys Thr Arg Lys Ala Ile Pro Tyr Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Lys Ala Ser Arg Pro Tyr Asn Ile Tyr Pro
                485                 490                 495

His Gly Ile Thr Asp Val Ser Ala Leu His Pro Gly Arg Leu Leu Lys
            500                 505                 510

Gly Trp Lys His Leu Lys Asp Met Pro Ile Leu Pro Gly Glu Thr Phe
    515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Ile Asn Leu Glu Lys
545                 550                 555                 560

Asp Leu Ala Ser Gly Leu Ile Gly Pro Leu Ile Cys Tyr Lys Glu
                565                 570                 575

Ser Val Asp Gln Arg Gly Asn Gln Met Met Ser Asp Lys Arg Asn Val
                580                 585                 590

Ile Leu Phe Ser Val Phe Asp Glu Asn Gln Ser Trp Tyr Leu Ala Glu
                595                 600                 605

Asn Ile Gln Arg Phe Leu Pro Asn Pro Asp Gly Leu Gln Pro Gln Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Val Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
    690                 695                 700

Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
                725                 730                 735

Tyr Tyr Asp Asn Thr Tyr Glu Asp Ile Pro Gly Phe Leu Leu Ser Gly
                740                 745                 750
```

-continued

```
Lys Asn Val Ile Glu Pro Arg Asp Ile Ser Leu Pro Thr Phe Gln Pro
        755                 760                 765

Glu Glu Asp Lys Met Asp Tyr Asp Ile Phe Ser Thr Glu Thr Lys
        770                 775                 780

Gly Glu Asp Phe Asp Ile Tyr Gly Glu Asp Glu Asn Gln Asp Pro Arg
785                 790                 795                 800

Ser Phe Gln Lys Arg Thr Arg His Tyr Phe Ile Ala Ala Val Glu Gln
                805                 810                 815

Leu Trp Asp Tyr Gly Met Ser Glu Ser Pro Arg Ala Leu Arg Asn Arg
                820                 825                 830

Ala Gln Asn Gly Glu Val Pro Arg Phe Lys Lys Val Val Phe Arg Glu
                835                 840                 845

Phe Ala Asp Gly Ser Phe Thr Gln Pro Ser Tyr Arg Gly Glu Leu Asn
                850                 855                 860

Lys His Leu Gly Leu Leu Gly Pro Tyr Ile Arg Ala Glu Val Glu Asp
865                 870                 875                 880

Asn Ile Met Val Thr Phe Lys Asn Gln Ala Ser Arg Pro Tyr Ser Phe
                885                 890                 895

Tyr Ser Ser Leu Ile Ser Tyr Pro Asp Asp Gln Glu Gln Gly Ala Glu
                900                 905                 910

Pro Arg His Asn Phe Val Gln Pro Asn Glu Thr Arg Thr Tyr Phe Trp
                915                 920                 925

Lys Val Gln His His Met Ala Pro Thr Glu Asp Glu Phe Asp Cys Lys
                930                 935                 940

Ala Trp Ala Tyr Phe Ser Asp Val Asp Leu Glu Lys Asp Val His Ser
945                 950                 955                 960

Gly Leu Ile Gly Pro Leu Leu Ile Cys Arg Ala Asn Thr Leu Asn Ala
                965                 970                 975

Ala His Gly Arg Gln Val Thr Val Gln Glu Phe Ala Leu Phe Phe Thr
                980                 985                 990

Ile Phe Asp Glu Thr Lys Ser Trp Tyr Phe Thr Glu Asn Val Glu Arg
                995                 1000                1005

Asn Cys Arg Ala Pro Cys His Leu Gln Met Glu Asp Pro Thr Leu Lys
        1010                1015                1020

Glu Asn Tyr Arg Phe His Ala Ile Asn Gly Tyr Val Met Asp Thr Leu
1025                1030                1035                1040

Pro Gly Leu Val Met Ala Gln Asn Gln Arg Ile Arg Trp Tyr Leu Leu
                1045                1050                1055

Ser Met Gly Ser Asn Glu Asn Ile His Ser Ile His Phe Ser Gly His
                1060                1065                1070

Val Phe Ser Val Arg Lys Lys Glu Glu Tyr Lys Met Ala Val Tyr Asn
        1075                1080                1085

Leu Tyr Pro Gly Val Phe Glu Thr Val Glu Met Leu Pro Ser Lys Val
        1090                1095                1100

Gly Ile Trp Arg Ile Glu Cys Leu Ile Gly Glu His Leu Gln Ala Gly
1105                1110                1115                1120

Met Ser Thr Thr Phe Leu Val Tyr Ser Lys Glu Cys Gln Ala Pro Leu
                1125                1130                1135

Gly Met Ala Ser Gly Arg Ile Arg Asp Phe Gln Ile Thr Ala Ser Gly
                1140                1145                1150

Gln Tyr Gly Gln Trp Ala Pro Lys Leu Ala Arg Leu His Tyr Ser Gly
                1155                1160                1165
```

```
Ser Ile Asn Ala Trp Ser Thr Lys Asp Pro His Ser Trp Ile Lys Val
    1170            1175            1180

Asp Leu Leu Ala Pro Met Ile Ile His Gly Ile Met Thr Gln Gly Ala
1185            1190            1195            1200

Arg Gln Lys Phe Ser Ser Leu Tyr Ile Ser Gln Phe Ile Ile Met Tyr
                1205            1210            1215

Ser Leu Asp Gly Arg Asn Trp Gln Ser Tyr Arg Gly Asn Ser Thr Gly
            1220            1225            1230

Thr Leu Met Val Phe Phe Gly Asn Val Asp Ala Ser Gly Ile Lys His
        1235            1240            1245

Asn Ile Phe Asn Pro Pro Ile Val Ala Arg Tyr Ile Arg Leu His Pro
    1250            1255            1260

Thr His Tyr Ser Ile Arg Ser Thr Leu Arg Met Glu Leu Met Gly Cys
1265            1270            1275            1280

Asp Leu Asn Ser Cys Ser Met Pro Leu Gly Met Gln Asn Lys Ala Ile
                1285            1290            1295

Ser Asp Ser Gln Ile Thr Ala Ser Ser His Leu Ser Asn Ile Phe Ala
            1300            1305            1310

Thr Trp Ser Pro Ser Gln Ala Arg Leu His Leu Gln Gly Arg Thr Asn
        1315            1320            1325

Ala Trp Arg Pro Arg Val Ser Ser Ala Glu Glu Trp Leu Gln Val Asp
    1330            1335            1340

Leu Gln Lys Thr Val Lys Val Thr Gly Ile Thr Thr Gln Gly Val Lys
1345            1350            1355            1360

Ser Leu Leu Ser Ser Met Tyr Val Lys Glu Phe Leu Val Ser Ser Ser
                1365            1370            1375

Gln Asp Gly Arg Arg Trp Thr Leu Phe Leu Gln Asp Gly His Thr Lys
            1380            1385            1390

Val Phe Gln Gly Asn Gln Asp Ser Ser Thr Pro Val Val Asn Ala Leu
        1395            1400            1405

Asp Pro Pro Leu Phe Thr Arg Tyr Leu Arg Ile His Pro Thr Ser Trp
    1410            1415            1420

Ala Gln His Ile Ala Leu Arg Leu Glu Val Leu Gly Cys Glu Ala Gln
1425            1430            1435            1440

Asp Leu Tyr

<210> SEQ ID NO 40
<211> LENGTH: 19
<212> TYPE: PRT
<213> ORGANISM: Homo sapiens

<400> SEQUENCE: 40

Met Gln Ile Glu Leu Ser Thr Cys Phe Phe Leu Cys Leu Leu Arg Phe
 1               5                  10                 15

Cys Phe Ser
```

NUCLEIC ACID MOLECULES ENCODING MODIFIED FACTOR VIII PROTEINS, EXPRESSION PRODUCTS, AND METHODS OF MAKING THE SAME

CROSS REFERENCE TO RELATED APPLICATIONS

This application is a divisional application of U.S. patent application Ser. No. 09/315,179 filed May 20, 1999, now U.S. Patent No. 6,376,463, which is a continuation-in-part of U.S. patent application Ser. No. 09/037,601 filed Mar. 10,1998; now U.S. Pat. No. 6,180,371, which is a continuation-in-part of U.S. Pat. Ser. No. 08/670,707 filed Jun. 26, 1996, which issued as U.S. Pat. No. 5,859,204, and of International Patent Application No. PCT/US97/11155 filed Jun. 26, 1997. Application Ser. No. 08/670,707 is a continuation-in-part of PCT/US94/13200 entitled "Hybrid Human/Animal Factor VIII" filed Nov. 15, 1994, and of U.S. Ser. No. 08/212,133 entitled "Hybrid Human/Animal Factor VIII" filed Mar. 11, 1994, now U.S. Pat. No. 5,663,060, which is a continuation-in-part of U.S. Ser. No. 07/864,004 entitled "Hybrid Human/Porcine Factor VIII" filed Apr. 7, 1992, and which issued as U.S. Pat. No. 5,364,771 on Nov. 15, 1994. Application No. PCT/US97/11155 is a continuation-in-part of application Ser. No. 08/670,707.

ACKNOWLEDGEMENT OF FEDERAL RESEARCH SUPPORT

The government has rights in this invention arising from National Institutes of Health Grant No. HL46215 that partially funded the research leading to this invention.

BACKGROUND OF THE INVENTION

This invention relates generally to a hybrid factor VIII having human and animal factor VIII amino acid sequence or having human factor VIII and non-factor VIII amino acid sequence and methods of preparation and use thereof.

Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a protein precursor is converted to a protease that cleaves the next protein precursor in the series. Cofactors are required at most of the steps.

Factor VIII circulates as an inactive precursor in blood, bound tightly and non-covalently to von Willebrand factor. Factor VIII is proteolytically activated by thrombin or factor Xa, which dissociates it from von Willebrand factor and activates its procoagulant function in the cascade. In its active form, the protein factor VIIIa is a cofactor that increases the catalytic efficiency of factor IXa toward factor X activation by several orders of magnitude.

People with deficiencies in factor VIII or antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of human factor VIII, which will restore the blood's normal clotting ability if administered with sufficient frequency and concentration. The classic definition of factor VIII, in fact, is that substance present in normal blood plasma that corrects the clotting defect in plasma derived from individuals with hemophilia A.

The development of antibodies ("inhibitors" or "inhibitory antibodies") that inhibit the activity of factor VIII is a serious complication in the management of patients with hemophilia. Autoantibodies develop in approximately 20% of patients with hemophilia A in response to therapeutic infusions of factor VIII. In previously untreated patients with hemophilia A who develop inhibitors, the inhibitor usually develops within one year of treatment. Additionally, autoantibodies that inactivate factor VIII occasionally develop in individuals with previously normal factor VIII levels. If the inhibitor titer is low enough, patients can be managed by increasing the dose of factor VIII. However, often the inhibitor titer is so high that it cannot be overwhelmed by factor VIII. An alternative strategy is to bypass the need for factor VIII during normal hemostasis using factor IX complex preparations (for example, KONYNE®, PROPLEX®) or recombinant human factor VIIa. Additionally, since porcine factor VIII usually has substantially less reactivity with inhibitors than human factor VIII, a partially purified porcine factor VIII preparation (HYATE:C®) is used. Many patients who have developed inhibitory antibodies to human factor VIII have been successfully treated with porcine factor VIII and have tolerated such treatment for long periods of time. However, administration of porcine factor VIII is not a complete solution because inhibitors may develop to porcine factor VIII after one or more infusions.

Several preparations of human plasma-derived factor VIII of varying degrees of purity are available commercially for the treatment of hemophilia A. These include a partially-purified factor VIII derived from the pooled blood of many donors that is heat- and detergent-treated for viruses but contain a significant level of antigenic proteins; a monoclonal antibody-purified factor VIII that has lower levels of antigenic impurities and viral contamination; and recombinant human factor VIII, clinical trials for which are underway. Unfortunately, human factor VIII is unstable at physiologic concentrations and pH, is present in blood at an extremely low concentration (0.2 μg/ml plasma), and has low specific clotting activity.

Hemophiliacs require daily replacement of factor VIII to prevent bleeding and the resulting deforming hemophilic arthropathy. However, supplies have been inadequate and problems in therapeutic use occur due to difficulty in isolation and purification, immunogenicity, and the necessity of removing the AIDS and hepatitis infectivity risk. The use of recombinant human factor VIII or partially-purified porcine factor VIII will not resolve all the problems.

The problems associated with the commonly used, commercially available, plasma-derived factor VIII have stimulated significant interest in the development of a better factor VIII product. There is a need for a more potent factor VIII molecule so that more units of clotting activity can be delivered per molecule; a factor VIII molecule that is stable at a selected pH and physiologic concentration; a factor VIII molecule that is less apt to cause production of inhibitory antibodies; and a factor VIII molecule that evades immune detection in patients who have already acquired antibodies to human factor VIII.

It is therefore an object of the present invention to provide a factor VIII that corrects hemophilia in a patient deficient in factor VIII or having inhibitors to factor VIII.

It is a further object of the present invention to provide methods for treatment of hemophiliacs.

It is still another object of the present invention to provide a factor VIII that is stable at a selected pH and physiologic concentration.

It is yet another object of the present invention to provide a factor VIII that has greater coagulant activity than human factor VIII.

It is an additional object of the present invention to provide a factor VIII against which less antibody is produced.

SUMMARY OF THE INVENTION

The present invention provides isolated, purified, hybrid factor VIII molecules and fragments thereof with coagulant activity including hybrid factor VIII having factor VIII amino acid sequence derived from human and pig or other non-human mammal (together referred to herein as "animal"); or in a second embodiment including a hybrid equivalent factor VIII having factor VIII amino acid sequence derived from human or animal or both and amino acid sequence having no known sequence identity to factor VIII ("non-factor VIII amino acid sequence"), preferably substituted in an antigenic and/or immunogenic region of the factor VIII, is described. One skilled in the art will realize that numerous hybrid factor VIII constructs can be prepared including, but not limited to, human/animal factor VIII having greater coagulant activity than human factor VIII ("superior coagulant activity"); non-immunogenic human/equivalent factor VIII; non-antigenic human/equivalent or human/animal factor VIII; non-immunogenic human/animal or human/equivalent factor VIII having superior coagulant activity; non-antigenic human/animal or human/animal/equivalent factor VIII having superior coagulant activity; non-immunogenic, non-antigenic human/equivalent or human/equivalent/animal factor VIII; and non-immunogenic, non-antigenic human/animal/equivalent factor VIII having superior coagulant activity.

The hybrid factor VIII molecule is produced by isolation and recombination of human and animal factor VIII subunits or domains; or by genetic engineering of the human and animal factor VIII genes.

In a preferred embodiment, recombinant DNA methods are used to substitute elements of animal factor VIII for the corresponding elements of human factor VIII, resulting in hybrid human/animal factor VIII molecules. In a second preferred embodiment, recombinant DNA methods are used to replace one or more amino acids in the human or animal factor VIII or in a hybrid human/animal factor VIII with amino acids that have no known sequence identity to factor VIII, preferably a sequence of amino acids that has less immunoreactivity with naturally occurring inhibitory antibodies to factor VIII ("nonantigenic amino acid sequence") and/or is less apt to elicit the production of antibodies to factor VIII ("non-immunogenic amino acid sequence") than human factor VIII. An example of an amino acid sequence that can be used to replace immunogenic or antigenic sequence is a sequence of alanine residues.

In another embodiment, subunits of factor VIII are isolated and purified from human or animal plasma, and hybrid human/animal factor VIII is produced either by mixture of animal heavy chain subunits with human light chain subunits or by mixture of human heavy chain subunits with animal light chain subunits, thereby producing human light chain/animal heavy chain and human heavy chain/animal light chain hybrid molecules. These hybrid molecules are isolated by ion exchange chromatography.

Alternatively, one or more domains or partial domains of factor VIII are isolated and purified from human or animal plasma, and hybrid human/animal factor VIII is produced by mixture of domains or partial domains from one species with domains or partial domains of the second species. Hybrid molecules can be isolated by ion exchange chromatography.

Methods for preparing highly purified hybrid factor VIII are described having the steps of: (a) isolation of subunits of plasma-derived human factor VIII and subunits of plasma-derived animal factor VIII, followed by reconstitution of coagulant activity by mixture of human and animal subunits, followed by isolation of hybrid human/animal factor VIII by ion exchange chromatography; (b) isolation of domains or partial domains of plasma-derived human factor VIII and domains or partial domains of plasma-derived animal factor VIII, followed by reconstitution of coagulant activity by mixture of human and animal domains, followed by isolation of hybrid human/animal factor VIII by ion exchange chromatography; (c) construction of domains or partial domains of animal factor VIII by recombinant DNA technology, and recombinant exchange of domains of animal and human factor VIII to produce hybrid human/animal factor VIII with coagulant activity; (d) creation of hybrid human/animal factor VIII by replacement of specific amino acid residues of the factor VIII of one species with the corresponding unique amino acid residues of the factor VIII of the other species; or (e) creation of a hybrid equivalent factor VIII molecule having human or animal amino acid sequence or both, in which specific amino acid residues of the factor VIII are replaced with amino acid residues having no known sequence identity to factor VIII by site-directed mutagenesis.

The determination of the entire DNA sequence encoding porcine factor VIII set forth herein has enabled, for the first time, the synthesis of full-length porcine factor VIII by expressing the DNA encoding porcine factor VIII in a suitable host cell. Purified recombinant porcine factor VIII is therefore an aspect of the present invention. The DNA encoding each domain of porcine factor VIII as well as any specified fragment thereof, can be similarly expressed, either by itself or in combination with DNA encoding human factor VIII to make the hybrid human/porcine factor VIII described herein. Furthermore, porcine fVIII having all or part of the B domain deleted (B-domainless porcine fVIII) is made available as part of the present invention, by expression DNA encoding porcine fVIII having a deletion of one or more codons of the B-domain.

Some embodiments of hybrid or hybrid equivalent factor VIII have specific activity greater than that of human factor VIII and equal to or greater than that of porcine factor VIII. Some embodiments of hybrid or hybrid equivalent factor VIII have equal or less immunoreactivity with inhibitory antibodies to factor VIII and/or less immunogenicity in humans or animals, compared to human or porcine factor VIII.

Also provided are pharmaceutical compositions and methods for treating patients having factor VIII deficiency comprising administering the hybrid or hybrid equivalent factor VIII.

BRIEF DESCRIPTION OF THE DRAWINGS

FIGS. 1A–1H taken together provide an aligned sequence comparison of the human, pig and mouse factor VIII acid sequences. For human sequence, see SEQ ID NO:2; pig sequence, see SEQ ID NO:37; for mouse sequence, see SEQ ID NO:6.

DETAILED DESCRIPTION OF THE INVENTION

Unless otherwise specified or indicated, as used herein, "factor VIII" denotes any functional factor VIII protein molecule from any animal, any hybrid factor VIII or modified factor VIII, "hybrid factor VIII" or "hybrid protein" denotes any functional factor VIII protein molecule or fragment thereof comprising factor VIII amino acid sequence from human, porcine, and/or non-human, non-porcine mammalian species. Such combinations include, but are not limited to, any or all of the following hybrid factor VIII molecules or fragments thereof: (1) human/porcine; (2) human/non-human, non-porcine mammalian, such as human/mouse; (3) porcine/non-human, non-porcine mammalian, such as mouse/dog. Such combinations also include hybrid factor VIII equivalent molecules or fragments thereof, as further defined below, comprising factor VIII amino acid sequence of hybrid, human, porcine, or non-human, non-porcine mammalian origin in which amino acid sequence having no known sequence identity to factor VIII is substituted. Such hybrid combinations also include hybrid factor VIII amino sequence derived from more than two species, such as human/pig/mouse, or from two or more species in which amino acid sequence having no known sequence identity to factor VIII is substituted. Unless otherwise indicated, "hybrid factor VIII" includes fragments of the hybrid factor VIII, which can be used, as described below in one exemplary embodiment, as probes for research purposes or as diagnostic reagents.

As used herein, "mammalian factor VIII" includes factor VIII with amino acid sequence derived from any non-human mammal, unless otherwise specified. "Animal", as used herein, refers to pig and other non-human mammals.

A "fusion protein" or "fusion factor VIII or fragment thereof", as used herein, is the product of a hybrid gene in which the coding sequence for one protein is extensively altered, for example, by fusing part of it to the coding sequence for a second protein from a different gene to produce a hybrid gene that encodes the fusion protein. As used herein, a fusion protein is a subset of the hybrid factor VIII protein described in this application.

A "corresponding" nucleic acid or amino acid or sequence of either, as used herein, is one present at a site in a factor VIII or hybrid factor VIII molecule or fragment thereof that has the same structure and/or function as a site in the factor VIII molecule of another species, although the nucleic acid or amino acid number may not be identical. A sequence "corresponding to" another factor VIII sequence substantially corresponds to such sequence, and hybridizes to the sequence of the designated SEQ ID NO. under stringent conditions. A sequence "corresponding to" another factor VIII sequence also includes a sequence that results in the expression of a factor VIII or claimed procoagulant hybrid factor VIII or fragment thereof and would hybridize to the designated SEQ ID NO but for the redundancy of the genetic code.

A "unique" amino acid residue or sequence, as used herein, refers to an amino acid sequence or residue in the factor VIII molecule of one species that is different from the homologous residue or sequence in the factor VIII molecule of another species.

"Specific activity," as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed. Hybrid human/porcine factor VIII has coagulation activity in a human factor VIII assay. This activity, as well as that of other hybrid or hybrid equivalent factor VIII molecules or fragments thereof, may be less than, equal to, or greater than that of either plasma-derived or recombinant human factor VIII.

The human factor VIII cDNA nucleotide and predicted amino acid sequences are shown in SEQ ID NOs:1 and 2, respectively. Factor VIII is synthesized as an approximately 300 kDa single chain protein with internal sequence homology that defines the "domain" sequence $NH_2$-A1-A2-B-A3-C1-C2-COOH. In a factor VIII molecule, a "domain", as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO:2): A1, residues Ala1-Arg372; A2, residues Ser373-Arg740; B, residues Ser741-Arg1648; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain.

"Subunits" of human or animal factor VIII, as used herein, are the heavy and light chains of the protein. The heavy chain of factor VIII contains three domains, A1, A2, and B. The light chain of factor VIII also contains three domains, A3, C1, and C2.

The hybrid factor VIII or fragment thereof can be made (1) by substitution of isolated, plasma-derived animal subunits or human subunits (heavy or light chains) for corresponding human subunits or animal subunits; (2) by substitution of human domains or animal domains (A1, A2, A3, B, C1, and C2) for corresponding animal domains or human domains; (3) by substitution of parts of human domains or animal domains for parts of animal domains or human domains; (4) by substitution of at least one specific sequence including one or more unique human or animal amino acid(s) for the corresponding animal or human amino acid(s); or (5) by substitution of amino acid sequence that has no known sequence identity to factor VIII for at least one sequence including one or more specific amino acid residue(s) in human, animal, or hybrid factor VIII or fragments thereof. A "B-domainless" hybrid factor VIII, hybrid equivalent factor VIII, or fragment of either, as used herein, refers to any one of the hybrid factor VIII constructs described herein that lacks the B domain, or a portion thereof.

The terms "epitope", "antigenic site", and "antigenic determinant", as used herein, are used synonymously and are defined as a portion of the human, animal, hybrid, or hybrid equivalent factor VIII or fragment thereof that is specifically recognized by an antibody. It can consist of any number of amino acid residues, and it can be dependent upon the primary, secondary, or tertiary structure of the protein. In accordance with this disclosure, a hybrid factor VIII, hybrid factor VIII equivalent, or fragment of either that includes at least one epitope may be used as a reagent in the diagnostic assays described below. In some embodiments, the hybrid or hybrid equivalent factor VIII or fragment thereof is not cross-reactive or is less cross-reactive with all naturally occurring inhibitory factor VIII antibodies than human or porcine factor VIII.

The term "immunogenic site", as used herein, is defined as a region of the human or animal factor VIII, hybrid or hybrid equivalent factor VIII, or fragment thereof that specifically elicits the production of antibody to the factor VIII, hybrid, hybrid equivalent, or fragment in a human or animal, as measured by routine protocols, such as immunoassay, e.g. ELISA, or the Bethesda assay, described herein. It can consist of any number of amino acid residues, and it can be dependent upon the primary, secondary, or tertiary structure of the protein. In some embodiments, the hybrid or hybrid equivalent factor VIII or fragment thereof is nonimmunogenic or less immunogenic in an animal or human than human or porcine factor VIII.

As used herein, a "hybrid factor VIII equivalent molecule or fragment thereof" or "hybrid equivalent factor VIII or fragment thereof" is an active factor VIII or hybrid factor VIII molecule or fragment thereof comprising at least one sequence including one or more amino acid residues that have no known identity to human or animal factor VIII sequence substituted for at least one sequence including one or more specific amino acid residues in the human, animal, or hybrid factor VIII or fragment thereof. The sequence of one or more amino acid residues that have no known identity to human or animal factor VIII sequence is also referred to herein as "non-factor VIII amino acid sequence". In a preferred embodiment, the amino acid(s) having no known sequence identity to factor VIII sequence are alanine residues. In another preferred embodiment, the specific factor VIII sequence for which the amino acid(s) having no known sequence identity to factor VIII sequence are substituted includes an antigenic site that is immunoreactive with naturally occurring factor VIII inhibitory antibodies, such that the resulting hybrid factor VIII equivalent molecule or fragment thereof is less immunoreactive or not immunoreactive with factor VIII inhibitory antibodies. In yet another preferred embodiment, the specific hybrid factor VIII sequence for which the amino acid(s) having no known sequence identity to factor VIII sequence are substituted includes an immunogenic site that elicits the formation of factor VIII inhibitory antibodies in an animal or human, such that the resulting hybrid factor VIII equivalent molecule or fragment thereof is less immunogenic.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

As used herein, "diagnostic assays" include assays that in some manner utilize the antigen-antibody interaction to detect and/or quantify the amount of a particular antibody that is present in a test sample to assist in the selection of medical therapies. There are many such assays known to those of skill in the art. As used herein, however, the hybrid or hybrid equivalent factor VIII DNA or fragment thereof and protein expressed therefrom, in whole or in part, can be substituted for the corresponding reagents in the otherwise known assays, whereby the modified assays may be used to detect and/or quantify antibodies to factor VIII. It is the use of these reagents, the hybrid or hybrid equivalent factor VIII DNA or fragment thereof or protein expressed therefrom, that permits modification of known assays for detection of antibodies to human or animal factor VIII or to hybrid human/animal factor VIII. Such assays include, but are not limited to ELISAs, immunodiffusion assays, and immunoblots. Suitable methods for practicing any of these assays are known to those of skill in the art. As used herein, the hybrid or hybrid equivalent factor VIII or fragment thereof that includes at least one epitope of the protein can be used as the diagnostic reagent. Examples of other assays in which the hybrid or hybrid equivalent factor VIII or fragment thereof can be used include the Bethesda assay and anticoagulation assays.

The "expression product" of a DNA encoding a human or animal factor VIII or a human/animal hybrid factor VIII or a modified factor VIII is the product obtained from expression of the referenced DNA in a suitable host cell, including such features of pre- or post-translational modification of protein encoded by the referenced DNA, including but not limited to glycosylation, proteolytic cleavage and the like. It is known in the art that such modifications can occur and can differ somewhat depending upon host cell type and other factors, and can result in molecular isoforms of the product, with retention of procoagulant activity. See, e.g. Lind, P. et al., *Eur. J. Biochem*. 232:1927 (1995) incorporated herein by reference.

"Immunoreactivity reducing" amino acids are defined herein as those amino acids that are minor contributors, if at all, to the binding energy of an antibody-antigen pair. Non-limiting examples of some amino acids known to be immunoreactivity-reducing include alanine, methionine, leucine, serine and glycine. It will be understood that the reduction of immunoreactivity achievable by a given amino acid substitution in a given antigen-antibody pair will also depend on any effects the substitution may have on protein conformation, epitope accessibility and the like.

General Description of Methods

U.S. Ser. No. 07/864,004 described the discovery of hybrid human/porcine factor VIII molecules having coagulant activity, in which elements of the factor VIII molecule of human or pig are substituted for corresponding elements of the factor VIII molecule of the other species. U.S. Ser. No. 08/212,133 and PCT/US94/13200 describe procoagulant hybrid human/animal and hybrid equivalent factor VIII molecules, in which elements of the factor VIII molecule of one species are substituted for corresponding elements of the factor VIII molecule of the other species.

The present invention provides hybrid human/animal, animal/animal, and equivalent factor VIII molecules, modified factor VIII molecules and fragments thereof, and the nucleic acid sequences encoding such hybrids and modified factor VIII molecules, some of which have greater coagulant activity in a standard clotting assay when compared to highly-purified human factor VIII; and/or are less immunoreactive to inhibitory antibodies to human or porcine factor VIII than human or porcine factor VIII; and/or are less immunogenic in a human or animal than human or porcine factor VIII; and/or have other thereapeutically useful properties. These hybrid and/or modified factor VIII molecules can be constructed as follows.

At least five types of active hybrid human/porcine or hybrid equivalent factor VIII molecules or fragments thereof, the nucleic acid sequences encoding these hybrid factor VIII molecules, and the methods for preparing them are disclosed herein: those obtained (1) by substituting a human or porcine subunit (i.e., heavy chain or light chain) for the corresponding porcine or human subunit; (2) by substituting one or more human or porcine domain(s) (i.e., A1, A2, A3, B, C1, and C2) for the corresponding porcine or human domain(s); (3) by substituting a continuous part of one or more human or porcine domain(s) for the corresponding part of one or more porcine or human domain(s); (4) by substituting at least one specific sequence including one or more unique amino acid residue(s) in human or porcine factor VIII for the corresponding porcine or human sequence; and (5) by substituting at least one sequence including one or more amino acid residue(s) having no known sequence identity to factor VIII ("non-factor VIII amino acid sequence") for at least one specific sequence of one or more amino acids in human, porcine, or hybrid human/porcine factor VIII. Modified factor VIII molecules have one or more amino acid replacements at specified positions.

At least five types of active hybrid human/non-human, non-porcine mammalian or hybrid equivalent factor VIII molecules or fragments thereof, and the nucleic acid sequences encoding them, can also be prepared by the same methods: those obtained (1) by substituting a human or non-human, non-porcine mammalian subunit (i.e., heavy chain or light chain) for the corresponding non-human, non-porcine mammalian or human subunit; (2) by substituting one or more human or non-human, non-porcine mammalian domain(s) (i.e., A1, A2, A3, B, C1 and C2) for the corresponding non-human, non-porcine mammalian or human domain(s); (3) by substituting a continuous part of one or more human or non-human, non-porcine mammalian domain(s) for the corresponding part of one or more non-human, non-porcine mammalian or human domain(s); (4) by substituting at least one specific sequence including one or more unique amino acid residue(s) in human or non-human, non-porcine mammalian factor VIII for the corresponding non-human, non-porcine mammalian or human sequence; and (5) by substituting at least one sequence including one or more amino acid residue(s) having no known sequence identity to factor VIII ("non-factor VIII amino acid sequence") for at least one specific sequence of one or more amino acids in human, non-human, non-porcine mammalian, or hybrid human/non-human, non-porcine mammalian factor VIII. Individual amino acid replacements can be obtained by site-directed mutagenesis of the corresponding segment of coding DNA.

Further, one skilled in the art will readily recognize that the same methods can be used to prepare at least five types of active hybrid factor VIII molecules or fragments thereof, corresponding to types (1)–(5) in the previous two paragraphs, comprising factor VIII amino acid sequence from two or more non-human mammals, such as porcine/mouse, and further comprising non-factor VIII amino acid sequence.

Hybrid human/animal, animal/animal, and equivalent factor VIII proteins or fragments thereof listed above under groups (1)–(3) are made by isolation of subunits, domains, or continuous parts of domains of plasma-derived factor VIII, followed by reconstitution and purification. Hybrid human/animal, animal/animal, and equivalent factor VIII proteins or fragments thereof described under groups (3)–(5) above are made by recombinant DNA methods. The hybrid molecule may contain a greater or lesser percentage of human than animal sequence, depending on the origin of the various regions, as described in more detail below.

Since current information indicates that the B domain has no inhibitory epitope and has no known effect on factor VIII function, in some embodiments the B domain is deleted in the active hybrid or hybrid equivalent factor VIII molecules or fragments thereof ("B(–) factor VIII") prepared by any of the methods described herein.

It is shown in Example 4 that hybrid human/porcine factor VIII comprising porcine heavy chain and human light chain and corresponding to the first type of hybrid listed above has greater specific coagulant activity in a standard clotting assay compared to human factor VIII. The hybrid human/animal or equivalent factor VIII with coagulant activity, whether the activity is higher, equal to, or lower than that of human factor VIII, can be useful in treating patients with inhibitors, since these inhibitors can react less with hybrid human/animal or equivalent factor VIII than with either human or porcine factor VIII.

Preparation of Hybrid Factor VIII Molecules from Isolated Human and Animal Factor VIII Subunits by Reconstitution:

The present invention provides hybrid human/animal factor VIII molecules or fragments thereof, with subunit substitutions, the nucleic acid sequences encoding these hybrids, methods for preparing and isolating them, and methods for characterizing their procoagulant activity. One method, modified from procedures reported by Fay, P. J. et al. (1990) *J. Biol. Chem.* 265:6197; and Lollar, J. S. et al. (1988) *J. Biol. Chem.* 263:10451, involves the isolation of subunits (heavy and light chains) of human and animal factor VIII, followed by recombination of human heavy chain and animal light chain or by recombination of human light chain and animal heavy chain.

Isolation of both human and animal individual subunits involves dissociation of the light chain/heavy chain dimer. This is accomplished, for example, by chelation of calcium with ethylenediaminetetraacetic acid (EDTA), followed by MONO S™ HPLC (Pharmacia-LKB, Piscataway, N.J.). Hybrid human/animal factor VIII molecules are reconstituted from isolated subunits in the presence of calcium. Hybrid human light chain/animal heavy chain or animal light chain/human heavy chain factor VIII is isolated from unreacted heavy chains by MONO S™ HPLC by procedures for the isolation of porcine factor VIII, such as described by Lollar, J. S. et al. (1988) *Blood* 71:137–143.

These methods, used in one embodiment to prepare active hybrid human/porcine factor VIII, described in detail in the examples below, result in hybrid human light chain/porcine heavy chain molecules with greater than six times the procoagulant activity of human factor VIII.

Other hybrid human/non-human, non-porcine mammalian factor VIII molecules can be prepared, isolated, and characterized for activity by the same methods. One skilled in the art will readily recognize that these methods can also be used to prepare, isolate, and characterize for activity hybrid animal/animal factor VIII, such as porcine/mouse, comprising the light or heavy chain or one species is combined with the heavy or light chain of the other species.

Preparation of Hybrid Factor VIII Molecules from Isolated Human and Animal Factor VIII Domains by Reconstitution:

The present invention provides hybrid human/animal factor VIII molecules or fragments thereof with domain substitutions, the nucleic acid sequences encoding them, methods for preparing and isolating them, and methods for characterizing their procoagulant activity. One method involves the isolation of one or more domains of human and one or more domains of animal factor VIII, followed by recombination of human and animal domains to form hybrid human/animal factor VIII with coagulant activity, as described by Lollar, P. et al. (Nov. 25, 1992) *J. Biol. Chem.* 267(33):23652–23657, for hybrid human/porcine factor VIII.

Specifically provided is a hybrid human/porcine factor VIII with substitution of the porcine A2 domain for the human A2 domain, which embodiment illustrates a method by which domain-substituted hybrid human/non-human, non-porcine mammalian factor VIII can be constructed. Plasma-derived non-human, non-porcine mammalian and human A1/A3-C1-C2 dimers are isolated by dissociation of the A2 domain from factor VIIIa. This is accomplished, for example, in the presence of NaOH, after which the mixture is diluted and the dimer is eluted using MONO S™ HPLC (Pharmacia-LKB, Piscataway, N.J.). The A2 domain is isolated from factor VIIIa as a minor component in the MONO S™ HPLC. Hybrid human/animal factor VIII molecules are reconstituted by mixing equal volumes of the A2 domain of one species and the A1/A3-C1-C2 dimer of the other species.

Hybrid human/animal factor VIII or fragments thereof with one or more domain substitutions is isolated from the mixture of unreacted dimers and A2 by MONO S™ HPLC by procedures for the isolation of porcine factor VIII, as described by Lollar, J. S. et al. (1988) *Blood* 71:137–143. Routine methods can also be used to prepare and isolate the A1, A3, C1, C2, and B domains of the factor VIII of one species, any one or more of which can be substituted for the corresponding domain in the factor VIII of the other species. One skilled in the art will readily recognize that these methods can also be used to prepare, isolate, and characterize for activity domain-substituted hybrid animal/animal factor VIII, such as porcine/mouse.

These methods, described in detail in the examples below, result in hybrid factor VIII molecules with procoagulant activity.

Preparation of Hybrid Factor VIII Molecules by Recombinant Engineering of the Sequences Encoding Human, Animal and Hybrid Factor VIII Subunits, Domains, or Parts of Domains:

Substitution of Subunits, Domains, Continuous Parts of Domains:

The present invention provides active, recombinant hybrid human/animal and hybrid equivalent factor VIII molecules and fragments thereof with subunit, domain, and amino acid sequence substitutions, the nucleic acid sequences encoding these hybrids, methods for preparing and isolating them, and methods for characterizing their coagulant, immunoreactive, and immunogenic properties.

The human factor VIII gene was isolated and expressed in mammalian cells, as reported by Toole, J. J. et al. (1984) *Nature* 312:342–347 (Genetics Institute); Gitschier, J. et al.(1984) *Nature* 312:326–330 (Genentech); Wood, W. I. et al. (1984) *Nature* 312:330–337 (Genentech); Vehar, G. A. et al. (1984) *Nature* 312:337–342 (Genentech); WO 87/04187; WO 88/08035; WO 88/03558; U.S. Pat. No. 4,757,006, and the amino acid sequence was deduced from cDNA. U.S. Pat. No. 4,965,199 to Capon et al. discloses a recombinant DNA method for producing factor VIII in mammalian host cells and purification of human factor VIII. Human factor VIII expression on CHO (Chinese hamster ovary) cells and BHKC (baby hamster kidney cells) has been reported. Human factor VIII has been modified to delete part or all of the B domain (U.S. Pat. No. 4,868,112), and replacement of the human factor VIII B domain with the human factor V B domain has been attempted (U.S. Pat. No. 5,004,803). The cDNA sequence encoding human factor VIII and predicted amino acid sequence are shown in SEQ ID NOs:1 and 2, respectively. In SEQ ID NO:1, the coding region begins at nucleotide position 208, the triplet GCC being the codon for amino acid number 1 (Ala) as given in SEQ ID NO:2.

Porcine factor VIII has been isolated and purified from plasma [Fass, D. N. et al. (1982) *Blood* 59:594]. Partial amino acid sequence of porcine factor VIII corresponding to portions of the N-terminal light chain sequence having homology to ceruloplasmin and coagulation factor V and largely incorrectly located were described by Church et al. (1984) *Proc. Natl. Acad. Sci. USA* 81:6934. Toole, J. J. et al. (1984) *Nature* 312:342–347 described the partial sequencing of the N-terminal end of four amino acid fragments of porcine factor VIII but did not characterize the fragments as to their positions in the factor VIII molecule. The amino acid sequence of the B and part of the A2 domains of porcine factor VIII were reported by Toole, J. J. et al. (1986) *Proc. Natl. Acad. Sci, USA* 83:5939–5942. The cDNA sequence encoding the complete A2 domain of porcine factor VIII and predicted amino acid sequence and hybrid human/porcine factor VIII having substitutions of all domains, all subunits, and specific amino acid sequences were disclosed in U.S. Ser. No. 07/864,004 entitled "Hybrid Human/Porcine factor VIII" filed Apr. 7, 1992 by John S. Lollar and Marschall S. Runge, which issued as U.S. Pat. No. 5,364,771 on Nov. 15, 1994, and in WO 93/20093. The cDNA sequence encoding the A2 domain of porcine factor VIII having sequence identity to residues 373–740 in mature human factor VIII, as shown in SEQ ID NO: 1, and the predicted amino acid sequence are shown in SEQ ID NOs:3 and 4, respectively. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503. The entire nucleotide sequence encoding porcine factor VIII, including the complete A1 domain, activation peptide, A3, C1 and C2 domains, as well as the encoded amino acid sequence, is disclosed in U.S. Pat. No. 5,859,204, issued Jan. 12, 1999.

Both porcine and human factor VIII are isolated from plasma as a two subunit protein. The subunits, known as the heavy chain and light chain, are held together by a non-covalent bond that requires calcium or other divalent metal ions. The heavy chain of factor VIII contains three domains, A1, A2, and B, which are linked covalently. The light chain of factor VIII also contains three domains, designated A3, C1, and C2. The B domain has no known biological function and can be removed, or partially removed from the molecule proteolytically or by recombinant DNA technology methods without significant alteration in any measurable parameter of factor VIII. Human recombinant factor VIII has a similar structure and function to plasma-derived factor VIII, though it is not glycosylated unless expressed in mammalian cells.

Both human and porcine activated factor VIII ("factor VIIIa") have three subunits due to cleavage of the heavy chain between the A1 and A2 domains. This structure is designated A1/A2/A3-C1-C2. Human factor VIIIa is not stable under the conditions that stabilize porcine factor VIIIa, presumably because of the weaker association of the A2 subunit of human factor VIIIa. Dissociation of the A2 subunit of human and porcine factor VIIIa is associated with loss of activity in the factor VIIIa molecule. Yakhyaev, A. et al. (1997) *Blood* 90:Suppl. 1, Abstract #126, reported binding of A2 domain by low density lipoprotein receptor-related protein, suggesting that cellular uptake of A2 mediated by such binding acts to down-regulate factor VIII activity.

Specifically provided as an exemplary embodiment is active recombinant hybrid human/porcine factor VIII having substituted A2 domain, the nucleic acid sequence encoding it, and the methods for preparing, isolating, and characterizing its activity. The methods by which this hybrid construct is prepared can also be used to prepare active recombinant hybrid human/porcine factor VIII or fragments thereof having substitution of subunits, continuous parts of domains, or domains other than A2. One skilled in the art will recognize that these methods also demonstrate how other recombinant hybrid human/non-human, non-porcine mammalian or animal/animal hybrid factor VIII molecules or fragments thereof can be prepared in which subunits, domains, or continuous parts of domains are substituted.

Recombinant hybrid human/porcine factor VIII is prepared starting with human cDNA (Biogen, Inc.) or porcine cDNA (described herein) encoding the relevant factor VIII sequence. In a preferred embodiment, the factor VIII encoded by the cDNA includes domains A1-A2-A3-C1-C2, lacking the entire B domain, and corresponds to amino acid residues 1–740 and 1649–2332 of single chain human factor VIII (see SEQ ID NO:2), according to the numbering system of Wood et al. (1984) Nature 312:330–337.

Individual subunits, domains, or continuous parts of domains of porcine or human factor VIII cDNA can be and have been cloned and substituted for the corresponding human or porcine subunits, domains, or parts of domains by established mutagenesis techniques. For example, Lubin, I. M. et al. (1994) J. Biol. Chem. 269(12):8639–8641 describes techniques for substituting the porcine A2 domain for the human domain using convenient restriction sites. Other methods for substituting any arbitrary region of the factor VIII cDNA of one species for the factor VIII cDNA of another species include splicing by overlap extension ("SOE"), as described by Horton, R. M. et al. (1993) Meth. Enzymol 217:270–279.

The hybrid factor VIII cDNA encoding subunits, domains, or parts of domains or the entire hybrid cDNA molecules are cloned into expression vectors for ultimate expression of active hybrid human/porcine factor VIII protein molecules in cultured cells by established techniques, as described by Selden, R. F., "Introduction of DNA into mammalian cells," in Current Protocols in Molecular Biology, F. M. Ausubel et al., eds (1991).

In a preferred embodiment, a hybrid human/porcine cDNA encoding factor VIII, in which the porcine sequence encodes a domain or part domain, such as the A2 domain or part domain, is inserted in a mammalian expression vector, such as ReNeo, to form a hybrid factor VIII construct. Preliminary characterization of the hybrid factor VIII is accomplished by insertion of the hybrid cDNA into the ReNeo mammalian expression vector and transient expression of the hybrid protein in COS-7 cells. A determination of whether active hybrid protein is expressed can then be made. The expression vector construct is used further to stably transfect cells in culture, such as baby hamster kidney cells, using methods that are routine in the art, such as liposome-mediated transfection (LIPOFECTIN™, Life Technologies, Inc., Gaithersburg, Md.). Expression of recombinant hybrid factor VIII protein can be confirmed, for example, by sequencing, Northern and Western blotting, or polymerase chain reaction (PCR). Hybrid factor VIII protein in the culture media in which the transfected cells stably expressing the protein are maintained can be precipitated, pelleted, washed, and resuspended in an appropriate buffer, and the recombinant hybrid factor VIII protein purified by standard techniques, including immunoaffinity chromatography using, for example, monoclonal anti-A2-Sepharose™ (Pharmacia, Piscatway, N.J.).

In a further embodiment, the hybrid factor VIII comprising subunit, domain, or amino acid sequence substitutions is expressed as a fusion protein from a recombinant molecule in which sequence encoding a protein or peptide that enhances, for example, stability, secretion, detection, isolation, or the like is inserted in place adjacent to the factor VIII encoding sequence. Established protocols for use of homologous or heterologous species expression control sequences including, for example, promoters, operators, and regulators, in the preparation of fusion proteins are known and routinely used in the art. See Current Protocols in Molecular Biology (Ausubel, F. M., et al., eds), Wiley Interscience, N.Y. Expression is enhanced by including portions of the B-domain. In particular, the inclusion of those parts of the B domain designated "SQ" [Lind, P. et al. (1995) supra] results in favorable expression. "SQ" constructs lack all of the human B domain except for 5 amino acids of the B domain N-terminus and 9 amino acids of the B domain C-terminus.

The purified hybrid factor VIII or fragment thereof can be assayed for immunoreactivity and coagulation activity by standard assays including, for example, the plasma-free factor VIII assay, the one-stage clotting assay, and the enzyme-linked immunosorbent assay using purified recombinant human factor VIII as a standard.

Other vectors, including both plasmid and eukaryotic viral vectors, may be used to express a recombinant gene construct in eukaryotic cells depending on the preference and judgment of the skilled practitioner (see, for example, Sambrook et al., Chapter 16). Other vectors and expression systems, including bacterial, yeast, and insect cell systems, can be used but are not preferred due to differences in, or lack of, glycosylation.

Recombinant hybrid factor VIII protein can be expressed in a variety of cells commonly used for culture and recombinant mammalian protein expression. In particular, a number of rodent cell lines have been found to be especially useful hosts for expression of large proteins. Preferred cell lines, available from the American Type Culture Collection, Rockville, Md., include baby hamster kidney cells, and chinese hamster ovary (CHO) cells which are cultured using routine procedures and media.

The same methods employed for preparing hybrid human/porcine factor VIII having subunit, domain, or amino acid sequence substitution can be used to prepare other recombinant hybrid factor VIII protein and fragments thereof and the nucleic acid sequences encoding these hybrids, such as human/non-human, non-porcine mammalian or animal/animal. Starting with primers from the known human DNA sequence, the murine and part of the porcine factor VIII cDNA have been cloned. Factor VIII sequences of other species for use in preparing a hybrid human/animal or animal/animal factor VIII molecule can be obtained using the known human and porcine DNA sequences as a starting point. Other techniques that can be employed include PCR amplification methods with animal tissue DNA, and use of a cDNA library from the animal to clone out the factor VIII sequence.

As an exemplary embodiment, hybrid human/mouse factor VIII protein can be made as follows. DNA clones corresponding to the mouse homolog of the human factor VIII gene have been isolated and sequenced and the amino acid sequence of mouse factor VIII protein predicted, as described in Elder, G., et al. (1993) Genomics 16(2)

:374–379, which also includes a comparison of the predicted amino acid sequences of mouse, human, and part of porcine factor VIII molecules. The mouse factor VIII cDNA sequence and predicted amino acid sequence are shown in SEQ ID NO:5 and SEQ ID NO:8, respectively. In a preferred embodiment, the RNA amplification with transcript sequencing (RAWTS) methods described in Sarkar, G. et al. (1989) *Science* 244:331–334, can be used. Briefly, the steps are (1) cDNA synthesis with oligo(dT) or an mRNA-specific oligonucleotide primer; (2) polymerase chain reaction (PCR) in which one or both oligonucleotides contains a phage promoter attached to a sequence complementary to the region to be amplified; (3) transcription with a phage promoter; and (4) reverse transcriptase-mediated dideoxy sequencing of the transcript, which is primed with a nested (internal) oligonucleotide. In addition to revealing sequence information, this method can generate an in vitro translation product by incorporating a translation initiation signal into the appropriate PCR primer: and can be used to obtain novel mRNA sequence information from other species.

Substitution of Amino Acid(s):

The present invention provides active recombinant hybrid human/animal and animal/animal factor VIII molecules or fragments thereof comprising at least one sequence including one or more unique amino acids of one species substituted for the corresponding amino acid sequence of the other species or fragments thereof, nucleic acid sequences encoding these hybrids, methods for preparing and isolating them, and methods for characterizing their coagulant, immunogenic and immunoreactive properties.

The A2 domain is necessary for the procoagulant activity of the factor VIII molecule. Studies show that porcine factor VIII has six-fold greater procoagulant activity than human factor VIII (Lollar, P. et al. (1991) *J. Biol. Chem.* 266:12481–12486, and that the difference in coagulant activity between human and porcine factor VIII appears to be based on a difference in amino acid sequence between one or more residues in the human and porcine A2 domains (Lollar, P. et al. (1992) *J. Biol. Chem.* 267:23652–23657. Further, the A2 and C2 domains and possibly a third light chain region in the human factor VIII molecule are thought to harbor the epitopes to which most, if not all, inhibitory antibodies react, according to Hoyer (1994) *Semin. Hewatol.* 31:1–5.

Recombinant hybrid human/animal, animal/animal, or equivalent factor VIII molecules or fragments thereof can be made by substitution of at least one specific sequence including one or more unique amino acids from the A2, C2, and/or other domains of the factor VIII of one species for the corresponding sequence of the other species, wherein the amino acid sequences differ, as illustrated in more detail below, between the molecules of the two species. In an exemplary preferred embodiment described herein, the present invention provides active recombinant hybrid human/porcine factor VIII comprising porcine amino acid sequence substituted for corresponding human amino acid sequence that includes an epitope, wherein the hybrid factor VIII has decreased or no immunoreactivity with inhibitory antibodies to factor VIII. In a further embodiment, active recombinant hybrid factor VIII molecules can also be made comprising amino acid sequence from more than one species substituted for the corresponding sequence in a third species. Recombinant hybrid equivalent molecules can also be made, comprising human, animal, or hybrid factor VIII including at least one sequence including one or more amino acids that have no known sequence identity to factor VIII, as further described below.

Any hybrid factor VIII construct having specific amino acid substitution as described can be assayed by standard procedures for coagulant activity and for reactivity with inhibitory antibodies to factor VIII for identification of hybrid factor VIII molecules with enhanced coagulant activity and/or decreased antibody immunoreactivity. Hybrid molecules may also be identified that have reduced coagulant activity compared to human or porcine factor VIII but also have decreased antibody reactivity. One skilled in the art will recognize that hybrid factor VIII molecules or fragments thereof having less, equal, or greater coagulant activity, compared to human or porcine factor VIII, are useful for treating patients who have a factor VIII deficiency. The methods described herein to prepare active recombinant hybrid human/porcine factor VIII with substitution of specific amino acids can be used to prepare active recombinant hybrid human/non-human, non-porcine mammalian factor VIII protein, hybrid animal-1/animal-2 factor VIII, and hybrid equivalent factor VIII or fragments thereof.

Hybrid Factor VIII Molecules with Altered Coagulant Activity:

The present invention provides procoagulant recombinant hybrid human/animal, animal/animal, or equivalent factor VIII molecules or fragments thereof comprising at least one specific sequence including one or more unique amino acids having procoagulant activity in the factor VIII of one species substituted for the corresponding amino acid sequence of the factor VIII of the other species, using established site-directed mutagenesis techniques as described herein. The specific sequences to be used in the substitution are selected and the hybrid constructs are prepared and assayed for coagulant activity, as follows. Specifically provided as a preferred and exemplary embodiment is a hybrid human/porcine factor VIII comprising amino acid substitutions in the A2 domain. It is understood that one skilled in the art can use these methods to prepare other hybrid human/animal, animal/animal, and equivalent factor VIII molecules or fragments thereof having altered coagulant activity, preferably increased coagulant activity compared to human factor VIII.

The basis for the greater coagulant activity in porcine factor VIII appears to be the more rapid spontaneous dissociation of the A2 subunit of human factor VIIIa than porcine factor VIIIa, which leads to loss of activity, according to Lollar, P. et al. (1990) *J. Biol. Chem.* 265:1688–1692; Lollar, P. et al. (1992) *J. Biol. Chem.* 267:23652–23657; Fay, P. J. et al. (1992) *J. Biol. Chem.* 267:13246–13250.

A comparison of the alignment of the amino acid sequences of the human and porcine factor VIII A2 domains (residue numbering starts at position 373 with respect to the full length amino acid sequence of human factor VIII, SEQ ID NO:2) is shown in FIG. 1C. For preparation of a hybrid human/porcine factor VIII molecule with altered coagulant activity, the initial target candidates for mutagenesis, which were revealed upon comparison of the human and porcine A2 amino acid sequences (SEQ ID NOs: 2 and 6, respectively) within the human A2 domain, are shown in Table I.

TABLE I

HUMAN AMINO ACID SEQUENCE TARGET CANDIDATES FOR MUTAGENESIS (SEQ ID NO:2)

| Sequence | Residues | Mismatches | Charge Changes |
|---|---|---|---|
| 398–403 | 6 | 4 | 1 |
| 434–444 | 10 | 4 | 3 |
| 484–496 | 13 | 7 | 3 |
| 598–603 | 6 | 4 | 2 |
| 536–541 | 6 | 4 | 0 |
| 713–722 | 10 | 6 | 2 |
| 727–737 | 11 | 6 | 2 |

Table I and FIGS. 1A–1B illustrate seven sequences in the human and pig A2 domain amino acid sequences (SEQ ID NOs:2 and 6, respectively) that constitute only 17% of the A2 domain but include 70% of the sequence differences between human and porcine A2 domains.

A recombinant hybrid human/porcine construct is described in which amino acids Ser373-Glu604 in the A2 domain (Ser373-Arg740) of human factor VIII have been replaced with the homologous porcine sequence. This construct does not react with A2 inhibitors and has the same coagulant activity as human B(−) factor VIII. A plasma-derived hybrid molecule is described that comprises a complete porcine A2 domain substitution in the human factor VIII that has increased coagulant activity compared to human factor VIII. Comparison of these constructs indicates that a region between residues Asp605 and Arg740 is responsible for the difference in activity between human and porcine factor VIII. This region can be defined more specifically by systematically making recombinant hybrid human/porcine factor VIII molecules with porcine substitutions in the region between Asp605 and Arg740 by using established site-directed mutagenesis techniques, for example, the "splicing by overlap extension" (SOE) method that has been used extensively to make hybrid factor VIII molecules containing porcine substitutions in the NH$_2$-terminal region of A2. These molecules can be expressed in COS-7 cells and baby hamster kidney cells as described above. They can be purified to homogeneity using methods known in the art, such as heparin-Sepharose™ and immunoaffinity chromatography. Protein concentration can be estimated by absorption of ultraviolet light at A$_{280}$, and the specific activity of the constructs can be determined by dividing coagulant activity (measured in units per ml by single stage clotting assay) by A$_{280}$. Human factor VIII has a specific activity of approximately 3000–4000 U/A$_{280}$, whereas porcine factor VIII has a specific activity of approximately 20,000 U/A$_{280}$. In a preferred embodiment, the procoagulant recombinant hybrid human/porcine factor VIII has a specific activity of 20,000 U/A$_{280}$ and contains a minimal amount of porcine substitution in the A2 domain.

As described herein, site-directed mutagenesis techniques are used to identify hybrid protein with coagulant activity that can be enhanced, equal to, or reduced, compared to human factor VIII, but preferably is enhanced. In the hybrid human/porcine embodiment, specific human sequences are replaced with porcine sequences, preferably using the splicing by overlap extension method (SOE), as described by Ho, S. N., et al., 77 Gene 51–59 (1994), and in Examples 7 and 8. Oligonucleotide-directed mutagenesis can also be used, as was done to loop out the amino acid sequence for part of the human A2 domain (see Example 7). As functional analysis of the hybrids reveals coagulant activity, the sequence can be further dissected and mapped for procoagulant sequence by standard point mutation analysis techniques.

The present invention contemplates that hybrid factor VIII cDNA and protein can be characterized by methods that are established and routine, such as DNA sequencing, coagulant activity assays, mass by ELISA and by UV absorbance at 280 nm of purified hybrid factor VIII, specific coagulant activity (U/mg), SDS-PAGE of purified hybrid factor VIII, and the like. Other known methods of testing for clinical effectiveness may be required, such as amino acid, carbohydrate, sulfate, or metal ion analysis.

A recombinant hybrid factor VIII having superior coagulant activity, compared to human factor VIII, may be less expensive to make than plasma-derived factor VIII and may decrease the amount of factor VIII required for effective treatment of factor VIII deficiency.

Hybrid Factor VIII Molecules with Reduced Immunoreactivity:

Epitopes that are immunoreactive with antibodies that inhibit the coagulant activity of factor VIII ("inhibitors" or "inhibitory antibodies") have been characterized based on known structure-function relationships in factor VIII. Presumably, inhibitors could act by disrupting any of the macromolecular interactions associated with the domain structure of factor VIII or its associations with von Willebrand factor, thrombin, factor Xa, factor IXa, or factor X. However, over 90% of inhibitory antibodies to human factor VIII act by binding to epitopes located in the 40 kDa A2 domain or 20 kDa C2 domain of factor VIII, disrupting specific functions associated with these domains, as described by Fulcher et al. (1985) Proc. Natl. Acad. Sci USA 82:7728–7732; and Scandella et al. (1988) Proc. Natl. Acad. Sci. USA 85:6152–6156. In addition to the A2 and C2 epitopes, there may be a third epitope in the A3 or C1 domain of the light chain of factor VIII, according to Scandella et al. (1993) Blood 82:1767–1775. The significance of this putative third epitope is unknown, but it appears to account for a minor fraction of the epitope reactivity in factor VIII.

Anti-A2 antibodies block factor X activation, as shown by Lollar et al. (1994) J. Clin. Invest. 93:2497–2504. Previous mapping studies by deletion mutagenesis described by Ware et al. (1992) Blood Coagul. Fibrinolysis 3:703–716, located the A2 epitope to within a 20 kDa region of the NH$_2$-terminal end of the 40 kDa A2 domain. Competition immunoradiometric assays have indicated that A2 inhibitors recognize either a common epitope or narrowly clustered epitopes, as described by Scandella et al. (1992) Throm. Haemostas 67:665–671, and as demonstrated in Example 8.

The present invention provides active recombinant hybrid and hybrid equivalent factor VIII molecules or fragments thereof, the nucleic acid sequences encoding these hybrids, methods of preparing and isolating them, and methods for characterizing them. These hybrids comprise human/animal, animal/animal, or equivalent hybrid factor VIII molecules, further comprising at least one specific amino acid sequence including one or more unique amino acids of the factor VIII of one species substituted for the corresponding amino acid sequence of the factor VIII of the other species; or comprises at least one sequence including one or more amino acids having no known sequence identity to factor VIII substituted for specific amino acid sequence in human, animal, or hybrid factor VIII. The resulting hybrid factor VIII has reduced or no immunoreactivity to factor VIII inhibitory antibodies, compared to human or porcine factor VIII.

Using the approach described in the previous section for substitution of amino acids in the factor VIII molecule, mutational analysis is employed to select corresponding factor VIII amino acid sequence of one species, preferably porcine, which is substituted for at least one sequence including one or more amino acids in the factor VIII of another species, preferably human, or for amino acid sequence of a hybrid equivalent factor VIII molecule, that includes one or more critical region(s) in the A2, C2, or any other domain to which inhibitory antibodies are directed. The methods are described in more detail below. The resulting procoagulant recombinant hybrid construct has reduced or no immunoreactivity to inhibitory antibodies, compared to human factor VIII, using standard assays. Through systematic substitution of increasingly smaller amino acid sequences followed by assay of the hybrid construct for immunoreactivity, as described below, the epitope in any domain of a factor VIII molecule is mapped, substituted by amino acid sequence having less or no immunoreactivity, and a hybrid factor VIII is prepared.

It is understood that one skilled in the art can use this approach combining epitope mapping, construction of hybrid factor VIII molecules, and mutational analysis of the constructs to identify and replace at least one sequence including one or more amino acids comprising an epitope in the A2, C2, and/or other domains to which inhibitory antibodies are directed and to construct procoagulant recombinant hybrid human/animal, animal/animal, or equivalent factor VIII or fragments thereof having decreased or no immunoreactivity compared to human or porcine factor VIII. This approach is used, as described in Example 8, to prepare a recombinant procoagulant hybrid human/porcine factor VIII having porcine amino acid substitutions in the human A2 domain and no antigenicity to anti-factor VIII antibodies as an exemplary embodiment.

Usually, porcine factor VIII has limited or no reaction with inhibitory antibodies to human factor VIII. The recombinant hybrid human/porcine factor VIII molecules having decreased or no reactivity with inhibitory antibodies based on amino acid substitution in the A2 domain are prepared, as an example of how hybrid factor VIII can be prepared using the factor VIII of other species and substitutions in domains other than A2, as follows. The porcine A2 domain is cloned by standard cloning techniques, such as those described above and in Examples 6, 7, and 8, and then cut and spliced within the A2 domain using routine procedures, such as using restriction sites to cut the cDNA or splicing by overlap extension (SOE). The resulting porcine amino acid sequence is substituted into the human A2 domain to form a hybrid factor VIII construct, which is inserted into a mammalian expression vector, preferably ReNeo, stably transfected into cultured cells, preferably baby hamster kidney cells, and expressed, as described above. The hybrid factor VIII is assayed for immunoreactivity, for example with anti-A2 antibodies by the routine Bethesda assay or by plasma-free chromogenic substrate assay. The Bethesda unit (BU) is the standard method for measuring inhibitor titers. If the Bethesda titer is not measurable (<0.7 BU/mg IgG) in the hybrid, then a human A2 epitope was eliminated in the region of substituted corresponding porcine sequence. The epitope is progressively narrowed, and the specific A2 epitope can thus be determined to produce a hybrid human/porcine molecule with as little porcine sequence as possible. As described herein, a 25-residue sequence corresponding to amino acids Arg484-Ile508 that is critical for inhibitory immunoreactivity has been identified and substituted in the human A2 domain. Within this sequence are only nine differences between human and porcine factor VIII. This region can be further analyzed and substituted.

Hybrid human/porcine factor VIII molecules having decreased or no reactivity with inhibitory antibodies based on substitution of amino acid sequence in the C1, C2 or other domain, with or without substitution in the A2 domain, can also be prepared. The C2 epitope, for example can be mapped using the homolog scanning approach combined with site-directed mutagensesis. More specifically, the procedures can be the same or similar to those described herein for amino acids substitution in the A2 domain, including cloning the porcine C2 or other domain, for example by using RT-PCR or by probing a porcine liver cDNA library with human C2 or other domain DNA; restriction site techniques and/or successive SOE to map and simultaneously replace epitopes in the C2 or other domain; substitution for the human C2 or other domain in B(−) factor VIII; insertion into an expression vector, such as pBluescript; expression in cultured cells; and routine assay for immunoreactivity. For the assays, the reactivity of C2 hybrid factor VIII with a C2-specific inhibitor, MR [Scandella et al. (1992) *Thomb. Haemostasis* 67:665–671 and Lubin et al. (1994)], and/or other C2 specific antibodies prepared by affinity chromatography can be performed.

The C2 domain consists of amino acid residues 2173–2332 (SEQ ID NO:2). Within this 154 amino acid region, inhibitor activity appears to be directed to a 65 amino acid region between residues 2248 and 2312, according to Shima, M. et al. (1993) *Thromb. Haemostas* 69:240–246. If the C2 sequence of human and porcine factor VIII is approximately 85% identical in this region, as it is elsewhere in the functionally active regions of factor VIII, there will be approximately ten differences between human and porcine factor VIII C2 amino acid sequence, which can be used as initial targets to construct hybrids with substituted C2 sequence.

It is likely that clinically significant factor VIII epitopes are confined to the A2 and C2 domains. However, if antibodies to other regions (A1, A3, B, or C1 domains) of factor VIII are identified, the epitopes can be mapped and eliminated by using the approach described herein for the nonantigenic hybrid human/porcine factor VIII molecules.

More specifically, mapping of the putative second light chain epitope and/or any other epitope in any other animal or human factor VIII domain can also be accomplished. Initially, determination of the presence of a third inhibitor epitope in the A3 or C1 domains can be made as follows. Using human ("H") and porcine ("p") factor VIII amino acid sequences as a model, $A1_p$-$A2_p$-$A3_p$-$C1_H$-$C2_p$ and $A1_p$-$A2_p$-$A3_H$-$C1_p$-$C2_p$ B-domainless hybrids will be constructed. Inhibitor IgG from approximately 20 patient plasmas (from Dr. Dorothea Scandella, American Red Cross) who have low or undetectable titers against porcine factor VIII will be tested against the hybrids. If the third epitope is in the A3 domain, inhibitory IgG is expected to react with $A1_p$-$A2_p$-$A3_H$-$C1_p$-$C2_p$ but not $A1_p$-$A2_p$-$A3_p$-$C1_H$-$C2_p$. Conversely, if the third epitope is in the C1 domain, then inhibitory IgG is expected to react with $A_{1p}$-A2p-$A3_p$-$C1_H$-$C2_p$ but not $A1_p$-$A2_p$-$A3_H$-$C1_p$-$C2_p$. If a third epitope is identified it will be characterized by the procedures described herein for the A2 and C2 epitopes.

For example, antibodies specific for the C1 or A3 domain epitope can be isolated from total patient IgG by affinity chromatography using the $A1_p$-$A2_p$-$A3_H$-$C1_p$-$C2_p$ and $A1_p$-$A2_p$-$A3_p$-$C1_H$-$C2_p$ hybrids, and by elimination of C2 specific antibodies by passage over recombinant factor VIII C2-SEPHAROSE™ (Pharmacia, Piscatway, N.J.). The putative third epitope will be identified by SOE constructs in which, in a preferred embodiment, portions of the human factor VIII A3 or C1 domain are systematically replaced with porcine sequence.

Hybrid Factor VIII Molecules with Reduced Immunogenicity:

A molecule is immunogenic when it can induce the production of antibodies in human or animal. The present invention provides a procoagulant recombinant hybrid human/animal or animal/animal factor VIII molecule, hybrid factor VIII equivalent molecule, or fragment of either that is less immunogenic than wild-type human porcine factor VIII in human or animal, comprising at least one specific amino acid sequence including one or more unique amino acids of the factor VIII of one species substituted for the corresponding amino acid sequence that has immunogenic activity of the factor VIII of the other species; or at least one amino acid sequence including one or more amino acids having no known identity to factor VIII substituted for amino acid sequence of the human, animal, or hybrid factor. This hybrid can be used to lower the incidence of inhibitor development in an animal or human and to treat factor VIII deficiency, and would be preferred in treating previously untreated patients with hemophilia. In a preferred embodiment, a modified factor VIII comprises human factor VIII amino acid sequence, further comprising one or more alanine residues substituted for human amino acid sequence having immunogenic activity, resulting in a procoagulant recombinant hybrid equivalent molecule or fragment thereof having reduced or no immunogenicity in human or animal.

The process described herein of epitope mapping and mutational analysis combined with substitution of non-antigenic amino acid sequence in a factor VIII molecule, using hybrid human/porcine factor VIII, produces hybrid molecules with low antigenicity. Using this model and the associated methods, any of the hybrid constructs described herein can be altered by site-directed mutagenesis techniques to remove as much of any functional epitope as possible to minimize the ability of the immune system to recognize the hybrid factor VIII, thereby decreasing its immunogenicity.

One method that can be used to further reduce the antigenicity and to construct a less immunogenic hybrid factor VIII is alanine scanning mutagenesis, described by Cunningham, B. C. et al. (1989) *Science* 244:1081–1085, of selected specific amino acid sequences in human, animal, or hybrid equivalent factor VIII. In alanine scanning mutagenesis, amino acid side chains that are putatively involved in an epitope are replaced by alanine residues by using site-directed mutagenesis. By comparing antibody binding of alanine mutants to wild-type protein, the relative contribution of individual side chains to the binding interaction can be determined. Alanine substitutions are likely to be especially useful, since side chain contributions to antibody binding are eliminated beyond the β carbon, but, unlike glycine substitution, main chain conformation is not usually altered. Alanine substitution does not impose major steric, hydrophobic or electrostatic effects that dominate protein-protein interactions.

In protein antigen-antibody interactions, there usually are about 15–20 antigen side chains in contact with the antibody. Side chain interactions, as opposed to main chain interactions, dominate protein-protein interactions. Recent studies have suggested that only a few (approximately 3 to 5) of these side chain interactions contribute most of the binding energy. See Clackson, T. et al. (1995) *Science* 267:383–386. An extensive analysis of growth hormone epitopes for several murine monoclonal antibodies revealed the following hierarchy for side chain contributions to the binding energy: Arg>Pro>Glu-Asp-Phe-Ile, with Trp, Ala, Gly, and Cys not tested [Jin, L. et al. (1992) *J. Mol. Biol.* 226:851–865]. Results with the A2 epitope described herein are consistent with this, since twelve of the 25 residues in the 484–508 A2 segment contain these side chains (FIG. 1C).

The finding that certain amino acid residues are particularly well recognized by antibodies, indicates that elimination of these residues from a known epitope can decrease the ability of the immune system to recognize these epitopes, i.e., can make a molecule less immunogenic. In the case of the A2 epitope, immunogenic residues can be replaced without loss of factor VIII coagulant activity. For example, in HP9, Arg484 is replaced by Ser, Pro485 is replaced by Ala, Arg489 is replaced by Gly, Pro492 is replaced by Leu, and Phe501 is replaced by Met. Further, results from the patient plasmas used to test immunoreactivity in hybrid human/porcine factor VIII constructs, described in Example 8, indicate that antibodies from different patients recognize the same or a very similar structural region in the A2 domain and that the residues in the A2 domain that participate in binding A2 inhibitors appear to show little variation. Thus, the A2 epitope included in human factor VIII residues 484–508 is an immunodominant epitope in that it is recognized by the human immune system better than other structural regions of factor VIII. Replacing this structure by nonantigenic factor VIII sequence from another species or by non-factor VIII amino acid sequence, while retaining full procoagulant activity, is expected to alter recognition of hybrid or hybrid equivalent factor VIII by the immune system.

It is anticipated that site-directed mutagenesis to replace bulky and/or charged residues that tend to dominate epitopes with small, neutral side chains (e.g., alanine) may produce a less immunogenic region. It is expected that a molecule containing a few of these substitutions at each significant inhibitor epitope will be difficult for the immune system to fit by the lock-and-key mechanism that is typical of antigen-antibody interactions. Because of its low antigenicity, such a hybrid molecule could be useful in treating factor VIII deficiency patients with inhibitors, and because of its low immunogenicity, it could be useful in treating previously untreated patients with hemophilia A.

A general result is that mutation of one of a few key residues is sufficient to decrease the binding constant for a given protein-protein interaction by several orders of magnitude. Thus, it appears likely that all factor VIII epitopes contain a limited number of amino acids that are critical for inhibitor development. For each epitope in factor VIII, alanine substitutions for at least one sequence including one or more specific amino acids having immunogenic activity, may produce an active molecule that is less immunogenic than wild-type factor VIII. In a preferred embodiment, the hybrid factor VIII is B-domainless.

The methods for preparing active recombinant hybrid or hybrid equivalent factor VIII with substitution of amino acid sequence having little or no immunogenic activity for amino acid sequence in the factor VIII having immunogenic activity are as follows, using hybrid human/porcine factor VIII with amino acid substitutions in the A2 domain as an exemplary embodiment. There are 25 residues in the human factor VIII region 484–508. Site-directed mutagenesis can be used to make single mutants in which any of these residues is replaced by any of the other 19 amino acids for a total of 475 mutants. Furthermore, hybrid molecules having more than one mutation can be constructed.

The hybrid constructs can be assayed for antigenicity by measuring the binding constant for inhibitor antibodies, as described by Friguet, B. et al. (1985) *J. Immunol. Methods* 77:305–319 (1985). In a preferred embodiment, the binding constant will be reduced by at least three orders of magnitude, which would lower the Bethesda titer to a level that is clinically insignificant. For example, the IC50 (a crude measure of the binding constant) of inhibition by A2 antibodies was reduced in hybrid human/porcine factor VIII constructs HP2, HP4, HP5, HP7, and HP9, described in Example 8, and this was associated with a reduction in Bethesda titer to an unmeasurable level. It is anticipated, for example, that a double or triple alanine mutant of human factor VIII (e.g., a human factor VIII Arg484->Ala, Arg489->Ala, Phe501->Ala triple mutant) will produce a molecule with sufficiently low antigenicity for therapeutic use. Similar mutations can be made in the C2 epitope and the putative third epitope. A preferred embodiment comprises two or three alanine substitutions into two or three factor VIII epitopes. Other substitutions into these regions can also be done.

In a preferred embodiment, hybrid equivalent factor VIII molecules will be identified that are less antigenic and/or immunogenic in human and animal than either human or porcine factor VIII. Such hybrid equivalent constructs can be tested in animals for their reduced antigenicity and/or immunogenicity. For example, control and factor VIII deficient rabbits, pigs, dogs, mice, primates, and other mammals can be used as animal models. In one experimental protocol, the hybrid or hybrid equivalent factor VIII can be administered systematically over a period of six months to one year to the animal, preferably by intravenous infusion, and in a dosage range between 5 and 50 Units/kg body weight, preferably 10–50 Units/kg, and most preferably 40 Units/kg body weight. Antibodies can be measured in plasma samples taken at intervals after the infusions over the duration of the testing period by routine methods, including immunoassay and the Bethesda assay. Coagulant activity can also be measured in samples with routine procedures, including a one-stage coagulation assay.

The hybrid equivalent factor VIII molecules can be tested in humans for their reduced antigenicity and/or immunogenicity in at least two types of clinical trials. In one type of trial, designed to determine whether the hybrid or hybrid equivalent factor VIII is immunoreactive with inhibitory antibodies, hybrid or hybrid equivalent factor VIII is administered, preferably by intravenous infusion, to approximately 25 patients having factor VIII deficiency who have antibodies to factor VIII that inhibit the coagulant activity of therapeutic human or porcine factor VIII. The dosage of the hybrid or hybrid equivalent factor VIII is in a range between 5 and 50 Units/kg body weight, preferably 10–50 Units/kg, and most preferably 40 Units/kg body weight. Approximately 1 hour after each administration, the recovery of factor VIII from blood samples is measured in a one-stage coagulation assay. Samples are taken again approximately 5 hours after infusion, and recovery is measured. Total recovery and the rate of disappearance of factor VIII from the samples is predictive of the antibody titer and inhibitory activity. If the antibody titer is high, factor VIII recovery usually cannot be measured. The recovery results are compared to the recovery of recovery results in patients treated with plasma-derived human factor VIII, recombinant human factor VIII, porcine factor VIII, and other commonly used therapeutic forms of factor VIII or factor VIII substitutes.

In a second type of clinical trial, designed to determine whether the hybrid or hybrid equivalent factor VIII is immunogenic, i.e., whether patients will develop inhibitory antibodies, hybrid or hybrid equivalent factor VIII is administered, as described in the preceding paragraph, to approximately 100 previously untreated hemophiliac patients who have not developed antibodies to factor VIII. Treatments are given approximately every 2 weeks over a period of 6 months to 1 year. At 1 to 3 month intervals during this period, blood samples are drawn and Bethesda assays or other antibody assays are performed to determine the presence of inhibitory antibodies. Recovery assays can also be done, as described above, after each infusion. Results are compared to hemophiliac patients who receive plasma-derived human factor VIII, recombinant human factor VIII, porcine factor VIII, or other commonly used therapeutic forms of factor VIII or factor VIII substitutes.

Preparation of Hybrid Factor VIII Molecules Using Human and Non-porcine, Non-human Mammalian Factor VIII Amino Acid Sequence:

The methods used to prepare hybrid human/porcine factor VIII with substitution of specific amino acids can be used to prepare recombinant hybrid human/non-human, non-porcine mammalian or animal/animal factor VIII protein that has, compared to human or porcine factor VIII, altered or the same coagulant activity and/or equal or reduced immunoreactivity and/or immunogenicity, based on substitution of one or more amino acids in the A2, C2, and/or other domains.

Similar comparisons of amino acid sequence identity can be made between human and non-human, non-porcine mammalian factor VIII proteins to determine the amino acid sequences in which procoagulant activity, anti-A2 and anti-C2 immunoreactivity, and or immunogenicity, or immunoreactivity and/or immunogenicity in other domains reside. Similar methods can then be used to prepare hybrid human/non-human, non-porcine mammalian factor VIII molecules. As described above, functional analysis of each hybrid will reveal those with decreased reactivity to inhibitory antibodies, and/or reduced immunogenicity, and/or increased coagulant activity, and the sequence can be further dissected by point mutation analysis.

For example, hybrid human/mouse factor VIII molecules can be prepared as described above. The amino acid sequence alignment of the A2 domain of human (SEQ ID NO:2) and mouse (SEQ ID NO:6) is shown in FIG. 1C. As reported by Elder et al., the factor VIII protein encoded by the mouse cDNA (SEQ ID NO:5) has 2319 amino acids, with 74% sequence identity overall to the human sequence (SEQ ID NO:2) (87% identity when the B domain is excluded from the comparison), and is 32 amino acids shorter than human factor VIII. The amino acid sequences in the mouse A and C domains (SEQ ID NO:6) are highly conserved, with 84–93% sequence identity to the human sequence (SEQ ID NO:2), while the B and the two short acidic domains have 42–70% sequence identity. Specifically, the A1, A2, and A3 mouse amino acid sequences (SEQ ID NO: 6) are 85, 85, and 90% identical to the corresponding human amino acid sequences (SEQ ID NO:2). The C1 and C2 mouse amino acid sequences are 93 and 84% identical to the corresponding human amino acid sequences. In the predicted mouse factor VIII amino acid sequence (SEQ ID NO: 6), the A1, A2, and A3 domains are homologous to human factor VIII amino acids 1–372, 373–740, and 1690–2032, respectively, using amino acid sequence identity for numbering purposes.

The thrombin/factor Xa and all but one activated protein C cleavage sites are conserved in mouse factor VIII. The tyrosine residue for von Willebrand factor binding is also conserved.

According to Elder et al., the nucleotide sequence (SEQ ID NO:5) of mouse factor VIII contains 7519 bases and has 67% identity overall with the human nucleotide sequence (SEQ ID NO:1). The 6957 base pairs of murine coding sequence have 82% sequence identity with the 7053 base pairs of coding sequence in human factor VIII. When the B domain is not included in the comparison, there is an 88% nucleotide sequence identity.

Elder et al. report that human and mouse factor VIII molecules are 74% identical overall, and that 95% of the human residues that lead to hemophilia when altered are identical in the mouse. These data support the application of the same techniques used to identify amino acid sequence with coagulant activity and/or immunoreactivity to antibodies in the porcine factor VIII molecule to the mouse or other animal factor VIII to identify similar amino acid sequences and prepare hybrid molecules.

Preparation of Hybrid Factor VIII Molecules Having Reduced Cross-reactivity Using Human and Non-human, Non-porcine Mammalian Factor VIII Amino Acid Sequence and Non-factor VIII Amino Acid Sequence:

Porcine factor VIII is used clinically to treat factor VIII deficiency patients who have inhibitory antibodies to human factor VIII. Cross-reactivity, in which human plasma reacts with porcine factor VIII, can be reduced by preparation of hybrid porcine/non-human, non-porcine mammalian or hybrid equivalent factor VIII. In a preferred embodiment, a determination of whether human A2, C2, or other domain-specific inhibitors react with non-human, non-porcine mammalian ("other mammalian") factor VIII is made, using the routine Bethesda assay and the particular other mammalian plasma as the standard. Inhibitor titers are usually measured in plasma, so purified other mammalian factor VIII is not necessary. If the inhibitors do not react with the other mammalian factor VIII, such as murine factor VIII, the sequence of which is known, then corresponding other mammalian sequence can be substituted into the porcine epitope region, as identified by using human/porcine hybrids. Once the animal sequence is known, site directed mutagenesis techniques, such as oligonucleotide-mediated mutagenesis described by Kunkel, T. A. et al. (1991) *Meth. Enzymol* 204: 125–139, can be used to prepare the hybrid porcine/animal factor VIII molecule. If other animal plasmas are less reactive with A2, C2, or other factor VIII inhibitors than murine or porcine factor VIII, the animal sequence corresponding to the porcine epitope can be determined by routine procedures, such as RT-PCR, and a hybrid human/animal or porcine/animal factor VIII constructed by site-directed mutagenesis. Also, hybrid human/animal or porcine/non-porcine mammalian factor VIII having reduced cross-reactivity with human plasma compared to porcine factor VIII can be prepared that has corresponding amino acid sequence substitution from one or more other animals. In a further embodiment, cross-reactivity can be reduced by substitution of amino acid sequence having no known identity to factor VIII amino acid sequence, preferably alanine residues using alanine scanning mutagenesis techniques, for porcine epitope sequence.

After identification of clinically significant epitopes, recombinant hybrid factor VIII molecules will be expressed that have less than or equal cross-reactivity compared with porcine factor VIII when tested in vitro against a broad survey of inhibitor plasmas. Preferably these molecules will be combined A2/C2 hybrids in which immunoreactive amino acid sequence in these domains is replaced by other mammalian sequence. Additional mutagenesis in these regions may be done to reduce cross-reactivity. Reduced cross-reactivity, although desirable, is not necessary to produce a product that may have advantages over the existing porcine factor VIII concentrate, which produces side effects due to contaminant porcine proteins and may produce untoward effects due to the immunogenicity of porcine factor VIII sequences. A hybrid human/other mammalian or porcine/other mammalian factor VIII molecule will not contain foreign porcine proteins. Additionally, the extensive epitope mapping accomplished in the porcine A2 domain indicates that greater than 95% of the therapeutic hybrid human/porcine factor VIII sequence will be human.

Preparation of Hybrid Factor VIII Equivalents:

The methods for amino acid substitution in factor VIII molecules described above and in the examples can also be used to prepare procoagulant recombinant hybrid factor VIII equivalent molecules or fragments thereof comprising at least one amino acid sequence including one or more amino acids having no known amino acid sequence identity to factor VIII ("non-factor VIII sequence") substituted for at least one specific amino acid sequence that includes an antigenic and/or immunogenic site in human, animal, or hybrid factor VIII. The resulting active hybrid factor VIII equivalent molecule has equal or less reactivity with factor VIII inhibitory antibodies and/or less immunogenicity in human and animals than the unsubstituted human, animal, or hybrid factor VIII.

Suitable amino acid residues that can be substituted for those sequences of amino acids critical to coagulant and/or antigenic and/or immunogenic activity in human or animal factor VIII or hybrid human/animal factor VIII to prepare a hybrid equivalent factor VIII molecule include any amino acids having no known sequence identity to animal or human factor VIII amino acid sequence that has coagulant, antigenic, or immunogenic activity. In a preferred embodiment, the amino acids that can be substituted include alanine residues using alanine scanning mutagenesis techniques.

Hybrid factor VIII equivalent molecules described herein also include those molecules in which amino acid residues having no known identity to animal factor VIII sequence are substituted for amino acid residues not critical to coagulant, antigenic, or immunogenic activity.

As described above, in one embodiment of a hybrid factor VIII equivalent molecule, the molecule has reduced cross-reactivity with inhibitor plasmas. One or more epitopes in the cross-reactive factor VIII are identified, as described above, and then replaced by non-factor VIII amino acid sequence, preferably alanine residues, using, for example, the alanine scanning mutagenesis method.

In a preferred embodiment, a procoagulant recombinant hybrid factor VIII equivalent molecule is prepared comprising at least one sequence including one or more amino acids having no known sequence identity to factor VIII, preferably alanine residues, substituted for at least one sequence including one or more amino acids including an epitope, and/or for at least one sequence including one or more amino acids including an immunogenic site, preferably in human factor VIII. The resulting hybrid equivalent factor VIII molecule or fragment thereof has reduced or no immunoreactivity with inhibitory antibodies to factor VIII and/or reduced or no immunogenicity in human or animals. The methods for identifying specific antigenic amino acid sequence in the A2 domain of human factor VIII for substitution by nonantigenic porcine unique amino acid sequence are described in Examples 7 and 8 and are exemplary for identifying antigenic sequence in the A2 and other domains of human and animal factor VIII and for using site-directed mutagenesis methods such as alanine scanning mutagenesis to substitute non-factor VIII amino acid sequence.

Since the human A2 epitope has been narrowed to 25 or few amino acids, as described in Example 8, alanine scanning mutagenesis can be performed on a limited number of hybrid factor VIII constructs having human amino acid sequence to determine which are procoagulant, non-immunoreactive and/or nonimmunogenic hybrid factor VIII constructs based on A2 amino acid substitutions. In the A2 domain, the most likely candidates for alanine substitutions to achieve both reduced antigenicity and immunogenicity in the hybrid construct are Arg484, Pro485, Tyr487, Ser488, Arg489, Pro492, Val495, Phe501, and Ile508. The binding affinity of a hybrid construct comprising each of these mutants for mAb413 and a panel of A2 specific patient IgGs will be determined by ELISA. Any mutant that is active and has a binding affinity for A2 inhibitors that is reduced by more than 2 orders of magnitude is a candidate for the A2 substituted factor VIII molecule. Constructs having more than one mutation will be selected, based on the assumption that the more the epitope is altered, the less immunogenic it will be. It is possible that there are other candidate residues in the region between Arg484-Ile508, since there may be key residues for the epitope that are common to both human and porcine factor VIII. For example, charged residues are frequently involved in protein-protein interactions and, in fact, an alanine substitute for Arg490 produces a factor VIII procoagulated having only 0.2% of the reactivity to inhibitor of human factor VIII (Table VI). Similarly, an alanine substitution for Lys493 is a possible candidate.

This procedure will be carried out in the C2 epitope and the putative third epitope, which is thought to be in the A3 or C1 domains, as well as any other epitopes identified in factor VIII, to prepare hybrid equivalent factor VIII constructs.

Diagnostic Assays.

The hybrid human/animal, animal/animal, or equivalent factor VIII cDNA and/or protein expressed therefrom, in whole or in part, can be used in assays as diagnostic reagents for the detection of inhibitory antibodies to human or animal factor VIII or to hybrid human/animal factor or equivalent VIII in substrates, including, for example, samples of serum and body fluids of human patients with factor VIII deficiency. These antibody assays include assays such as ELISA assays, immunoblots, radioimmunoassays, immunodiffusion assays, and assay of factor VIII biological activity (e.g., by coagulation assay). Techniques for preparing these reagents and methods for use thereof are known to those skilled in the art. For example, an immunoassay for detection of inhibitory antibodies in a patient serum sample can include reacting the test sample with a sufficient amount of the hybrid human/animal factor VIII that contains at least one antigenic site, wherein the amount is sufficient to form a detectable complex with the inhibitory antibodies in the sample.

Nucleic acid and amino acid probes can be prepared based on the sequence of the hybrid human/porcine, human/non-human, non-porcine mammalian, animal/animal, or equivalent factor VIII cDNA or protein molecule or fragments thereof. In some embodiments, these can be labeled using dyes or enzymatic, fluorescent, chemiluminescent, or radioactive labels that are commercially available. The amino acid probes can be used, for example, to screen sera or other body fluids where the presence of inhibitors to human, animal, or hybrid human/animal factor VIII is suspected. Levels of inhibitors can be quantitated in patients and compared to healthy controls, and can be used, for example, to determine whether a patient with a factor VIII deficiency can be treated with a hybrid human/animal or hybrid equivalent factor VIII. The cDNA probes can be used, for example, for research purposes in screening DNA libraries.

Pharmaceutical Compositions.

Pharmaceutical compositions containing hybrid human/animal, porcine/non-human, non-porcine mammalian, animal-1/animal-2, or equivalent factor VIII, alone or in combination with appropriate pharmaceutical stabilization compounds, delivery vehicles, and/or carrier vehicles, are prepared according to known methods, as described in Remington's *Pharmaceutical Sciences* by E. W. Martin.

In one preferred embodiment, the preferred carriers or delivery vehicles for intravenous infusion are physiological saline or phosphate buffered saline.

In another preferred embodiment, suitable stabilization compounds, delivery vehicles, and carrier vehicles include but are not limited to other human or animal proteins such as albumin.

Phospholipid vesicles or liposomal suspensions are also preferred as pharmaceutically acceptable carriers or delivery vehicles. These can be prepared according to methods known to those skilled in the art and can contain, for example, phosphatidylserine/-phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the hybrid factor VIII is then introduced into the container. The container is then swirled by hand to free lipid material from the sides of the container and to disperse lipid aggregates, thereby forming the liposomal suspension.

The hybrid factor or hybrid equivalent factor VIII can be combined with other suitable stabilization compounds, delivery vehicles, and/or carrier vehicles, including vitamin K dependent clotting factors, tissue factor, and von Willebrand factor (vWf) or a fragment of vWf that contains the factor VIII binding site, and polysaccharides such as sucrose.

Hybrid or hybrid equivalent factor VIII can also be delivered by gene therapy in the same way that human factor VIII can be delivered, using delivery means such as retroviral vectors. This method consists of incorporation of factor VIII cDNA into human cells that are transplanted directly into a factor VIII deficient patient or that are placed in an implantable device, permeable to the factor VIII molecules but impermeable to cells, that is then transplanted. The preferred method will be retroviral-mediated gene transfer. In this method, an exogenous gene (e.g., a factor VIII cDNA) is cloned into the genome of a modified retrovirus. The gene is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature [e.g., Kohn, D. B. et al. (1989) *Transufusion* 29:812–820].

Hybrid factor VIII can be stored bound to vWf to increase the half-life and shelf-life of the hybrid molecule.

Additionally, lyophilization of factor VIII can improve the yields of active molecules in the presence of vWf. Current methods for storage of human and animal factor VIII used by commercial suppliers can be employed for storage of hybrid factor VIII. These methods include: (1) lyophilization of factor VIII in a partially-purified state (as a factor VIII "concentrate" that is infused without further purification); (2) immunoaffinity-purification of factor VIII by the Zimmerman method and lyophilization in the presence of albumin, which stabilizes the factor VIII; (3) lyophilization of recombinant factor VIII in the presence of albumin.

Additionally, hybrid factor VIII has been indefinitely stable at 4° C. in 0.6 M NaCl, 20 mM MES, and 5 mM $CaCl_2$ at pH 6.0 and also can be stored frozen in these buffers and thawed with minimal loss of activity.

Methods of Treatment.

Hybrid or hybrid equivalent factor VIII is used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials are preferably administered intravenously.

Additionally, hybrid or hybrid equivalent factor VIII can be administered by transplant of cells genetically engineered to produce the hybrid or by implantation of a device containing such cells, as described above.

In a preferred embodiment, pharmaceutical compositions of hybrid or hybrid equivalent factor VIII alone or in combination with stabilizers, delivery vehicles, and/or carriers are infused into patients intravenously according to the same procedure that is used for infusion of human or animal factor VIII.

The treatment dosages of hybrid or hybrid equivalent factor VIII composition that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the hybrid factor VIII is included in the pharmaceutically acceptable carrier, delivery vehicle, or stabilizer in an amount sufficient to deliver to a patient a therapeutically effective amount of the hybrid to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher, J. M. et al. 328 *New Engl. J. Med.* 328:453–459; Pittman, D. D. et al. (1992) *Blood* 79:389–397; and Brinkhous et al. (1985) *Proc. Natl. Acad. Sci.* 82:8752–8755.

Usually, the desired plasma factor VIII level to be achieved in the patient through administration of the hybrid or hybrid equivalent factor VIII is in the range of 30–100% of normal. In a preferred mode of administration of the hybrid or hybrid equivalent factor VIII, the composition is given intravenously at a preferred dosage in the range from about 5 to 50 units/kg body weight, more preferably in a range of 10–50 units/kg body weight, and most preferably at a dosage of 20–40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453–1474, 1460, in *Hematology*, Williams, W. J., et al., ed. (1990). Patients with inhibitors may require more hybrid or hybrid equivalent factor VIII, or patients may require less hybrid or hybrid equivalent factor VIII because of its higher specific activity than human factor VIII or decreased antibody reactivity or immunogenicity. As in treatment with human or porcine factor VIII, the amount of hybrid or hybrid equivalent factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Treatment can take the form of a single intravenous administration of the composition or periodic or continuous administration over an extended period of time, as required. Alternatively, hybrid or hybrid equivalent factor VIII can be administered subcutaneously or orally with liposomes in one or several doses at varying intervals of time.

Hybrid or hybrid equivalent factor VIII can also be used to treat uncontrolled bleeding due to factor VIII deficiency in hemophiliacs who have developed antibodies to human factor VIII. In this case, coagulant activity that is superior to that of human or animal factor VIII alone is not necessary. Coagulant activity that is inferior to that of human factor VIII (i.e., less than 3,000 units/mg) will be useful if that activity is not neutralized by antibodies in the patient's plasma.

It has been demonstrated herein that hybrid factor VIII's and modified factor VIII's can differ in specific activity from human factor VIII. Hybrid, hybrid equivalent and modified factor VIII proteins having greater procoagulant activity from human factor VIII are useful in treatment of hemophilia because lower dosages will be required to correct a patient's factor VIII deficiency. Hybrid, hybrid equivalent and modified factor VIII's having lower procoagulant activity than human factor VIII are also suitable for therapeutic use provided they have at least 1% of specific activity compared to normal human factor VIII. A hybrid, hybrid equivalent or modified factor VIII of the present invention having procoagulant activity is therefore defined as having at least 1% of the specific activity of human factor VIII.

The hybrid or hybrid equivalent factor VIII molecule and the methods for isolation, characterization, making, and using it generally described above will be further understood with reference to the following non-limiting examples.

EXAMPLE 1

Assay of Porcine Factor VIII and Hybrid Human/porcine Factor VIII

Porcine factor VIII has more coagulant activity than human factor VIII, based on specific activity of the molecule. These results are shown in Table III in Example 4.

This conclusion is based on the use of appropriate standard curves that allow human porcine factor VIII to be fairly compared. Coagulation assays are based on the ability of factor VIII to shorten the clotting time of plasma derived from a patient with hemophilia A. Two types of assays were employed: the one-stage and the two stage assay.

In the one-stage assay, 0.1 ml hemophilia A plasma (George King Biomedical, Inc.) was incubated with 0.1 ml activated partial thromboplastin reagent (APTT) (Organon Teknika) and 0.01 ml sample or standard, consisting of diluted, citrated normal human plasma, for 5 min at 37° C. in a water bath. Incubation was followed by addition of 0.1 ml 20 mM $CaCl_2$, and the time for development of a fibrin clot was determined by visual inspection.

A unit of factor VIII is defined as the amount present in 1 ml of citrated normal human plasma. With human plasma as the standard, porcine and human factor VIII activity were compared directly. Dilutions of the plasma standard or purified proteins were made into 0.15 M NaCl, 0.02 M HEPES, pH 7.4. The standard curve was constructed based on 3 or 4 dilutions of plasma, the highest dilution being $\frac{1}{50}$, and on $\log_{10}$ clotting time plotted against $\log_{10}$ plasma concentration, which results in a linear plot. The units of factor VIII in an unknown sample were determined by interpolation from the standard curve.

The one-stage assay relies on endogenous activation of factor VIII by activators formed in the hemophilia A plasma, whereas the two-stage assay measures the procoagulant activity of preactivated factor VIII. In the two-stage assay, samples containing factor VIII that had been reacted with thrombin were added to a mixture of activated partial thromboplastin and human hemophilia A plasma that had been preincubated for 5 min at 37° C. The resulting clotting times were then converted to units/ml, based on the same human standard curve described above. The relative activity in the two-stage assay was higher than in the one-stage assay because the factor VIII had been preactivated.

EXAMPLE 2

Characterization of the Functional Difference Between Human and Porcine Factor VIII The isolation of porcine and human plasma-derived factor VIII and human recombinant factor VIII have been described in the literature in Fulcher, C. A. et al. (1982) *Proc. Natl. Acad. Sci. USA* 79:1648–1652; Toole et al. (1984) *Nature* 312:342–347 (Genetics Institute); Gitschier et al. (1984) *Nature* 312:326–330 (Genentech); Wood et al. (1984) *Nature* 312:330–337 (Genentech); Vehar et al. 312 *Nature* 312:337–342 (Genentech); Fass et al. (1982) *Blood* 59:594; Toole et al. (1986) *Proc. Natl. Acad. Sci. USA* 83:5939–5942. This can be accomplished in several ways. All these preparations are similar in subunit composition, although there is a functional difference in stability between human and porcine factor VIII.

For comparison of human recombinant and porcine factor VIII, preparations of highly-purified human recombinant factor VIII (Cutter Laboratories, Berkeley, Calif.) and porcine factor VIII [immunopurified as described in Fass et al. (1982) *Blood* 59:594] were subjected to high-pressure liquid chromatography (HPLC) over a MONO Q™ (Pharmacia-LKB, Piscataway, N.J.) anion-exchange column (Pharmacia, Inc.). The purposes of the MONO Q™ HPLC step were elimination of minor impurities of exchange of human and porcine factor VIII into a common buffer for comparative purposes. Vials containing 1000–2000 units of factor VIII were reconstituted with 5 ml $H_2O$. Hepes (2 M at pH 7.4) was then added to a final concentration of 0.02 M. Factor VIII was applied to a MONO Q™ HR 5/5 column equilibrated in 0.15 M NaCl, 0.02 M Hepes, 5 mM $CaCl_2$, at pH 7.4 (Buffer A plus 0.15 M NaCl); washed with 10 ml Buffer A+0.15 M NaCl; and eluted with a 20 ml linear gradient, 0.15 M to 0.90 M NaCl in Buffer A at a flow rate of 1 ml/min.

For comparison of human plasma-derived factor VIII (purified by MONO Q™ HPLC) and porcine factor VIII, immunoaffinity-purified, plasma-derived porcine factor VIII was diluted 1:4 with 0.04 M Hepes, 5 mM $CaCl_2$, 0.01% Tween-80, at pH 7.4, and subjected to MONO Q™ HPLC under the same conditions described in the previous paragraph for human factor VIII. These procedures for the isolation of human and porcine factor VIII are standard for those skilled in the art.

Column fractions were assayed for factor VIII activity by a one-stage coagulation assay. The average results of the assays, expressed in units of activity per $A_{280}$ of material, are given in Table II, and indicate that porcine factor VIII has at least six times greater activity than human factor VIII when the one-stage assay is used.

TABLE II

COMPARISON OF HUMAN AND PORCINE FACTOR VIII COAGULANT ACTIVITY

|  | Activity (U/$A_{280}$) |
|---|---|
| Porcine | 21,300 |
| Human plasma-derived | 3,600 |
| Human recombinant | 2,400 |

EXAMPLE 3

Comparison of the Stability of Human and Porcine Factor VIII

The results of the one-stage assay for factor VIII reflect activation of factor VIII to factor VIIIa in the sample and possibly loss of formed factor VIIIa activity. A direct comparison of the stability of human and porcine factor VIII was made. Samples from MONO Q™ HPLC (Pharmacia, Inc., Piscataway, N.J.) were diluted to the same concentration and buffer composition and reacted with thrombin. At various times, samples were removed for two-stage coagulation assay. Typically, peak activity (at 2 min) was 10-fold greater for porcine than human factor VIIIa, and the activities of both porcine and human factor VIIIa subsequently decreased, with human factor VIIIa activity decreasing more rapidly.

Generally, attempts to isolate stable human factor VIIIa are not successful even when conditions that produce stable porcine factor VIIIa are used. To demonstrate this, MONO Q™-HPLC-purified human factor VIII was activated with thrombin and subjected to cation-exchange (Pharmacia, Inc.) HPLC under conditions that produce stable porcine factor VIIIa, as described by Lollar et al. (1989) *Biochemistry* 28:666.

Human factor VIII, 43 μg/ml (0.2 μM) in 0.2 M NaCl, 0.01 M Hepes, 2.5 mM $CaCl_2$, at pH 7.4, in 10 ml total volume, was reacted with thrombin (0.036 μM) for 10 min, at which time FPR-$CH_2$Cl D-phenyl-prolyl-arginyl-chloromethyl ketone was added to a concentration of 0.2 μM for irreversible inactivation of thrombin. The mixture then was diluted 1:1 with 40 mM 2-(N-morpholino) ethane sulfonic acid (MES), 5 mM CaCl$_2$, at pH 6.0, and loaded at 2 ml/min onto a MONO S™ HR 5/5 HPLC column (Pharmacia, Inc.) equilibrated in 5 mM MES, 5 mM CaCl$_2$, at pH 6.0 (Buffer B) plus 0.1 M NaCl. Factor VIIIa was eluted without column washing with a 20 ml gradient from 0.1 M NaCl to 0.9 M NaCl in Buffer B at 1 ml/min.

The fraction with coagulant activity in the two-stage assay eluted as a single peak under these conditions. The specific activity of the peak fraction was approximately 7,500 U/A$_{280}$. Sodium dodecyl sulfate-polyacrylamide gel electrophoresis (SDS-PAGE) of the MONO S™ factor VIIIa peak, followed by silver staining of the protein, revealed two bands corresponding to a heterodimeric (A3-C1-C2/A1) derivative of factor VIII. Although the A2 fragment was not identified by silver staining under these conditions because of its low concentration, it was identified as a trace constituent by $^{125}$I-labeling.

In contrast to the results with human factor VIII, porcine factor VIIIa isolated by MONO S™ HPLC under the same conditions had a specific activity $1.6\times10^6$ U/A$_{280}$. Analysis of porcine factor VIIIa by SDS-PAGE revealed 3 fragments corresponding to A1, A2, and A3-C1-C2 subunits, demonstrating that porcine factor VIIIa possesses three subunits.

The results of MONO S™ HPLC of human thrombin-activated factor VIII preparations at pH 6.0 indicate that human factor VIIIa is labile under conditions that yield stable porcine factor VIIIa. However, although trace amounts of A2 fragment were identified in the peak fraction, determination of whether the coagulant activity resulted from small amounts of heterotrimeric factor VIIIa or from heterodimeric factor VIIIa that has a low specific activity was not possible from this method alone.

A way to isolate human factor VIIIa before it loses its A2 subunit is desirable to resolve this question. To this end, isolation was accomplished in a procedure that involves reduction of the pH of the MONO S™ buffers to pH 5. MONO Q™-purified human factor VIII (0.5 mg) was diluted with H$_2$O to give a final composition of 0.25 mg/ml (1 μm) factor VIII in 0.25 M NaCl, 0.01 M Hepes, 2.5 mM CaCl$_2$, 0.005% Tween-80, at pH 7.4 (total volume 7.0 ml). Thrombin was added to a final concentration of 0.072 μm and allowed to react for 3 min. Thrombin was then inactivated with FPR—CH$_2$Cl (0.2 μm). The mixture then was diluted 1:1 with 40 mM sodium acetate, 5 mM CaCl$_2$, 0.01% Tween-80, at pH 5.0, and loaded at 2 ml/min onto a MONO S™ HR 5/5 HPLC column equilibrated in 0.01 M sodium acetate, 5 mM CaCl$_2$, 0.01% Tween-80, at pH 5.0, plus 0.1 M NaCl. Factor VIIIa was eluted without column washing with a 20 ml gradient from 0.1 M NaCl to 1.0 M NaCl in the same buffer at 1 ml/min. This resulted in recovery of coagulant activity in a peak that contained detectable amounts of the A2 fragment as shown by SDS-PAGE and silver staining. The specific activity of the peak fraction was tenfold greater than that recovered at pH 6.0 (75,000 U/A$_{280}$ v. 7,500 U/A$_{280}$). However, in contrast to porcine factor Villa isolated at pH 6.0, which is indefinitely stable at 4° C., human factor VIIIa activity decreased steadily over a period of several hours after elution from MONO S™. Additionally, the specific activity of factor VIIIa purified at pH 5.0 and assayed immediately is only 5% that of porcine factor VIIIa, indicating that substantial dissociation occurred prior to assay.

These results demonstrate that both human and porcine factor VIIIa are composed of three subunits (A1, A2, and A3-C1-C2). Dissociation of the A2 subunit is responsible for the loss of activity of both human and porcine factor VIIIa under certain conditions, such as physiological ionic strength, pH, and concentration. The relative stability of porcine factor VIIIa under certain conditions is because of stronger association of the A2 subunit.

EXAMPLE 4

Preparation of Hybrid Human/porcine Factor VIII by Reconstitution with Subunits

Porcine factor VIII light chains and factor VIII heavy chains were isolated as follows. A 0.5 M solution of EDTA at pH 7.4 was added to MONO Q™-purified porcine factor VIII to a final concentration of 0.05 M and was allowed to stand at room temperature for 18–24 h. An equal volume of 10 mM histidine-Cl, 10 mM EDTA, 0.2% v/v Tween 80, at pH 6.0 (Buffer B), was added, and the solution was applied at 1 ml/min to a MONO S™ HR 5/5 column previously equilibrated in Buffer A plus 0.25 M NaCl. Factor VIII heavy chains did not bind the resin, as judged by SDS-PAGE. Factor VIII light chain was eluted with a linear, 20 ml, 0.1–0.7 M NaCl gradient in Buffer A at 1 ml/min and was homogeneous by SDS-PAGE. Factor VIII heavy chains were isolated by MONO Q™ HPLC (Pharmacia, Inc., Piscataway, N.J.) in the following way. Factor VIII heavy chains do not adsorb to MONO S™ during the purification of factor VIII light chains. The fall-through material that contained factor VIII heavy chains was adjusted to pH 7.2 by addition of 0.5 M Hepes buffer, pH 7.4, and applied to a MONO Q™-HR5/5 HPLC column (Pharmacia, Inc.) equilibrated in 0.1 M NaCl, 0.02 M Hepes, 0.01% Tween-80, pH 7.4. The column was washed with 10 ml of this buffer, and factor VIII heavy chains were eluted with a 20 ml 0.1–1.0 M NaCl gradient in this buffer. Human light chains and heavy chains were isolated in the same manner.

Human and porcine light and heavy chains were reconstituted according to the following steps. Ten μl human or porcine factor VIII light chain, 100 μg/ml, was mixed in 1 M NaCl, 0.02 M Hepes, 5 mM CaCl$_2$, 0.01% Tween-80, pH 7.4, with (1) 25 μl heterologous heavy chain, 60 μg/ml, in the same buffer; (2) 10 μl 0.02 M Hepes, 0.01% Tween-80, pH 7.4; (3) 5 μl 0.6 M CaCl$_2$, for 14 hr at room temperature. The mixture was diluted ¼ with 0.02 M MES, 0.01% Tween-80, 5 mM CaCl$_2$, pH 6 and applied to MONO S™ Hr5/5 equilibrated in 0.1 M NaCl, 0.02 M MES, 0.01% Tween-80, 5 mM CaCl$_2$, pH 6.0. A 20 ml gradient was run from 0.1–1.0 M NaCl in the same buffer at 1 ml/min, and 0.5 ml fractions were collected. Absorbance was read at 280 nm of fractions, and fractions were assayed with absorbance for factor VIII activity by the one-stage clotting assay. Heavy chains were present in excess, because free light chain (not associated with heavy chain) also binds MONO S™; excess heavy chains ensure that free light chains are not part of the preparation. Reconstitution experiments followed by MONO S™ HPLC purification were performed with all four possible combinations of chains: human light chain/human heavy chain, human light chain/porcine heavy chain, porcine light chain/porcine heavy chain, porocine light chain/human heavy chain. Table III shows that human light chain/porcine heavy chain factor VIII has activity comparable to native porcine factor VIII (Table II), indicating that structural elements in the porcine heavy chain are responsible for the increased coagulant activity of porcine factor VIII compared to human factor VIII.

TABLE III

COMPARISON OF HYBRID HUMAN/PORCINE FACTOR VIII COAGULANT ACTIVITY WITH HUMAN AND PORCINE FACTOR VIII

| | Activity (U/A$_{280}$) |
|---|---|
| Porcine light chain/porcine heavy chain | 30,600 |
| Human light chain/porcine heavy chain | 44,100 |
| Porcine light chain/human heavy chain | 1,100 |
| Human light chain/human heavy chain | 1,000 |

The porcine A1/A3-C1-C2 dimer, the porcine A2 domain, the human A1/A3-C1-C2 dimer, and the human A2 domain were each isolated from porcine or human blood, according to the method described in Lollar et al. (1992) *J. Biol. Chem.* 267(33):23652–23657. For example, to isolate the porcine A1/A3-C1-C2 dimer, porcine factor VIIIa (140 μg) at pH 6.0 was raised to pH 8.0 by addition of 5 N NaOH for 30 minutes, producing dissociation of the A2 domain and 95% inactivation by clotting assay. The mixture was diluted 1:8 with buffer B (20 mM HEPES, 5 mM CaCl$_2$, 0.01% Tween-80, pH 7.4) and applied to a MONOS™ column equilibrated in buffer B. The A1/A3-C1-C2 dimer eluted as a single sharp peak at approximately 0.4 M NaCl by using a 0.1–1.0 M NaCl gradient in buffer B. To isolate the porcine A2 domain, porcine factor VIIIa was made according to the method of Lollar et al. (1989) *Biochem* 28:666–674, starting with 0.64 mg of factor VIII. Free porcine A2 domain was isolated as a minor component (50 μg) at 0.3 M NaCl in the MONOS™ chromatogram.

Hybrid human/porcine factor VIII molecules were reconstituted from the dimers and domains as follows. The concentrations and buffer conditions for the purified components were as follows: porcine A2, 0.63 μM in buffer A (5 mM MES; 5 mM CaCl$_2$, 0.01% Tween 80, pH 6.0) plus 0.3 M NaCl; porcine A1/A3-C1-C2, 0.27 μM in buffer B plus 0.4 M NaCl, pH 7.4; human A2, 1 μM in 0.3 M NaCl, 10 mM histidine-HCl, 5 mM CaCl$_2$, 0.01% Tween 20, pH 6.0; human A1/A3-C1-C2, 0.18 μM in 0.5 M NaCl, 10 mM histidine-Cl, 2.5 mM CaCl$_2$, 0.1% Tween-20, pH 6.0. Reconstitution experiments were done by mixing equal volumes of A2 domain and A1/A3-C1-C2 dimer. In mixing experiments with porcine A1/A3-C1-C2 dimer, the pH was lowered to 6.0 by addition of 0.5 M MES, pH 6.0, to 70 mM.

The coagulation activities of all four possible hybrid factor VIIIa molecules—[pA2/(hA1/A3-C1-C2)], [hA2/(pA1/A3-C1-C2)], [pA2/(pA1/pA3-C1-C2)], and [hA2/(hA1/A3-C1-C2)]—were obtained by a two-stage clotting assay at various times.

The generation of activity following mixing the A2 domains and A1/A3-C1-C2 dimers was nearly complete by one hour and was stable for at least 24 hours at 37° C. Table IV shows the activity of reconstituted hybrid factor VIIIa molecules when assayed at 1 hour. The two-stage assay, by which the specific activities of factor VIIIa molecules were obtained, differs from the one-stage assay, and the values cannot be compared to activity values of factor VIII molecules obtained by a one-stage assay.

TABLE IV

COMPARISON OF COAGULANT ACTIVITIES OF DOMAIN-SUBSTITUTED HYBRID HUMAN/PORCINE FACTOR VIIIa

| Hybrid fVIIIa | Specific Activity (U/mg) |
|---|---|
| Porcine A2 + Human A1/A3-C1-C2 | 140,000 |
| Porcine A2 + Porcine A1/A3-C1-C2 | 70,000 |
| Human A2 + Porcine A1/A3-C1-C2 | 40,000 |
| Human A2 + Human A1/A3-C1-C2 | 40,000 |

Table IV shows that the greatest activity was exhibited by the porcine A2 domain/human A1/A3-C1-C2 dimer, followed by the porcine A2 domain/porcine A1/A3-C1-C2 dimer. Thus, when the A2 domain of porcine factor VIIIa was mixed with the A1/A3-C1-C2 dimer of human factor VIIIa, coagulant activity was obtained. Further, when the A2 domain of human factor VIIIa was mixed with the A1/A3-C1-C2 dimer of porcine factor VIIIa, coagulant activity was obtained. By themselves, the A2, A1, and A3-C1-C2 regions have no coagulant activity.

EXAMPLE 6

Isolation and Sequencing of the A2 Domain of Porcine Factor VIII

Only the nucleotide sequence encoding the B domain and part of the A2 domain of porcine factor VIII has been sequenced previously [Toole et al. (1986) *Proc. Natl. Acad. Sci. USA* 83:5939–5942]. The cDNA and predicted amino acid sequences (SEQ ID NOs: 3 and 4, respectively) for the entire porcine factor VIII A2 domain are disclosed herein.

The porcine factor VIII A2 domain was cloned by reverse transcription of porcine spleen total RNA and PCR amplification; degenerate primers based on the known human factor VIII cDNA sequence and an exact porcine primer based on a part of the porcine factor VIII sequence were used. A 1 kb PCR product was isolated and amplified by insertion into a BLUESCRIPT™ (Stratagene, La Jolla, Calif.) phagemid vector.

The porcine A2 domain was completely sequenced by dideoxy sequencing. The cDNA and predicted amino acid sequences are as described in SEQ ID NOs: 3 and 4, respectively.

EXAMPLE 7

Preparation of Recombinant Hybrid Human/animal Factor VIII

The nucleotide and predicted amino acid sequences (SEQ ID NOs: 1 and 2, respectively) of human factor VIII have been described in the literature [Toole et al. (1984) *Nature* 312:342–347 (Genetics Institute); Gitschier et al. *Nature* 312:326–330 (Genentech); Wood, et al. (1984) *Nature* 312:330–337 (Genentech); Vehar et al. *Nature* 312:337–342 (Genentech)].

Making recombinant hybrid human/animal factor VIII requires that a region of human factor VIII cDNA (Biogen Corp.) be removed and the animal cDNA sequence having sequence identity be inserted. Subsequently, the hybrid cDNA is expressed in an appropriate expression system. As an example, hybrid factor VIII cDNAs were cloned in which some or all of the porcine A2 domain was substituted for the corresponding human A2 sequences. Initially, the entire cDNA sequence corresponding to the A2 domain of human factor VIII and then a smaller part of the A2 domain was looped out by oligonucleotide-mediated mutagenesis, a method commonly known to those skilled in the art (see, e.g., Sambrook, J., E. F. Fritsch, and T. Maniatis, *Molecular Cloning: A Laboratory Manual*, Chapter 15, Cold Spring Harbor Press, Cold Spring Harbor, 1989). The steps were as follows.

Materials.

Methoxycarbonyl-D-cyclohexylglycyl-glycyl-arginine-p-nitroanilide (SPECTROZYME™, Xa) and anti-factor VIII monoclonal antibodies ESH4 and ESH8 were purchased from American Diagnostica (Greenwich, Conn.). Unilamellar phosphatidylcholine/phosphatidylserine (75/25, w/w) vesicles were prepared according to the method of Barenholtz, Y., et al., 16 *Biochemistry* 2806–2810 (1977)). Recombinant desulfatohirudin was obtained from Dr. R. B. Wallis, Ciba-Geigy Pharmaceuticals (Cerritos, Calif.). Porcine factors IXa, X, Xa, and thrombin were isolated according to the methods of Lollar et al. (1984) *Blood* 63:1303–1306, and Duffy, E. J. et al. (1992) *J. Biol. Chem.* 207:7621–7827. Albumin-free pure recombinant human factor VIII was obtained from Baxter-Biotech (Deerfield, Ill.).

Cloning of the Porcine Factor VIII A2 Domain.

The cDNA encoding the porcine A2 domain was obtained following PCR of reverse-transcribed porcine spleen mRNA isolated as described by Chomczyneki et al. (1987) *Anal. Biochem.* 162:156–159. cDNA was prepared using the first-strand cDNA synthesis kit with random hexamers as primers (Pharmacia, Piscataway, N.J.). PCR was carried out using a 5'-terminal degenerate primer 5' AARCAYC-CNAARACNTGGG 3' (SEQ ID NO:11), based on known limited porcine A2 amino acid sequence, and a 3'-terminal exact primer, 5' GCTCGCACTAGGGGGTCTTGAATTC 3' (SEQ ID NO:12), based on known porcine DNA sequence immediately 3' of the porcine A2 domain. These oligonucleotides correspond to nucleotides 1186–1203 and 2289–2313 in the human sequence (SEQ ID NO:1). Amplification was carried out for 35 cycles (1 minute 94□ C., 2 minutes 50° C., 2 minutes 72° C.) using Taq DNA polymerase (Promega Corp., Madison, Wis.). The 1.1-kilobase amplified fragment was cloned into pBluescript II KS-(Stratagene) at the EcoRV site using the T-vector procedure, as described by Murchuk, D. et al. (1991) *Nucl. Acids Res.* 19:1154. *Escherichia coli* XL1-Blue-competent cells were transformed, and plasmid DNA was isolated. Sequencing was carried out in both directions using SEQUENASE™ version 2.0 (U.S. Biochemical Corp., a Division of Amersham LifeScience, Inc., Arlington Hts, Ill.). This sequence was confirmed by an identical sequence that was obtained by direct sequencing of the PCR product from an independent reverse transcription of spleen RNA from the same pig (CIRCUMVENT™, New England Biolabs, Beverly, Mass.). The region containing the epitope for autoantibody RC was identified as 373–536 in human factor VIII (SEQ ID NO:2).

Construction and Expression of a Hybrid Human/Porcine Factor VIII cDNA.

B-domainless human factor VIII (HB⁻, from Biogen, Inc. Cambridge, Mass.), which lacks sequences encoding for amino acid residues 741–1648 (SEQ ID NO:2), was used as the starting material for construction of a hybrid human/porcine factor VIII. HB⁻ was cloned into the expression vector ReNeo. To facilitate manipulation, the cDNA for factor VIII was isolated as a XhoI/HpaI fragment from ReNeo and cloned into XhoI/EcoRV digested pBlueScript II KS. An oligonucleotide, 5' CCTTCCTTTATCCAAATACG-TAGATCAAGAGGAAATTGAC 3' (SEQ ID NO:7), was used in a site-directed mutagenesis reaction using uracil-containing phage DNA, as described by Kunkel, T. A. et al. (1991) *Meth. Enzymol* 204:125–139, to simultaneously loop-out the human A2 sequence (nucleotides 1169–2304 in SEQ ID NO: 1) and introduce a SnaBI restriction site. The A2-domainless human factor VIII containing plasmid was digested with SnaBI followed by addition of ClaI linkers. The porcine A2 domain was then amplified by PCR using the phosphorylated 5' primer 5' GTAGCGTTGCCAA-GAAGCACCCTAAGACG 3' (SEQ ID NO:8) and 3' primer 5' GAAGAGTAGTACGAGT-TATTTCTCTGGGTTCAATGAC 3' (SEQ ID NO:9), respectively. ClaI linkers were added to the PCR product followed by ligation into the human factor VIII-containing vector. The A1/A2 and A2/A3 junctions were corrected to restore the precise thrombin cleavage and flanking sequences by site-directed mutagenesis using the oligonucleotide shown in SEQ ID NO:8 and nucleotides 1–22 (5' GAA . . . TTC in SEQ ID NO:9) to correct the 5'- and 3'-terminal junctions, respectively. In the resulting construct, designated HP1, the human A2 domain was exactly substituted with the porcine A2 domain. A preliminary product contained an unwanted thymine at the A1-A2 junction as a result of the PCR amplification of the porcine A2 domain. This single base was looped out by use of the mutagenic oligonucleotide 5' CCTTTATCCAAATACG-TAGCGTTTGCCAAGAAG 3' (SEQ ID NO:10). The resulting hybrid nucleotide sequence encoded active factor VIII having human A1, porcine A2 and human A3, C1 and C2 domains.

A region containing 63% of the porcine NH₂-terminal A2 domain, which encompasses the putative A2 epitope, was substituted for the homologous human sequence of B-domainless cDNA by exchanging SpeI/BamHI fragments between the pBluescript plasmids containing human factor VIII and human/porcine A2 factor VIII cDNA. The sequence was confirmed by sequencing the A2 domain and splice sites. Finally, a SpeI/ApaI fragment, containing the entire A2 sequence, was substituted in place of the corresponding sequence in HB⁻, producing the HP2 construct.

Preliminary expression of HB⁻ and HP2 in COS-7 cells was tested after DEAE-dextran-mediated DNA transfection, as described by Seldon, R. F., in *Current Protocols in Molecular Biology* (Ausubel, F. M., et al., eds), pp. 9.21–9.26, Wiley Interscience, N.Y. After active factor VIII expression was confirmed and preliminary antibody inhibition studies were done, HB⁻ and HP2 DNA were then stably transfected into baby hamster kidney cells using liposome-mediated transfection (LIPOFECTIN™ Life Technologies, Inc., Gaithersburg, Md.). Plasmid-containing clones were selected for G418 resistance in Dulbecco's modified Eagle's medium-F12, 10% fetal calf serum (DMEM-F12/10% fetal calf serum) containing 400 μg/ml G418, followed by maintenance in DMEM-F12/10% fetal calf serum containing 100 μg/ml G418. Colonies showing maximum expression of HB⁻ and HP2 factor VIII activity were selected by ring cloning and expanded for further characterization.

HB⁻ and HP2 factor VIII expression was compared by plasma-free factor VIII assay, one-stage clotting assay, and enzyme-linked immunosorbent assay using purified recombinant human factor VIII as a standard. Specific coagulant activities of 2600 and 2580 units/mg were obtained for HB⁻ and HP2, respectively. HB⁻ and HP2 produced 1.2 and 1.4 units/ml/48 hours/10$^7$ cells, respectively. This is identical to that of the wild type construct (2,600±200 units/mg). The specific activities of HB$^-$ and HP2 were indistinguishable in the plasma-free factor VIII assay.

The biological activity of recombinant hybrid human/animal and equivalent factor VIII with A1, A2, A3, C1, and/or C2 domain substitutions can be evaluated initially by use of a COS-cell mammalian transient expression system. Hybrid human/animal and equivalent cDNA can be transfected into COS cells, and supernatants can be analyzed for factor VIII activity by use of one-stage and two-stage coagulation assays as described above. Additionally, factor VIII activity can be measured by use of a chromogenic substrate assay, which is more sensitive and allows analysis of larger numbers of samples. Similar assays are standard in the assay of factor VIII activity [Wood et al. (1984) *Nature* 312:330–337; Toole et al. (1984) *Nature* 312:342–347]. Expression of recombinant factor VIII in COS cells is also a standard procedure [Toole et al. (1984) *Nature* 312:342–347; Pittman et al. (1988) *Proc. Natl. Acad. Sci. USA* 85:2429–2433].

The human factor VIII cDNA used as starting materials for the recombinant molecules described herein has been expressed in COS cells yielding a product with biological activity. This material, as described above, can be used as a standard to compare hybrid human/animal factor VIII molecules. The activity in the assays is converted to a specific activity for proper comparison of the hybrid molecules. For this, a measurement of the mass of factor VIII produced by the cells is necessary and can be done by immunoassay with purified human and/or animal factor VIII as standards. Immunoassays for factor VIII are routine for those skilled in the art [See, e.g., Lollar et al. (1988) *Blood* 71:137–143].

EXAMPLE 8

Determination of Inhibitory Activity in Hybrid Human/Animal and Equivalent Factor VIII Sequences of human and animal factor VIII likely to be involved as epitopes (i.e., as recognition sites for inhibitory antibodies that react with factor VIII) can be determined using routine procedures, for example through use of assay with antibodies to factor VIII combined with site directed mutagenesis techniques such as splicing by overlap extension methods (SOE), as shown below. Sequences of animal factor VIII that are not antigenic compared to corresponding antigenic human sequences can be identified, and substitutions can be made to insert animal sequences and delete human sequences according to standard recombinant DNA methods. Sequences of amino acids such as alanine residues having no known sequence identity to factor VIII can also be substituted by standard recombinant DNA methods or by alanine scanning mutagenesis. Porcine factor VIII reacts less than human factor VIII with some inhibitory antibodies; this provides a basis for current therapy for patients with inhibitors. After the recombinant hybrids are made, they can be tested in vitro for reactivity with routine assays, including the Bethesda inhibitor assay. Those constructs that are less reactive than native human factor VIII and native animal factor VIII are candidates for replacement therapy.

The epitopes to which most, if not all, inhibitory antibodies reactive with human factor VIII are directed are thought to reside in two regions in the 2332 amino acid human factor VIII molecule, the A2 domain (amino acid residues 373–740) and the C2 domain (amino acid residues 2173–2332, both sequences shown in SEQ ID NO:2). The A2 epitope has been eliminated by making a recombinant hybrid human-porcine factor VIII molecule in which part of the human A2 domain is replaced by the porcine sequence having sequence identity to the replaced human amino acid sequence. This was accomplished, as described in example 7, by cloning the porcine A2 domain by standard molecular biology techniques and then cutting and splicing within the A2 domain using restriction sites. In the resulting construct, designated HP2, residues 373–604 (SEQ ID NO:4) of porcine factor VIII were substituted into the human A2 domain. HP2 was assayed for immunoreactivity with anti-human factor VIII antibodies using the following methods.

Factor VIII Enzyme-linked Immunosorbent Assay.

Microtiter plate wells were coated with 0.15 ml of 6 μg/ml ESH4, a human factor VIII light-chain antibody, and incubated overnight. After the plate was washed three times with $H_2O$, the wells were blocked for 1 hour with 0.15 M NaCl, 10 mM sodium phosphate, 0.05% Tween 20, 0.05% nonfat dry milk, 0.05% sodium azide, pH 7.4. To increase sensitivity, samples containing factor VIII were activated with 30 nM thrombin for 15 minutes. Recombinant desulfatohirudin then was added at 100 nM to inhibit thrombin. The plate was washed again and 0.1 ml of sample or pure recombinant human factor VIII (10–600 ng/ml), used as the standard, were added. Following a 2 hour incubation, the plate was washed and 0.1 ml of biotinylated ESH8, another factor VIII light-chain antibody, was added to each well. ESH8 was biotinylated using the Pierce sulfosuccinimidyl-6-(biotinamide)hexanoate biotinylation kit. After a 1 hour incubation, the plate was washed and 0.1 ml of strepavidin alkaline phosphatase was added to each well. The plate was developed using the Bio-Rad alkaline phosphatase substrate reagent kit, and the resulting absorbance at 405 nm for each well was determined by using a Vmax microtiter plate reader (Molecular Devices, Inc., Sunnyville, Calif.). Unknown factor VIII concentrations were determined from the linear portion of the factor VIII standard curve.

Factor VIII Assays.

$HB^-$ and HP2 factor VIII were measured in a one-stage clotting assay, which was performed as described above [Bowie, E. J. W., and C. A. Owen, in *Disorders of Hemostasis* (Ratnoff and Forbes, eds) pp. 43–72, Grunn & Stratton, Inc., Orlando, Fla. (1984)], or by a plasma-free assay as follows. $HB^-$ or HP2 factor VIII was activated by 40 nM thrombin in 0.15 M NaCl, 20 nM HEPES, 5 mM $CaCl_2$, 0.01% Tween 80, pH 7.4, in the presence of 10 nM factor IXa, 425 nM factor X, and 50 μM unilamellar phosphatidylserine/phosphatidylcholine (25/75, w/w) vesicles. After 5 minutes, the reaction was stopped with 0.05 M EDTA and 100 nM recombinant desulfatohirudin, and the resultant factor Xa was measured by chromogenic substrate assay, according to the method of Hill-Eubanks et al (1990) *J. Biol. Chem.* 265:17854–17858. Under these conditions, the amount of factor Xa formed was linearly proportional to the starting factor VIII concentration as judged by using purified recombinant human factor VIII (Baxter Biotech, Deerfield, Ill.) as the standard.

Prior to clotting assay, $HB^-$ or HP2 factor VIII were concentrated from 48 hour conditioned medium to 10–15 units/ml by HEPARIN-SEPHAROSE™ chromatography (Pharmacia, Inc., Piscataway, N.J.). $HB^-$ or HP2 factor VIII were added to hemophilia A plasma (George King Biomedical) to a final concentration of 1 unit/ml. Inhibitor titers in RC or MR plasma or a stock solution of mAb 413 IgG (4 μM) were measured by the Bethesda assay as described by Kasper, C. K. et al. (1975) *Thromb. Diath.*

*Haemorrh* 34:869–872. Inhibitor IgG was prepared as described by Leyte, A. et al. (1991) *J. Biol. Chem.* 266:740–746.

HP2 does not react with anti-A2 antibodies. Therefore, residues 373–603 must contain an epitope for anti-A2 antibodies.

Preparation of Hybrid Human-porcine Factor VIII and Assay by Splicing by Overlap Extension (SOE).

Several more procoagulant recombinant hybrid human/porcine factor VIII B-domainless molecules with porcine amino acid substitutions in the human A2 region have been prepared to further narrow the A2 epitope. Besides restriction site techniques, the "splicing by overlap extension" method (SOE) as described by Ho et al. (1989) *Gene* 77:51–59, has been used to substitute any arbitrary region of porcine factor VIII cDNA. In SOE, the splice site is defined by overlapping oligonucleotides that can be amplified to produce the desired cDNA by PCR. Ten cDNA constructs, designated HP4 through HP13, have been made. They were inserted into the ReNeo expression vector, stably transfected into baby hamster kidney cells, and expressed to high levels [0.5–1 μg (approximately 3–6 units)/$10^7$ cells/24 hours] as described in Example 7. Factor VIII coagulant activity was determined in the presence and absence of a model murine monoclonal inhibitory antibody specific for the A2 domain, mAb413. In the absence of inhibitor, all of the constructs had a specific coagulant activity that was indistinguishable from B(–) human factor VIII.

The hybrid human/porcine factor VIII constructs were assayed for reactivity with the anti-A2 inhibitor mAb413 using the Bethesda assay [Kasper et al. (1975) *Thromb. Diath. Haemorrh.* 34:869–872]. The Bethesda unit (BU) is the standard method for measuring inhibitor titers. The results are shown in Table V, and are compared to recombinant human factor VIII.

TABLE V

COMPARISON OF IMMUNOREACTIVITY OF AMINO ACID-SUBSTITUTED HYBRID HUMAN/PORCINE FACTOR VIII

| Construct | Porcine Substitution | Inhibition mAb413(BU/mg IgG) |
| --- | --- | --- |
| Human B(–) fVIII | None | 1470 |
| HP4 | 373–540 | <0.7 |
| HP5 | 373–508 | <0.7 |
| HP6 | 373–444 | 1450 |
| HP7 | 445–508 | <0.7 |
| HP8 | 373–483 | 1250 |
| HP9 | 484–508 | <0.7 |
| HP10 | 373–403 | 1170 |
| HP11 | 404–508 | <0.7 |
| HP12 | 489–508 | <0.7 |
| HP13 | 484–488 | <0.7 |

The boundaries of porcine substitutions are defined by the first amino acids that differ between human and porcine factor VIII at the $NH_2$-terminal and C-terminal ends of the insertion. As shown in Table V, if the Bethesda titer is not measurable (<0.7 BU/mg IgG), then an A2 epitope lies in the region of substituted porcine sequence. The epitope has been progressively narrowed to residues 484–509 (SEQ ID NO:2), consisting of only 25 residues, as exemplified by non-reactivity of mAb413 with HP9. Among constructs HP4 through HP11, HP9 was the most "humanized" construct that did not react with the inhibitor. This indicates that a critical region in the A2 epitope is located within the sequence Arg484-Ile508.

Based on a comparison between human and porcine factor VIII of the amino acid sequence in this critical region, two more constructs, HP12 and HP13, were made, in which corresponding porcine amino acid sequence was substituted for human amino acids 489–508 and 484–488, respectively. Neither reacts with mAb413. This indicates that residues on each side of the Arg488-Ser489 bond are important for reaction with A2 inhibitors. In HP12 only 5 residues are non-human, and in HP13 only 4 residues are non-human. The 484–508, 484–488, and 489–508 porcine substituted hybrids displayed decreased inhibition by A2 inhibitors from four patient plasmas, suggesting that there is little variation in the structure of the A2 epitope according to the inhibitor population response.

The reactivity of the most humanized constructs, HP9, HP12, and HP13, with two anti-A2 IgG5 preparations prepared from inhibitor plasmas was determined. Like mAb413, these antibodies did not react with HP9, HP12, and HP13, but did react with the control constructs HP(–) and HP8.

The region between 484–508 can be further analyzed for final identification of the critical A2 epitope, using the same procedures.

The methods described in Examples 7 and 8 can be used to prepare other hybrid human/non-porcine mammalian factor VIII with amino acid substitution in the human A2 or other domains, hybrid human/animal or animal/animal factor VIII with amino acid substitution in any domain, or hybrid factor VII equivalent molecules or fragments of any of these, such hybrid factor VIII having reduced or absent immunoreactivity with anti-factor VIII antibodies.

EXAMPLE 9

Elimination of Human Factor VIII A2 Inhibitor Reactivity by Site-directed Mutagenesis Example 8 showed that substitution of the porcine sequence bounded by residues 484 and 508 into the human factor VIII A2 domain yields a molecule that has markedly decreased reactivity with a panel of A2-specific factor VIII inhibitors [see also Healey et al. (1995) *J. Biol. Chem.* 270:14505–14509]. In this region, there are 9 amino acid differences between human and porcine factor VIII. These nine residues in human B-domainless factor VIII, R484, P485, Y487, P488, R489, P492, V495, F501, and I508 (using the single letter amino code), were individually changed to alanine by site-directed mutagenesis. Additionally, Mlu1 and Sac2 restriction sites were placed in the factor VIII cDNA at sites 5' and 3' relative to the A2 epitope, without changing the amino acids corresponding to these sites, to facilitate cloning. The nine mutants were stably transfected into baby hamster kidney cells and expressed to high levels. All nine produced biologically active factor VIII. They were partially purified and concentrated by heparin-Sepharose chromatography as described by Healey et al.

The mutants have been characterized by their reactivity with the murine monoclonal inhibitor MAb413 as in Example 7. This inhibitor recognizes the same or a very closely clustered epitope in the A2 domain as all human inhibitors studied to date. Inhibitor reactivity was measured using the Bethesda assay. Briefly, the Bethesda titer of an inhibitor is the dilution of inhibitor that inhibits factor VIII by 50% in a standard one-stage factor VIII clotting assay. For example, if solution of antibody is diluted $\frac{1}{420}$ and it inhibits the recombinant factor VIII test sample by 50%, the Bethesda titer is 420 U. In the case of a pure monoclonal like MAb413, the mass of antibody is known, so the results are expressed in Bethesda units (BU) per mg MAb413. To find the 50% inhibition point, a range of dilutions of MAb413 was made and 50% inhibition was found by a curve fitting procedure. The results are as follows:

TABLE VI

| Mutation | MAb413 titer (BU/mg) | % Reactivity* |
|---|---|---|
| Wild-type, B(−)fVIII | 9400 | — |
| R484 → A | 160 | 1.7 |
| P485 → A | 4000 | 42 |
| Y487 → A | 50 | 0.53 |
| S488 → A | 3500 | 37 |
| R489 → A | 1.6 | 0.015 |
| R490 → A | — | <0.5> |
| P492 → A | 630 | 6.7 |
| V495 → A | 10700 | 113 |
| F501 → A | 11900 | 126 |
| I508 → A | 5620 | 60 |

*Relative to wild-type

These results indicate that it is possible to reduce the antigenicity of factor VIII toward the model A2 inhibitor by over a factor of 10 by making alanine substitutions at positions 484, 487, 489, and 492. The reactivity of R489→A is reduced by nearly 4 orders of magnitude. Any of these alanine substitutions can be therapeutically useful to reduce the antigenicity and the immunogenicity of factor VIII.

The results confirm the efficacy of alanine-scanning mutagenesis and further demonstrate that biological activity is retained even though the amino acid sequence has been altered within an epitope reactive to an inhibitory antibody. Five of the nine sites where the human and porcine sequences differ are also sites where the human and murine sequences differ. The factor VIIIs having alanine substitutions at these positions are therefore examples of a hybrid factor VIII equivalent molecule having a sequence with no known sequence identify with any presently known mammalian factor VIII.

Further modification, e.g. by combining two alanine substitutions, can also provide greatly reduced antigenicity for a wider range of patients, since polyclonal variant antibodies differing from patient to patient can react with variants of the factor VIII A2 epitope. In addition, immunogenicity (the capacity to induce antibodies) is further reduced by incorporation of more than one amino acid substitution. Such substitutions can include both alanine, porcine-specific amino acids, or other amino acids known to have low immunogenic potential. The substitutions at positions 490, 495 and 501 are likely to be useful in reducing immunogenicity. In addition, these substitutions are likely to reduce reactivity to certain patient antibodies.

Other effective, antigenicity-reducing amino acid substitutions, besides alanine, can be made as long as care is taken to avoid those previously noted as being major contributors to antigen-antibody binding energy, or having bulky or charged side chains. Amino acids whose substitutions within an epitope reduce the antigenic reactivity thereof are termed "immunoreactivity-reducing" amino acids herein. Besides alanine, other immunoreactivity-reducing amino acids include, without limitation, methionine, leucine, serine and glycine. It will be understood that the reduction of immunoreactivity achievable by a given amino acid will also depend on any effects the substitution may have on protein conformation, epitope accessibility and the like.

Amino acid substitutions at other sites within the A2 epitope (amino acids 484–508) besides those that differ between the human and porcine sequences, are further able to reduce reactivity toward inhibitory antibodies. Alanine scanning mutagenesis can be used to provide alanine substitutions for any amino acid within the A2 epitope. Each resulting modified factor VIII can be assayed for procoagulant activity and for inhibition of that activity by an inhibitory antibody. Other immunoreactivity reducing amino acids besides alanine can be substituted to reduce antigenicity of the resulting modified factor VIII. Amino acid replacements can be combined in a single factor VIII molecule to maximize the desired properties resulting from such substitutions.

Replacement of those amino acids that contribute the most to the binding energy of an antibody-factor VIII interaction is most preferred. These include substitution of an immunoreactivity-reducing amino acid at any of positions 493, 496, 499, 500, 502, 503, 505 and 507. The data for replacements of this type, at positions 484, 485, 499, 490, 492, 501 and 508 has demonstrated that such replacements retain procoagulant activity and decrease susceptibility to inhibition by inhibitory antibodies. (Table VI) Histidine replacements have been observed in naturally-occurring sequences. For example, at position 504 the histidine of mouse factor VIII is replaced by leucine in both porcine and human factor VIII. Both porcine and mouse factor VIII have a histidine at position 487, where human factor VIII has tyrosine. Replacing the tyrosine with alanine at position 487 results in active procoagulant with substantially reduced antigenicity (Table VI). By analogy, replacement of histidine at position 497 by an immunoreactivity-reducing amino acid can also result in retention of procoagulant activity and contribute to reduced inhibition by inhibitory antibodies. Immunoreactivity-reducing amino acids can also be substituted at positions 486, 488, 491, 494, 498, 504 and 506. Although the existing amino acids at these positions seem less likely to contribute to antibody binding, it has been demonstrated (Table VI) that substitution of an immunoreactivity-reducing amino acid at such sites, e.g. S488A, contributes to reducing antibody inhibition of procoagulant activity.

From a comparison of the human, porcine, murine (FIGS. 1A–1H) and canine [Cameron, C. et al. (1998) *Thromb. Haemost.* 79:317–322] sequences within the A2 epitope, it is evident that the region tolerates a significant amount of sequence variability. Only 12 loci are conserved among all four species. None of these can be considered to be essential for procoagulant activity. In fact, replacement by alanine of the conserved arginine at position 490 (R490→A, Table VI) results in active modified factor VIII having reduced reactivity to an inhibitory antibody. One or more amino acid replacements can be made without substantially affecting procoagulant activity. For example, the replacement of two amino acids involved in antibody binding can reduce inhibition by an antibody to a greater extent than either one alone. Also, multiple replacements can render the resulting modified factor VIII less responsive to a wider variety of patient antibodies than a single amino acid replacement.

Individual amino acid replacements can be assessed for their properties of reduced antigenicity, as well as for other functional attributes of factor VIII. By evaluating the properties conferred by individual amino acid replacements, it is possible to identify desired combination replacements of two or more amino acids to provide a modified factor VIII having optimized properties, insofar as the region of amino acids 484–508 is concerned.

Site directed mutagenesis can be used to modify the factor VIII DNA in the region encoding amino acids 484–508 so as to provide a sequence that encodes the modified factor VIII having a desired amino acid replacement. At the appropriate site of the human factor VIII DNA sequence, the triplet encoding an existing amino acid can be changed by site directed mutagenesis to encode the desired amino acid. The triplet encoding the desired amino acid can be any one of the known triplets specified by the genetic code. Altering the natural sequence to encode a single amino acid substitution can often be accomplished with a single base change, occasionally more, up to a maximum of three base changes. By using site-specific mutagenesis, all necessary base substitutions can be readily carried out so as to alter the existing coding to that needed to encode the desired amino acid substitution. Some examples of base changes leading to specified amino acid substitutions are given below. These are exemplary only, and not comprehensive:

| | |
|---|---|
| R484 → G | CGT → GGT |
| P485 → A | CCT → GCT |
| L486 → S | TTG → TCG |
| Y487 → L | TAT → CTT |
| S488 → L | TCA → TTA |
| R489 → S | AGG → AGT |
| R490 → G | AGA → GGA |
| L491 → S | TTA → TCA |
| P492 → L | CCA → CTA |
| K493 → A | AAA → GCA |
| G494 → S | GGT → AGT |
| V495 → A | GTA → GCA |
| K496 → M | AAA → ATG |
| H497 → L | CAT → CTT |
| L498 → S | TTG → TCG |
| K499 → M | AAG → ATG |
| D500 → A | GAT → GCT |
| F501 → S | TTT → TCT |
| P502 → L | CCA → CTA |
| I503 → M | ATT → ATG |
| L504 → M | CTG → ATG |
| P505 → A | CCA → GCA |
| G506 → A | GGA → GCA |
| E507 → G | GAA → GGA |
| I508 → M | ATA → ATG |

The foregoing examples demonstrate that many immunoreactivity-reducing amino acid substitutions can be accomplished by single nucleotide changes. Other desired substitutions can be accomplished in similar fashion, making reference to the genetic code to select a desired nucleotide triplet encoding the intended amino acid substituent, then introducing the nucleotide changes necessary to generate the intended triplet, by site-directed mutagenesis. Multiply-substituted modified factor VIII can be made by simple combinations of nucleotide changes such as those just described. For example, a modified factor VIII having two amino acids of the A2 domain replaced, e.g. R489→A and P492→L can be made by introducing AGG→GCG and CCA→CTA at the appropriate sites, a change of three nucleotides. Any other desired change or combination of changes can be designed and carried out, essentially as just described. The modified factor VIII DNA sequence resulting from the described site-directed mutagenesis then differs from the natural human sequence or from otherwise modified sequences as described elsewhere herein, only by having the defined nucleotide substitution(s) at the defined site. Procoagulant activity is assayed as previously described, (Examples 1 and 8), by either the one-stage or two-stage assay. Assay for inhibitor titer is the Bethesda assay, described above and by Kasper, C. K. et al., supra, Example 8.

EXAMPLE 10

Klenow fragment, phosphorylated ClaI linkers, NotI linkers, T4 ligase, and Taq DNA polymerase were purchased from Promega (Madison, Wis.). Polynucleotide kinase was purchased from Life Technologies, Inc., Gaithersburg, Md. $\gamma^{32}$P-ATP (Redivue, >5000 Ci/mmol) was purchased from Amersham. pBluescript II KS- and E. coli Epicurean XL1-Blue cells were purchased from Stratagene (La Jolla, Calif.). Synthetic oligonucleotides were purchased from Life Technologies, Inc. or Cruachem, Inc. 5'-phosphorylated primers were used when PCR products were produced for cloning purposes. Nucleotide (nt) numbering of oligonucleotides used as primers for polymerase chain reaction (PCR) amplification of porcine fVIII cDNA or genomic DNA uses the human fVIII cDNA as reference (Wood et al. (1984) supra).

Porcine spleen total RNA was isolated by acid guanidinium thiocyanate-phenol-chloroform extraction [Chomczynski et al. (1987) Anal. Biochem. 162:156–159]. Porcine cDNA was prepared from total spleen RNA using Moloney murine leukemia virus reverse transcriptase (RT) and random hexamers to prime the reaction (First-Strand cDNA Synthesis Kit, Pharmacia Biotech) unless otherwise indicated. RT reactions contained 45 mM Tris-Cl, pH 8.3, 68 mM KCl, 15 mM DTT, 9 mM $MgCl_2$, 0.08 mg/ml bovine serum albumin and 1.8 mM deoxynucleotide triphosphate (dNTP). Porcine genomic DNA was isolated from spleen using a standard procedure (Strauss, W. M. (1995) In *Current Protocols in Molecular Biology*, F. M. Ausubel et al., editors, John Wiley & Sons, pp. 2.2.1–2.2.3). Isolation of DNA from agarose gels was done using Geneclean II (Bio 101) or Quiex II Gel Extraction Kit (Qiagen).

PCR reactions were done using a Hybaid OmniGene thermocycler. For PCR reactions employing Taq DNA polymerase, reactions included 0.6 mM $MgCl_2$, 0.2 mM dNTPs, 0.5 µM oligonucleotide primers, 50 U/ml polymerase and 0.1 volume of first strand cDNA reaction mix. Except where indicated otherwise, PCR products were gel purified, blunt-ended with Klenow fragment, precipitated with ethanol, and either ligated to the EcoRV site of dephosphorylated pBluescript II KS- or ligated with phosphorylated ClaI linkers using T4 ligase, digested with ClaI, purified by Sephacryl S400 chromatography, and ligated to ClaI-cut, dephosphorylated pBluescript II KS-. Ligations were done using T4 DNA ligase (Rapid DNA ligation kit, Boehringer Mannheim) except where indicated otherwise. Insert-containing pBluescript II KS- plasmids were used to transform E. coli Epicurean XL1-Blue cells.

Sequencing of plasmid DNA was done using an Applied Biosystems 373a automated DNA sequencer and the PRISM dye terminator kit or manually using Sequenase v. 2.0 sequencing kit (Amersham Corporation). Direct sequencing of PCR products, including $^{32}$P-end labelling of oligonucleotides was done using a cycle sequencing protocol (dsDNA Cycle Sequencing System, Life Technologies).

Isolation of Porcine fVIII cDNA Clones Containing 5' UTR Sequence, Signal Peptide and A1 Domain Codons.

The porcine fVIII cDNA 5' to the A2 domain was amplified by nested RT-PCR of female pig spleen total RNA using a 5' rapid amplification of cDNA ends (5'-RACE) protocol (Marathon cDNA Amplification, Clontech, Version PR55453). This included first strand cDNA synthesis using a lock-docking oligo(dT) primer [Borson, N. D. et al. (1992) *PCR Methods Appl.* 2:144–148], second strand cDNA synthesis using E. coli DNA polymerase I, and ligation with a 5' extended double stranded adaptor, SEQ ID NO:13 5'-CTA ATA CGA CTC ACT ATA GGG CTC GAG CGG CCG CCC GGG CAG GT-3 3'-H₂N-CCCGTCCA-PO₄-5' whose short strand was blocked at the 3' end with an amino group to reduce non-specific PCR priming and which was complementary to the 8 nucleotides at the 3' end (Siebert, P. D., et al. (1995) *Nucleic. Acids. Res.* 23:1087–1088). The first round of PCR was done using an adaptor-specific oligonucleotide, SEQ ID NO:14 5'-CCA TCC TAA TAC GAC TCA CTA TAG GGC-3' (designated AP1) as sense primer, and a porcine fVIII A2 domain specific oligonucleotide SEQ ID NO:15 5'-CCA TTG ACA TGA AGA CCG TTT CTC-3' (nt 2081–2104) as antisense primer. The second round of PCR was done using a nested, adaptor-specific oligonucleotide, SEQ ID NO:16 5'-ACT CAC TAT AGG GCT CGA GCG GC-3' (designated AP2) as sense primer, and a nested, porcine A2 domain-specific oligonucleotide SEQ ID NO:17 5'-GGG TGC AAA GCG CTG ACA TCA GTG-3' (nt 1497–1520) as antisense primer. PCR was carried out using a commercial kit (Advantage cDNA PCR core kit) which employs an antibody-mediated hot start protocol [Kellogg, D. E. et al. (1994) *BioTechniques* 16:1134–1137]. PCR conditions included denaturation at 94° C. for 60 sec, followed by 30 cycles (first PCR) or 25 cycles (second PCR) of denaturation for 30 sec at 94° C., annealing for 30 sec at 60° C. and elongation for 4 min at 68° C. using tube temperature control. This procedure yielded a prominent ≈1.6 kb product which was consistent with amplification of a fragment extending approximately 150 bp into the 5' UTR. The PCR product was cloned into pBluescript using ClaI linkers. The inserts of four clones were sequenced in both directions.

The sequence of these clones included regions corresponding to 137 bp of the 5' UTR, the signal peptide, the A1 domain and part of the A2 domain. A consensus was reached in at least 3 of 4 sites. However, the clones contained an average of 4 apparent PCR-generated mutations, presumably due to the multiple rounds of PCR required to generate a clonable product. Therefore, we used sequence obtained from the signal peptide region to design a sense strand phosphorylated PCR primer, SEQ ID NO:18 5'-CCT CTC GAG CCA CCA TGT CGA GCC ACC ATG CAG CTA GAG CTC TCC ACC TG-3', designated RENEOPIGSP, for synthesis of another PCR product to confirm the sequence and for cloning into an expression vector. The sequence in bold represents the start codon. The sequence 5' to this represents sequence identical to that 5' of the insertion site into the mammalian expression vector ReNeo used for expression of fVIII (Lubin et al. (1994) supra). This site includes an XhoI cleavage site (underlined). RENEOPIGSP and the nt 1497–1520 oligonucleotide were used to prime a Taq DNA polymerase-mediated PCR reaction using porcine female spleen cDNA as a template. DNA polymerases from several other manufacturers failed to yield a detectable product. PCR conditions included denaturation at 94° C. for four min, followed by 35 cycles of denaturation for 1 min at 94° C., annealing for 2 min at 55° C. and elongation for 2 min at 72° C., followed by a final elongation step for 5 min at 72° C. The PCR product was cloned into pBluescript using ClaI linkers. The inserts of two of these clones were sequenced in both directions and matched the consensus sequence.

Isolation of Porcine fVIII cDNA Clones Containing A3, C1 and 5' Half of the C2 Domain Codons.

Initially, two porcine spleen RT-PCR products, corresponding to a B-A3 domain fragment (nt 4519–5571) and a C1-C2 domain fragment (nt 6405–6990) were cloned. The 3' end of the C2 domain that was obtained extended into the exon 26 region, which is the terminal exon in fVIII. The B-A3 product was made using the porcine-specific B domain primer, SEQ ID NO:19 5' CGC GCG GCC GCG CAT CTG G<u>CA AAG CTG AGT T</u> 3', where the underlined region corresponds to a region in porcine fVIII that aligns with nt 4519–4530 in human fVIII. The 5' region of the oligonucleotide includes a NotI site that was originally intended for cloning purposes. The antisense primer used in generating the B-A3 product, SEQ ID NO:20 5'-GAA ATA AGC CCA GGC TTT GCA GTC RAA-3' was based on the reverse complement of the human fVIII cDNA sequence at nt 5545–5571. The PCR reaction contained 50 mM KCl, 10 mM Tris-Cl, pH 9.0, 0.1% Triton X-100, 1.5 mM MgCl₂, 2.5 mM dNTPs, 20 µM primers, 25 units/ml Taq DNA polymerase and ½₀volume of RT reaction mix. PCR conditions were denaturation at 94° C. for 3 min, followed by 30 cycles of denaturation for 1 min at 94° C., annealing for 2 min at 50° C. and elongation for 2 min at 72° C. The PCR products were phosphorylated using T4 DNA kinase and NotI linkers were added. After cutting with NotI, the PCR fragments were cloned into the NotI site of BlueScript II KS- and transformed into XL1-Blue cells.

The C1-C2 product was made using the known human cDNA sequence to synthesize sense and antisense primers, SEQ ID NO:21 5'-AGG AAA TTC CAC TGG AAC CTT N-3' (nt 6405–6426) and SEQ ID NO:22 5'-CTG GGG GTG AAT CG AAG GTA GCG N-3' (reverse complement of nt 6966–6990), respectively. PCR conditions were identical to those used to generate the B-A2 product. The resulting fragment was ligated to the pNOT cloning vector using the Prime PCR Cloner Cloning System (5 Prime-3 Prime, Inc., Boulder, Colo.) and grown in JM109 cells.

The B-A3 and C1-C2 plasmids were partially sequenced to make the porcine-specific sense and antisense oligonucleotides, SEQ ID NO:23 5'-GAG TTC ATC GGG AAG ACC TGT TG-3' (nt 4551–4573) and SEQ ID NO:24 5'-ACA GCC CAT CAA CTC CAT GCG AAG-3' (nt 6541–6564), respectively. These oligonucleotides were used as primers to generate a 2013 bp RT-PCR product using a Clontech Advantage cDNA PCR kit. This product, which corresponds to human nt 4551–6564, includes the region corresponding to the light chain activation peptide (nt 5002–5124), A3 domain (nt 5125–6114) and most of the C1 domain (nt 6115–6573). The sequence of the C1-C2 clone had established that human and porcine cDNAs from nt 6565 to the 3' end of the C1 domain were identical. The PCR product cloned into the EcoRV site of pBluescript II KS-. Four clones were completely sequenced in both directions. A consensus was reached in at least 3 of 4 sites.

Isolation of Porcine fVIII cDNA Clones Containing the 3' Half of the C2 Domain Codons.

The C2 domain of human fVIII (nucleotides 6574–7053) is contained within exons 24–26 [Gitschier J. et al. (1984) *Nature* 312:326–330]. Human exon 26 contains 1958 bp, corresponding nucleotides 6901–8858. It includes 1478 bp of 3' untranslated sequence. Attempts to clone the exon 26 cDNA corresponding to the 3' end of the C2 domain and the 3'UTR by 3' RACE [Siebert et al. (1995) supra], inverse PCR [Ochman, H. et al. (1990) *Biotechnology* (N.Y). 8:759–760], restriction site PCR [Sarkar, G. et al. (1993) *PCR Meth. Appl.* 2:318–322], "unpredictably primed" PCR [Dominguez, O. et al. (1994) *Nucleic. Acids Res.* 22:3247–3248] and by screening a porcine liver cDNA library failed. 3' RACE was attempted using the same adaptor-ligated double stranded cDNA library that was used to successfully used to clone the 5' end of the porcine fVIII cDNA. Thus, the failure of this method was not due to the absence of cDNA corresponding to exon 26.

A targeted gene walking PCR procedure [Parker, J. D. et al. (1991) *Nucleic. Acids. Res.* 19:3055–3060] was used to clone the 3' half of the C2 domain. A porcine-specific sense primer, SEQ ID NO:25 5'-TCAGGGCAATCAGGACTCC-3' (nt 6904–6924) was synthesized based on the initial C2 domain sequence and was used in a PCR reaction with nonspecific "walking" primers selected from oligonucleotides available in the laboratory. The PCR products were then targeted by primer extension analysis [Parker et al. (1991) *BioTechniques* 10:94–101] using a $^{32}$P-end labelled porcine-specific internal primer, SEQ ID NO:26 5'-CCGTGGTGAACGCTCTGGACC-3' (nt 6932–6952). Interestingly, of the 40 nonspecific primers tested, only two yielded positive products on primer extension analysis and these two corresponded to an exact and a degenerate human sequence at the 3' end of the C2 domain: SEQ ID NO:27 5'-GTAGAGGTCCTGTGCCTCGCAGCC-3' (nt 7030–7053) and SEQ ID NO:28 5'-GTAGAGSTSCTGKGCCTCRCAKCCYAG-3', (nt 7027–7053). These primers had initially been designed to yield a product by conventional RT-PCR but failed to yield sufficient product that could be visualized by ethidium bromide dye binding. However, a PCR product could be identified by the more sensitive primer extension method. This product was gel-purified and directly sequenced. This extended the sequence of porcine fVIII 3' to nt 7026.

Additional sequence was obtained by primer extension analysis of a nested PCR product generated using the adaptor-ligated double-stranded cDNA library used in the 5'-RACE protocol described previously. The first round reaction used the porcine exact primer SEQ ID NO:29 5'-CTTCGCATGGAGTTGATGGGCTGT-3' (nt 6541–6564) and the AP1 primer. The second round reaction used SEQ ID NO:30 5'-AATCAGGACTCCTCCACCCCCG-3' (nt 6913–6934) and the AP2 primer. Direct PCR sequencing extended the sequence 3' to the end of the C2 domain (nt 7053). The C2 domain sequence was unique except at nt 7045 near the 3' end of the C2 domain. Analysis of repeated PCR reactions yielded either A, G or a double read of A/G at this site.

Sequencing was extended into the 3'UTR using two additional primers, SEQ ID NO:31 5'-GGA TCC ACC CCA CGA GCT GG-3' (nt 6977–6996) and SEQ ID NO:32 5'-CGC CCT GAG GCT CGA GGT TCT AGG-3' (nt 7008–7031). Approximately 15 bp of 3' UTR sequence were obtained, although the sequence was unclear at several sites. Several antisense primers then were synthesized based on the best estimates of the 3' untranslated sequence. These primers included the reverse complement of the TGA stop codon at their 3' termini. PCR products were obtained from both porcine spleen genomic DNA and porcine spleen cDNA that were visualized by agarose gel electrophoresis and ethidium bromide staining using a specific sense primer SEQ ID NO:33 5'-AAT CAG GAC TCC TCC ACC CCC G-3' (nt 6913–6934) and the 3' UTR antisense primer, SEQ ID NO:34 5'-CCTTGCAGGAATTCGATTCA-3'. To obtain sufficient quantities of material for cloning purposes, a second round of PCR was done using a nested sense primer, SEQ ID NO:35 5'-CCGTGGTGAACGCTCTGGACC-3' (nt 6932–6952) and the same antisense primer. The 141 bp PCR product was cloned into EcoRV-cut pBluescript II KS-. Sequence of three clones derived from genomic DNA and three clones derived from cDNA was obtained in both directions. The sequence was unambiguous except at nt 7045, where genomic DNA was always A and cDNA was always G.

Multiple DNA Sequence Alignments of Human, Porcine, and Mouse fVIII (FIGS. 1A–1H).

Alignments of the signal peptide, A1, A2, A3, C1, and C2 regions were done using the CLUSTALW program [Thompson, J. D. et al. (1994) *Nucleic. Acids. Res.* 22:4673–4680]. Gap open and gap extension penalties were 10 and 0.05 respectively. The alignments of the human, mouse, and pig B domains have been described previously [Elder et al. (1993) supra]. The human A2 sequence corresponds to amino acids 373–740 in SEQ ID NO:2. The porcine A2 amino acid sequence is given in SEQ ID NO:4, and the mouse A2 domain amino acid sequence is given in SEQ ID NO:6, amino acids 392–759.

EXAMPLE 11

Expression of Active, Recombinant B-domainless Porcine Factor VIII (PB⁻)

Materials

Citrated hemophilia A and normal pooled human plasmas were purchased from George King Biomedical, Inc. Fetal bovine serum, geneticin, penicillin, streptomycin, DMEM/F12 medium and AIM-V medium were purchased from Life Technologies, Inc. Taq DNA polymerase was purchased from Promega. Vent DNA polymerase was purchased from New England Biolabs. Pfu DNA polymerase and the phagemid pBlueScript II KS⁻ were purchased from Stratagene. Synthetic oligonucleotides were purchased from Life Technologies or Cruachem, Inc. Restriction enzymes were purchased from New England Biolabs or Promega. 5'-phosphorylated primers were used when PCR products were produced for cloning purposes. Nucleotide (nt) numbering of oligonucleotides used as primers for polymerase chain reaction (PCR) amplification of porcine fVIII cDNA or genomic DNA uses the human fVIII cDNA as reference [Wood et al. (1984) *Nature* 312:330–337]. A fVIII expression vector, designated HB⁻/ReNeo, was obtained from Biogen, Inc. HB⁻/ReNeo contains ampicillin and geneticin resistance genes and a human fVIII cDNA that lacks the entire B domain, defined as the Ser741-Arg1648 cleavage fragment produced by thrombin. To simplify mutagenesis of fVIII C2 domain cDNA, which is at the 3' end of the fVIII insert in ReNeo, a NotI site was introduced two bases 3' to the stop codon of HB⁻/ReNeo by splicing-by-overlap extension (SOE) mutagenesis [Horton, R. M. et al. (1993) *Methods Enzymol.* 217:270–279]. This construct is designated HB⁻ReNeo/NotI.

Total RNA was isolated by acid guanidinium thiocyanate-phenol-chloroform extraction [Chomczynski, P. et al. (1987) *Anal. Biochem.* 162:156–159]. cDNA was synthesized from mRNA using Moloney murine leukemia virus reverse transcriptase (RT) and random hexamers according to instructions supplied by the manufacturer (First-Strand cDNA Synthesis Kit, Pharmacia Biotech). Plasmid DNA was purified using a Qiagen Plasmid Maxi Kit (Qiagen, Inc.). PCR reactions were done using a Hybaid OmniGene thermocycler using Taq, Vent, or Pfu DNA polymerases. PCR products were gel purified, precipitated with ethanol, and ligated into plasmid DNA using T4 DNA ligase (Rapid DNA ligation kit, Boehringer Mannheim). Insert-containing plasmids were used to transform *E. coli* Epicurean XL1-Blue cells. All novel fVIII DNA sequences generated by PCR were confirmed by dideoxy sequencing using an Applied Biosystems 373a automated DNA sequencer and the PRISM dye terminator kit.

Construction of a Hybrid fVIII Expression Vector, HP20, Containing the Porcine C2 Domain.

A porcine fVIII cDNA corresponding to the 3' end of the C1 domain and all of the C2 domain was cloned into pBluescript by RT-PCR from spleen total RNA using primers based on known porcine fVIII cDNA sequence [Healy, J. F. et al. (1996) *Blood* 88:4209–4214]. This construct and HB⁻/ReNeo were used as templates to construct a human C1-porcine C2 fusion product in pBlueScript by SOE mutagenesis. The C1-C2 fragment in this plasmid was removed with ApaI and NotI and ligated into ApaI/NotI-cut HB⁻/ReNeo/NotI to produce HP20/ReNeo/NotI.

Construction of B-domain Deleted Hybrid Human/porcine fVIII Containing the Porcine Light Chain (HP18)

The human fVIII light chain consists of amino acid residues Asp1649-Tyr2332. The corresponding residues in the porcine fVIII cDNA were substituted for this region of HB⁻ to produce a hybrid human/porcine fVIII molecule designated HP18. This was done by substituting a PCR product corresponding to porcine A2 region, the A3 domain, the C1 domain, and part of the C2 domain for the corresponding region in HP20. To facilitate constructions, a synonymous AvrII site was introduced into nt 2273 at the junction of the A2 and A3 domains of HP20 by SOE mutagenesis.

Construction of B-domain Deleted Hybrid Human/Porcine fVIII Containing the Porcine Signal Peptide, A1 Domain and A2 Domain (HP22)

The human fVIII signal peptide, A1 domain and A2 domains consist of amino acid residues Met(-19)-Arg740. The corresponding residues in the porcine fVIII cDNA were substituted for this region of HB⁻ to produce a molecule designated HP22. Additionally, a synonymous AvrII site was introduced into nt 2273 at the junction of the A2 and A3 domains of HP22 by SOE mutagenesis. HP22 was constructed by fusion of a porcine signal peptide-A1-partial A2 fragment in pBlueScript [Healy et al. (1996) supra] with a B-domainless hybrid human/porcine fVIII containing the porcine A2 domain, designated HP1 [Lubin et al. (1994) supra].

Construction of Porcine B Domainless fVIII-(PB⁻)

A SpeI/NotI fragment of HP18/BS (+AvrII) was digested with AvrII/NotI and ligated into AvrII/NotI-digested HP22/BS (+AvrII) to produce a construct PB⁻/BS (+AvrII), which consists of the porcine fVIII lacking the entire B domain. PB- was cloned into ReNeo by ligating an XbaI/NotI fragment of PB⁻/BS (+AvrII) into HP22/ReNeo/NotI (+AvrII).

Expression of Recombinant fVIII Molecules

PB⁻/ReNeo/NotI (+AvrII) and HP22/ReNeo/NotI (+AvrII) were transiently transfected into COS cells and expressed as described previously [Lubin, I. M. et al. (1994) *J. Biol. Chem.* 269:8639–8641]. HB⁻/ReNeo/NotI and no DNA (mock) were transfected as a control.

The fVIII activity of PB⁻, HP22, and HB⁻ were measured by a chromogenic assay as follows. Samples of fVIII in COS cell culture supernatants were activated by 40 nM thrombin in a 0.15 M NaCl, 20 mM HEPES, 5 Mm cAC12, 0.01% Tween-80, pH 7.4 in the presence of 10 nM factor IXa, 425 nM factor X, and 50 µM unilamellar phosphatidylserine-[phosphatidylcholine (25/75 w/w) vesicles. After 5 min, the reaction was stopped with 0.05 M EDTA and 100 nM recombinant desulfatohirudin and the resultant factor Xa was measured by chromogenic substrate assay. In the chromogenic substrate assay, 0.4 mM Spectrozyme Xa was added and the rate of para-nitroanilide release was measured by measuring the absorbance of the solution at 405 nm.

Results of independently transfected duplicate cell culture supernatants (absorbance at 405 nm per minute)

HB⁻: 13.9
PB⁻: 139
HP22: 100
mock: <0.2

These results indicate that porcine B-domainless fVIII and a B-domainless fVIII consisting of the porcine A1 and A2 subunits are active and suggest that they have superior activity to human B-domainless fVIII.

PB⁻ was partially purified and concentrated from the growth medium by heparin-Sepharose chromatography. Heparin-Sepharose (10 ml) was equilibrated with 0.075 M NaCl, 10 mM HEPES, 2.5 mM CaCl$_2$, 0.005% Tween-80, 0.02% sodium azide, pH 7.40. Medium (100–200 ml) from expressing cells was applied to the heparin-Sepharose, which then was washed with 30 ml of equilibration buffer without sodium azide. PB⁻ was eluted with 0.65 M NaCl, 20 mM HEPES, 5 mM CaCl$_2$, 0.01% Tween-80, pH 7.40 and was stored at −80° C. The yield of fVIII coagulant activity was typically 50–75%.

Stable Expression of Porcine B-domainless fVIII (PB⁻)

Transfected cell lines were maintained in Dulbecco's modified Eagle's medium-F12 containing 10% fetal bovine serum, 50 U/ml penicillin, 50 µg/ml streptomycin. Fetal bovine serum was heat inactivated at 50° C. for one hour before use. HB⁻/ReNeo and PB⁻ReNeo/NotI (+AvrII) were stably transfected into BHK cells and selected for geneticin resistance using a general protocol that has been described previously [Lubin et al. (1994) *Biol. Chem.* 269:8639–8641] except that expressing cells were maintained in growth medium containing 600 µg/ml geneticin. Cells from Corning T-75 flasks grown to confluence were transferred to Nunc triple flasks in medium containing 600 µg/ml geneticin and grown to confluence. The medium was removed and replaced with serum-free, AIM-V medium (Life Technologies, Inc.) without geneticin. Factor VIII expression was monitored by one-stage factor VIII coagulant activity (vide supra) and 100–150 ml of medium was collected once daily for four to five days. Maximum expression levels in medium for HB⁻ and PB⁻ were 102 units per ml and 10–12 units per ml of factor VIII coagulant activity, respectively.

Purification of PB⁻

PB⁻ was precipitated from culture supernatant using 60% saturated ammonium sulfate and then purified by W3-3 immunoaffinity chromatography and mono Q high pressure liquid chromatography as described previously for the purification of plasma-derived porcine factor VIII [Lollar et al. (1993) Factor VIII/factor VIIIa. *Methods Enzymol.* 222:128–143]. The specific coagulant activity of PB⁻ was measured by a one-stage coagulation assay [Lollar et al. (1993) supra] and was similar to plasma-derived porcine factor VIII.

When analyzed by SDS-polyacrylamide gel electrophoresis, the PB⁻ preparation contained three bands of apparent molecular masses 160 kDa, 82 kDa, and 76 kDa. The 82 kDa and 76 kDa bands have been previously described as heterodimer containing the A1-A2 and ap-A3-C1-C2 domains (where ap refers to an activation peptide) [Toole et al. (1984) *Nature* 312:342–347]. The 160 kDa band was transferred to a polyvinylidene fluoride membrane and subjected to NH2-terminal sequencing, which yielded Arg-Ile-Xx-Xx-Tyr (where Xx represents undermined) which is the NH2-terminal sequence of single chain factor VIII [Toole et al. (1984) supra]. Thus, PB⁻ is partially processed by cleavage between the A2 and A3 domains, such that it consists of two forms, a single chain A1-A2-ap-A3-C1-C2 protein and a A1-A2/ap-A3-C1-C2 heterodimer. Similar processing of recombinant HB⁻ has been reported [Lind et al. (1995) *Eur. J. Biochem.* 232:19–27].

Characterization of Porcine Factor VIII

We have determined the cDNA sequence of porcine fVIII corresponding to 137 bp of the 5' UTR, the signal peptide coding region (57 bp), and the A1 (1119 bp), A3 (990 bp), C1 (456 bp), and C2 (483 bp) domains. Along with previously published sequence of the B domain and light chain activation peptide regions [Toole et al. (1986) supra] and the A2 domain [Lubin et al. (1994) supra], the sequence reported here completes the determination of the porcine fVIII cDNA corresponding to the translated product. A fragment that included the 5' UTR region, signal peptide, and A1 domain cDNA was cloned using a 5'-RACE RT-PCR protocol. A primer based on human C2 sequence was successful in producing an RT-PCR product that led to cloning of the A3, C1, and 5' half of the C2 domain. The cDNA corresponding to the 3' half of the C2 domain and 3' UTR cDNA proved difficult to clone. The remainder of the C2 domain ultimately was cloned by a targeted gene walking PCR procedure [Parker et al. (1991) supra].

The sequence reported herein SEQ ID NO:36 was unambiguous except at nt 7045 near the 3' end of the C2 domain, which is either A or G as described hereinabove. The corresponding codon is GAC (Asp) or AAC (Asn). The human and mouse codons are GAC and CAG (Gln), respectively. Whether this represents a polymorphism or a reproducible PCR artifact is unknown. Recombinant hybrid human/porcine B-domainless fVIII cDNAs containing porcine C2 domain substitutions corresponding to both the GAC and AAC codons have been stably expressed with no detectable difference in procoagulant activity. This indicates that there is not a functional difference between these two C2 domain variants.

The alignment of the predicted amino acid sequence of full-length porcine fVIII SEQ ID NO:37 with the published human [Wood et al. (1984) supra] and murine [Elder et al. (1993) supra] sequences is shown in FIGS. 1A–1H along with sites for post-translational modification, proteolytic cleavage, and recognition by other macromolecules. The degree of identity of the aligned sequences is shown in Table VII. As noted previously, the B domains of these species are more divergent than the A or C domains. This is consistent with the observation that the B domain has no known function, despite its large size [Elder et al. (1993) supra; Toole et al. (1986) supra]. The results of the present invention confirm that the B domain or porcine fVIII is not necessary for activity. Based on the sequence data presented herein, porcine fVIII having all or part of the B-domain deleted can be synthesized by expressing the porcine fVIII coding DNA having deleted therefrom all or part of codons of the porcine B domain. There is also more divergence of sequences corresponding to the A1 domain APC/factor IXa cleavage peptide (residues 337–372) and the light chain activation peptide (Table VII). The thrombin cleavage site at position 336 to generate the 337–372 peptide is apparently lost in the mouse since this residue is glutamine instead of arginine [Elder et al. (1993) supra]. The relatively rapid divergence of thrombin cleavage peptides (or in mouse fVIII a possibly vestigial 337–372 activation peptide) has been previously noted for the fibrinopeptides [Creighton, T. E. (1993) In *Proteins: Structures and Molecular Properties*, W. H. Freeman, New York, pp. 105–138]. Lack of biological function of these peptides once cleaved has been cited as a possible reason for the rapid divergence. Arg562 in human fVIII has been proposed to be the more important cleavage site for activated protein C during the inactivation of fVIII and fVIIIa [Fay, P. J. et al. (1991) *J. Biol. Chem.* 266:20139–20145]. This site is conserved in human, porcine and mouse fVIII.

Potential N-linked glycosylation sites (NXS/T where X is not proline) can be seen in FIGS. 1A–1H. There are eight conserved N-linked glycosylation sites: one in the A1 domain, one in the A2 domain, four in the B domain, one in the A3 domain, and one in the C1 domain. The 19 A and C domain cysteines are conserved, whereas there is divergence of B domain cysteines. Six of the seven disulfide linkages in fVIII are found at homologous sites in factor V and ceruloplasmin, and both C domain disulfide linkages are found in factor V [McMullen, B. A. et al. (1995) *Protein Sci.* 4:740–746]. Human fVIII contains sulfated tyrosines at positions 346, 718, 719, 723, 1664, and 1680 [Pittman, D. D. et al. (1992) *Biochemistry* 31:3315–3325; Michnick, D. A. et al. (1994) *J. Biol. Chem.* 269:20095–20102]. These residues are conserved in mouse fVIII and porcine fVIII (FIG. 1), although the CLUSTALW program failed to align the mouse tyrosine corresponding to Tyr346 in human fVIII.

Mouse and pig plasma can correct the clotting defect in human hemophilia A plasma, which is consistent with the level of conservation of residues in the A and C domains of these species. The procoagulant activity of porcine fVIII is superior to that of human fVIII [Lollar, P. et al. (1992) *J. Biol. Chem.* 267:23652–23657]. The recombinant porcine factor VIII (B domain-deleted) expressed and purified as herein described also displays greater specific coagulant activity than human fVIII, being comparable to plasma-derived porcine fVIII. This may be due to a decreased spontaneous dissociation rate of the A2 subunit from the active A1/A2/A3-C1-C2 fVIIIa heterotrimer. Whether this difference in procoagulant activity reflects an evolutionary change in function as an example of species adaptation [Perutz, M. F. (1996) *Adv. Protein Chem.* 36:213–244] is unknown. Now that the porcine fVIII cDNA sequence corresponding to the translated product is complete, homolog scanning mutagenesis [Cunningham, B. C., et al. (1989) *Science* 243:1330–1336] may provide a way to identify structural differences between human and porcine fVIII that are responsible for the superior activity of the latter.

Porcine fVIII is typically less reactive with inhibitory antibodies that arise in hemophiliacs who have been transfused with fVIII or which arise as autoantibodies in the general population. This is the basis for using porcine fVIII concentrate in the management of patients with inhibitory antibodies [Hay and Lozier (1995) supra]. Most inhibitors are directed against epitopes located in the A2 domain or C2 domain [Fulcher, C. A. et al. (1985) *Proc. Natl. Acad. Sci. USA* 82:7728–7732; Scandella, D. et al. (1988) *Proc. Natl. Acad. Sci. USA* 85:6152–6156; Scandella, D. et al. (1989) *Blood* 74:1618–1626]. Additionally, an epitope of unknown significance has been identified that is in either the A3 or C1 domain [Scandella et al. (1989) supra; Scandella, D. et al. (1993) *Blood* 82:1767–1775; Nakai, H. et al. (1994) *Blood* 84:224a]. The A2 epitope has been mapped to residues 484–508 by homolog scanning mutagenesis [Healey et al. (1995) supra]. In this 25 residue segment, there is relatively low proportion of identical sequence (16/25 or 64%). It is interesting that this region, which appears to be functionally important based on the fact that antibodies to it are inhibitory, apparently has been subjected to relatively more rapid genetic drift. Alignment of the porcine A2 domain and A3 domains indicate that the A2 epitope shares no detectable homology with the corresponding region in the A3 domain.

The C2 inhibitor epitope of human fVIII has been proposed to be located to within residues 2248–2312 by deletion mapping [Scandella, D. et al. (1995) *Blood* 86:1811–1819]. Human and porcine fVIII are 83% identical in this 65 residue segment. However, homolog scanning mutagenesis of this region to characterize the C2 epitope has revealed that a major determinant of the C2 epitope was unexpectedly located in the region corresponding to human amino acids 2181–2243 (SEQ ID NO:2) and FIG. 1H.

Human-porcine hybrid factor VIII proteins were made in which various portions of the C2 domain of human factor VIII were replaced by the corresponding portions of porcine factor VIII, using the strategy herein described. (Example 8) The synthesis of the various C2-hybrid factor VIIIs was accomplished by constructing hybrid coding DNA, using the nucleotide sequence encoding the porcine C2 region given in SEQ ID NO:37. Each hybrid DNA was expressed in transfected cells, such that the hybrid factor VIIIs could be partially purified from the growth medium. Activity, in the absence of any inhibitor, was measured by the one-stage clotting assay.

A battery of five human inhibitors was used to test each hybrid factor VIII. The inhibitor plasmas containing anti factor VIII antibody had been previously shown to be directed against human C2 domain, based on the ability of recombinant human C2 domain to neutralize the inhibition. In all the test plasmas, the inhibitor titer was neutralized greater than 79% by C2 domain or light chain but less than 10% by recombinant human A2 domain. In addition the C2-hybrid factor VIIIs were tested against a murine monoclonal antibody, which binds the C2 domain, and like human C2 inhibitor antibodies, it inhibited the binding of factor VIII to phospholipid and to von Willebrand factor.

By comparing the antibody inhibitor titers against the C2-hybrid factor VIIIs, the major determinant of the human C2 inhibitor epitope was shown to be the region of residues 2181–2243 (SEQ ID NO:2, see also FIG. 1H). Anti-C2 antibodies directed to a region COOH-terminal to residue 2253 were not identified in four of the five patient sera. In comparing hybrids having porcine sequence corresponding to human amino acid residues numbers 2181–2199 and 2207–2243, it was apparent that both regions contribute to antibody binding. The porcine amino acid sequence corresponding to human residues 2181–2243 is numbered 1982–2044 in SEQ ID NO:37. The sequence of porcine DNA encoding porcine amino acids numbered 1982–2044 is nucleotides numbered 5944–6132 in SEQ ID NO:35.

Referring to FIG. 1H, it can be seen that in the region 2181–2243, there are 16 amino acid differences between the human and porcine sequences. The differences are found at residues 2181, 2182, 2188, 2195–2197, 2199, 2207, 2216, 2222, 2224–2227, 2234, 2238 and 2243. Amino acid replacement at one or more of these numbered residues can be carried out to make a modified human factor VIII non-reactive to human anti-C2 inhibitor antibodies. Alanine scanning mutagenesis provides a convenient method for generating alanine substitutions for naturally-occurring residues, as previously described. Amino acids other than alanine can be substituted as well, as described herein. Alanine substitutions for individual amino acids, especially those which are non-identical between human/porcine or human/mouse or which are most likely to contribute to antibody binding, can yield a modified factor VIII with reduced reactivity to inhibitory antibodies.

In addition, the strategy of inserting amino acids with lower potential to be immunogenic in the defined region of residues 2181–2243 yields modified factor VIIIs having reduced immunogenicity. Reduced immunogenicity factor VIII is useful as a factor VIII supplement for treatment of hemophilia A patients in preference to natural-sequence factor VIII. Patients treated with reduced immunogenicity factor VIII are less likely to develop inhibitory antibodies, and are therefore less likely to suffer from reduced effectiveness of treatment over their lifetimes.

FIGS. 1A–1H taken together provide an aligned sequence comparison of the human, pig and mouse factor VIII amino acid sequences. FIG. 1A compares signal peptide regions (human, SEQ ID NO:40; porcine, SEQ ID NO:37, amino acids 1–19; murine, SEQ ID NO:6, amino acids 1–19). Note that the amino acids in FIGS. 1A–1H are numbered at the first Alanine of the mature protein as number 1, with amino acids of the signal peptide assigned negative numbers. The Human fVIII sequence in SEQ ID NO:2 also begins with the first Alanine of the mature protein as amino acid number 1. In the amino acid sequences of mouse fVIII (SEQ ID NO:6) and porcine fVIII (SEQ ID No:37), the first amino acid (alanine) of the mature sequence is amino acid number 20. FIGS. 1A–1H shows an alignment of the corresponding sequences of human, mouse and pig fVIII, such that the regions of greatest amino acid identity are juxtaposed. The amino acid numbers in FIGS. 1A–1H apply to human fVIII only. FIG. 1B gives the amino acid sequences for the A1 domain of human (SEQ ID NO:2, amino acids 1–372), porcine (SEQ ID NO:37, amino acids 20–391), and murine (SEQ ID NO:6, amino acids 20–391). FIG. 1C provides amino acid sequences for the Factor VIII A2 domains from human (SEQ ID NO:2, amino acids 373–740), pig (SEQ ID NO:37, amino acids 392–759) and mouse (SEQ ID NO:6, amino acids 392–759). FIGS. 1D and 1D-1 provide the amino acid sequences of B domains of human factor VIII (SEQ ID NO:2, amino acids 741–1648), pig (SEQ ID NO:37, amino acids 760–1449) and mouse (SEQ ID NO:6, amino acids 760–1640). FIG. 1E compares the amino acid sequences of Factor VIII light chain activation peptides of human, pig and mouse (SEQ ID NO:2, amino acids 1649–1689; SEQ ID NO:37, amino acids 1450–1490; and SEQ ID NO:6, amino acids 1641–1678, respectively). FIG. 1F provides the sequence comparison for human, pig and mouse Factor VIII A3 domains (SEQ ID NO:2, amino acids 1690–2019; SEQ ID NO:37, amino acids 1491–1820; and SEQ ID NO:6, amino acids 1679–2006, respectively. FIG. 1G provides the amino acid sequences of the Factor VIII C1 domains of human, pig and mouse (SEQ ID NO:2, amino acids 2020–2172; SEQ ID NO:37, amino acids 1821–1973; and SEQ ID NO:6, amino acids 2007–2159, respectively). FIG. 1H provides sequence data for the C2 domains of the Factor VIII C2 domains of human, pig and mouse (SEQ ID NO:2, amino acids 2173–2332; SEQ ID NO:37, amino acids 1974–2133; and SEQ ID NO:6, amino acids 2160–2319, respectively).

The diamonds represent tyrosine sulfation sites, proposed binding sites for Factor IXa, phospholipid and Protein C are double-underlined, and regions involved in binding anti-A2 and anti-C2 inhibitory antibodies are italicized. Asterisks highlight amino acid sequences which are conserved. See also SEQ ID NO:36 (porcine factor VIII cDNA) and SEQ ID NO:37 (deduced amino acid sequence of porcine factor VIII). The human numbering system is used as the reference [Wood et al. (1984) supra]. The A1, A2, and B domains are defined by thrombin cleavage sites at positions 372 and 740 and an unknown protease cleavage site at 1648 as residues 1–372, 373–740, and 741–1648, respectively [Eaton, D. L. et al. (1986) *Biochemistry* 25:8343–8347]. The A3, C1, and C2 domains are defined as residues 1690–2019, 2020–2172, and 2173–2332, respectively [Vehar et al. (1984) supra]. Cleavage sites for thrombin (factor IIa), factor IXa, factor Xa and APC [Fay et al. (1991) supra; Eaton, D. et al. (1986) *Biochemistry* 25:505–512; Lamphear, B. J. et al. (1992) *Blood* 80:3120–3128] are shown by placing the enzyme name over the reactive arginine. An acidic peptide is cleaved from the fVIII light chain by thrombin or factor Xa at position 1689. Proposed binding sites for factor IXa [Fay, P. J. et al. (1994) *J. Biol. Chem.* 269:20522–20527; Lenting, P. J. et al. (1994) *J. Biol. Chem.* 269:7150–7155), phospholipid (Foster, P. A. et al. (1990) *Blood* 75:1999–2004) and protein C (Walker, F. J. et al. (1990) *J. Biol. Chem.* 265:1484–1489] are doubly underlined. Regions involved in binding anti-A2 [Lubin et al. (1994) supra; Healey et al. (1995) supra]; and previously proposed for anti-C2 inhibitory antibodies are italicized. The C2 inhibitor epitope identified as herein described (human amino acids 2181–2243) is shown by a single underline in FIG. 1H. Tyrosine sulfation sites [Pittman et al. (1992) supra; Michnick et al. (1994) supra] are shown by ♦.

The nucleotide sequence encoding the factor VIII protein lacking the B domain is given in SEQ ID NO:38, and the corresponding deduced amino acid sequence is provided in SEQ ID NO:39.

What is claimed is:

1. A DNA encoding modified human factor VIII A2 domain, said DNA having one or more nucleotide substitutions resulting in a coding change at one or more amino acid positions chosen from positions 484–508 of SEQ ID NO:2, said change encoding an immunoreactivity-reducing amino acid at the chosen position.

2. The DNA according to claim 1 wherein the amino acid position chosen is selected from the group consisting of 490, 493, 496, 499, 500, 502, 503, 505 and 507.

3. The DNA according to claim 1 wherein the amino acid position chosen is selected from the group consisting of 486, 491, 494, 498, 504 and 506.

4. The DNA according to claim 1 wherein the amino acid position chosen is amino acid position 497.

5. The DNA according to claim 1 wherein the amino acid position chosen is amino acid position 490.

6. An expression protein product of a DNA encoding a human or hybrid human and other non-human mammalian factor VIII, said DNA comprising a DNA encoding a modified A2 domain, the DNA having one or more nucleotide substitutions resulting in a coding change at one or more amino acid positions chosen from positions 484–508 of SEQ ID NO:2, said change encoding an immunoreactivity-reducing amino acid at the chosen position for the naturally-occurring amino acid.

7. The expression protein product of claim 6 wherein the DNA encoding the modified A2 domain encodes an amino acid substitution at one or more of amino acid positions selected from the group consisting of 490, 493, 496, 499, 500, 502, 503, 505 and 507.

8. The expression protein product of claim 6 wherein the DNA encoding the modified A2 domain encodes an amino acid substitution at one or more of amino acid positions selected from the group consisting of 486, 491, 494, 498, 504 and 506.

9. The expression protein product of claim 6 wherein the DNA encoding the modified A2 domain encodes an amino acid substitution at position 497.

10. The expression protein product of claim 6 wherein the DNA encoding the modified A2 domain encodes an amino acid substitution at position 490.

11. A method of making a modified mammalian factor VIII A2 domain comprising the steps of mutating DNA encoding the domain at one or more codons encoding amino acids at positions corresponding to 484–508 of human factor VIII whereby one or more mutated codons encoding an amino acid is substituted for a corresponding naturally-occurring codon, and expressing in a host cell DNA comprising the mutated codons, either independently or in contiguous translatable sequence with DNA encoding another domain of factor VIII, whereby a modified factor VIII A2 domain is made.

12. The method of claim 11 wherein the DNA to be mutated is human DNA.

13. The method of claim 11 wherein the DNA to be mutated is porcine DNA.

14. The method of claim 11 wherein the DNA to be mutated is murine DNA.

15. The method of claim 11 wherein a mutated codon encodes an immunoreactivity-reducing amino acid.

16. The method of claim 15 wherein a mutated codon encodes an amino acid at a position selected from the group consisting of 490, 493, 496, 499, 500, 502, 503, 505 and 507.

17. The method of claim 15 wherein a mutated codon encodes an amino acid at a position selected from the group consisting of 486, 491, 494, 498, 504 and 506.

18. The method of claim 15 wherein a mutated codon encodes an amino acid at position 497.

19. The method of claim 15 wherein a mutated codon encodes an amino acid at position 490.

* * * * *